US007902347B2

(12) United States Patent
Dai

(10) Patent No.: US 7,902,347 B2
(45) Date of Patent: Mar. 8, 2011

(54) HUMAN RON-RELATED GENE VARIANT ASSOCIATED WITH CANCERS

(75) Inventor: Ken-Shwo Dai, Hsinchu (TW)

(73) Assignee: Visgeneer, Inc., Hsuichu (TW)

(*) Notice: Subject to any disclaimer, the term of this patent is extended or adjusted under 35 U.S.C. 154(b) by 110 days.

(21) Appl. No.: 12/209,133

(22) Filed: Sep. 11, 2008

(65) Prior Publication Data

US 2009/0148897 A1 Jun. 11, 2009

Related U.S. Application Data

(62) Division of application No. 11/465,308, filed on Aug. 17, 2006, now Pat. No. 7,452,985.

(51) Int. Cl.

| | |
|---|---|
| ***C07H 21/02*** | (2006.01) |
| ***C07H 21/04*** | (2006.01) |
| ***C12N 15/00*** | (2006.01) |
| ***C12N 5/00*** | (2006.01) |
| ***C12N 5/02*** | (2006.01) |
| ***C12N 15/64*** | (2006.01) |

(52) U.S. Cl. .................... 536/23.1; 536/23.5; 536/24.33; 435/320.1; 435/325; 435/91.4

(58) Field of Classification Search ........................ None
See application file for complete search history.

(56) References Cited

U.S. PATENT DOCUMENTS

| | | | | |
|---|---|---|---|---|
| 6,900,016 B1 * | 5/2005 | Venter et al. | ...................... | 435/6 |
| 6,974,667 B2 * | 12/2005 | Horne et al. | ...................... | 435/6 |
| 2007/0083334 A1 | 4/2007 | Mintz et al. | | |

FOREIGN PATENT DOCUMENTS

| | | |
|---|---|---|
| EP | 06017649.2 | 1/2007 |
| WO | WO 2004023973 | 3/2004 |
| WO | WO 2004023973 A2 * | 3/2004 |

OTHER PUBLICATIONS

Angeloni, D., et al., The soluble sema domain of the RON receptor inhibits macrophage-stimulating protein-induced receptor activation. J. Biol. Chem. 279:3726-32, (2004).

Camp, E.R., et al., RON, a tyrosine kinase receptor involved in tumor progression and metastasis.Ann Surg Oncol. 12:273-81, (2005).

Collesi, C., et al., A splicing variant of the RON transcript induces constitutive tyrosine kinase activity and an invasive phenotype. Molecular and Cellular Biology 16:5518-5526, (1996).

Maggiora, P., et al., Overexpression of the RON gene in human breast carcinoma. Oncogene 16:2927-2933, (1998).

Peace, B.E., et al., RON receptor signaling augments mammary tumor formation and metastasis in a murine model of breast cancer. Cancer Res. 65:1285-93, (2005).

Wang, M., et al., Identification of a novel splicing product of the RON receptor tyrosine kinase in human colorectal carcinoma cells. Carcinogenesis 21: 1507-1512 (2000).

Wang, M., et al., Oncogenic and invasive potentials of human macrophage-stimulating protein receptor, the RON receptor tyrosine kinase. Carcinogenesis 24:1291-300, (2003).

Willet, C., et al., Human RON receptor protein. Database EMBL, Accession No. AAW82791, Apr. 12, 1999.

Willett, C.G., et al., Differential screening of a human chromosome 3 library identifies hepatocyte growth factor-like/macrophage-stimulating protein and its receptor in injured lung. Possible implications for neuroendocrine cell survival. J Clin Invest. 99:2979-91, (1997).

Xu, X., et al., RNA-mediated gene splicing of the RON receptor tyrosine kinase alters oncogenic phenotypes of human colorectal carcinoma cells. Oncogene 23:8464-8474, (2004).

Zhou, Y., et al., Altered expression of the RON receptor tyrosine kinase in primary human colorectal adenocarcinomas: generation of different splicing Ron variants and their oncogenic potential. Oncogene 22:186-197, (2003).

* cited by examiner

*Primary Examiner* — Misook Yu
*Assistant Examiner* — Anne M. Gussow
(74) *Attorney, Agent, or Firm* — Baker & McKenzie LLP

(57) ABSTRACT

The invention relates to the nucleic acid and polypeptide sequences of three novel human Ron-related gene variants (Ron-V1, Ron-V2, and Ron-V3). The invention also provides a process for producing the polypeptides of the variants, as well as uses for the nucleic acid, polypeptide and antibodies to same in diagnosing human breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

5 Claims, 53 Drawing Sheets

FIG. 1A-1 SEQ ID NO: 1

| | | | | | | |
|---|---|---|---|---|---|---|
| ggatcctcta | gggtcccagc | tcgcctcgat | ggagctcctc | ccgccgctgc | ctcagtcctt | 60 |
| cctgttgctg | ctgctgttgc | ctgccaagcc | cgcggcgggc | gaggactggc | agtgcccgcg | 120 |
| caccccctac | gcggcctctc | gcgactttga | cgtgaagtac | gtggtgccca | gcttctccgc | 180 |
| cggaggcctg | gtacaggcca | tggtgaccta | cgagggcgac | agaaatgaga | gtgctgtgtt | 240 |
| tgtagccata | cgcaatcgcc | tgcatgtgct | tgggcctgac | ctgaagtctg | tccagagcct | 300 |
| ggccacgggc | cctgctggag | accctggctg | ccagacgtgt | gcagcctgtg | gcccaggacc | 360 |
| ccacggccct | cccggtgaca | cagacacaaa | ggtgctggtg | ctggatcccg | cgctgcctgc | 420 |
| gctggtcagt | tgtggctcca | gcctgcaggg | ccgctgcttc | ctgcatgacc | tagagcccca | 480 |
| agggacagcc | gtgcatctgg | cagcgccagc | ctgcctcttc | tcagcccacc | ataaccggcc | 540 |
| cgatgactgc | cccgactgtg | tggccagccc | attgggcacc | cgtgtaactg | tggttgagca | 600 |
| aggccaggcc | tcctatttct | acgtggcatc | ctcactggac | gcagccgtgg | ctggcagctt | 660 |
| cagcccacgc | tcagtgtcta | tcaggcgtct | caaggctgac | gcctcgggat | tcgcaccggg | 720 |
| ctttgtggcg | ttgtcagtgc | tgcccaagca | tcttgtctcc | tacagtattg | aatacgtgca | 780 |
| cagcttccac | acgggagcct | tcgtatactt | cctgactgta | cagccggcca | gcgtgacaga | 840 |
| tgatcctagt | gccctgcaca | cacgcctggc | acggcttagc | gccactgagc | cagagttggg | 900 |
| tgactatcgg | gagctggtcc | tcgactgcag | atttgctcca | aaacgcaggc | gccgggggc | 960 |
| cccagaaggc | ggacagccct | accctgtgct | gcaggtggcc | cactccgctc | cagtgggtgc | 1020 |
| ccaacttgcc | actgagctga | gcatcgccga | gggccaggaa | gtactatttg | gggtctttgt | 1080 |
| gactggcaag | gatggtggtc | ctggcgtggg | ccccaactct | gtcgtctgtg | ccttccccat | 1140 |
| tgacctgctg | gacacactaa | ttgatgaggg | tgtggagcgc | tgttgtgaat | ccccagtcca | 1200 |
| tccaggcctc | cggcgaggcc | tcgacttctt | ccagtcgccc | agtttttgcc | ccaacccgcc | 1260 |
| tggcctggaa | gccctcagcc | ccaacaccag | ctgccgccac | ttccctctgc | tggtcagtag | 1320 |
| cagcttctca | cgtgtggacc | tattcaatgg | gctgttggga | ccagtacagg | tcactgcatt | 1380 |
| gtatgtgaca | cgccttgaca | acgtcacagt | ggcacacatg | ggcacaatgg | atgggcgtat | 1440 |
| cctgcaggtg | gagctggtca | ggtcactaaa | ctacttgctg | tatgtgtcca | acttctcact | 1500 |
| gggtgacagt | gggcagcccg | tgcagcggga | tgtcagtcgt | cttggggacc | acctactctt | 1560 |
| tgcctctggg | gaccaggttt | tccaggtacc | tatccgaggc | cctggctgcc | gccacttcct | 1620 |
| gacctgtggg | cgttgcctaa | gggcatggca | tttcatgggc | tgtggctggt | gtgggaacat | 1680 |
| gtgcggccag | cagaaggagt | gtcctggctc | ctggcaacag | gaccactgcc | cacctaagct | 1740 |
| tactgagttc | cacccccaca | gtggacctct | aaggggcagt | acaaggctga | ccctgtgtgg | 1800 |
| ctccaacttc | taccttcacc | cttctggtct | ggtgcctgag | ggaacccatc | aggtcactgt | 1860 |
| gggccaaagt | ccctgccggc | cactgcccaa | ggacagctca | aaactcagac | cagtgccccg | 1920 |
| gaaagacttt | gtagaggagt | ttgagtgtga | actggagccc | ttgggcaccc | aggcagtggg | 1980 |
| gcctaccaac | gtcagcctca | ccgtgactaa | catgccaccg | ggcaagcact | tccgggtaga | 2040 |
| cggcacctcc | gtgctgagag | gcttctcttt | catggagcca | gtgctgatag | cagtgcaacc | 2100 |
| cctctttggc | ccacgggcag | gaggcacctg | tctcactctt | gaaggccaga | gtctgtctgt | 2160 |
| aggcaccagc | cgggctgtgc | tggtcaatgg | gactgagtgt | ctgctagcac | gggtcagtga | 2220 |

FIG. 1A-2 SEQ ID NO: 1 cont.

```
ggggcagctt  ttatgtgcca  cacccccctgg  ggccacggtg  gccagtgtcc  cccttagcct   2280
gcaggtgggg  ggtgcccagg  tacctggttc  ctggaccttc  cagtacagag  aagaccctgt   2340
cgtgctaagc  atcagcccca  actgtggcta  catcaactcc  cacatcacca  tctgtggcca   2400
gcatctaact  tcagcatggc  acttagtgct  gtcattccat  gacgggctta  gggcagtgga   2460
aagcaggtgt  gagaggcagc  ttccagagca  gcagctgtgc  cgccttcctg  aatatgtggt   2520
ccgagacccc  cagggatggg  tggcagggaa  tctgagtgcc  cgaggggatg  gagctgctgg   2580
ctttacactg  cctggctttc  gcttcctacc  cccaccccat  ccacccagtg  ccaacctagt   2640
tccactgaag  cctgaggagc  atgccattaa  gtttgagtat  attgggctgg  gcgctgtggc   2700
tgactgtgtg  ggtatcaacg  tgaccgtggg  tggtgagagc  tgccagcacg  agttccgggg   2760
ggacatggtt  gtctgccccc  tgcccccatc  cctgcagctt  ggccaggatg  gtgccccatt   2820
gcaggtctgc  gtagatggtg  aatgtcatat  cctgggtaga  gtggtgcggc  cagggccaga   2880
tggggtccca  cagagcacgc  tccttggtat  cctgctgcct  ttgctgctgc  ttgtggctgc   2940
actggcgact  gcactggtct  tcagctactg  gtggcggagg  aagcagctag  ttcttcctcc   3000
caacctgaat  gacctggcat  ccctggacca  gactgctgga  gccacacccc  tgcctattct   3060
gtactcgggc  tctgactaca  gaagtggcct  tgcactccct  gccattgatg  gtctggattc   3120
caccacttgt  gtccatggag  catccttctc  cgatagtgaa  gatgaatcct  gtgtgccact   3180
gctgcggaaa  gagtccatcc  agctaaggga  cctggactct  gcgctcttgg  ctgaggtcaa   3240
ggatgtgctg  attccccatg  agcgggtggt  cacccacagt  gaccgagtca  ttggcaaagg   3300
ccactttgga  gttgtctacc  acggagaata  catagaccag  gcccagaatc  gaatccaatg   3360
tgccatcaag  tcactaagtc  gcatcacaga  gatgcagcag  gtggaggcct  tcctgcgaga   3420
ggggctgctc  atgcgtggcc  tgaaccaccc  gaatgtgctg  gctctcattg  gtatcatgtt   3480
gccacctgag  ggcctgcccc  atgtgctgct  gccctatatg  tgccacggtg  acctgctcca   3540
gttcatccgc  tcacctcagc  ggaaccccac  cgtgaaggac  ctcatcagct  ttggcctgca   3600
ggtagcccgc  ggcatggagt  acctggcaga  gcagaagttt  gtgcacaggg  acctggctgc   3660
gcggaactgc  atgctggacg  agtcattcac  agtcaaggtg  gctgactttg  gtttggcccg   3720
cgacatcctg  gacagggagt  actatagtgt  tcaacagcat  cgccacgctc  gcctacctgt   3780
gaagtggatg  gcgctggaga  gcctgcagac  ctatagattt  accaccaagt  ctgatgtgtg   3840
gtcatttggt  gtgctgctgt  gggaactgct  gacacggggt  gccccaccat  accgccacat   3900
tgaccctttt  gaccttaccc  acttcctggc  ccagggtcgg  cgcctgcccc  agcctgagta   3960
ttgccctgat  tctctgtacc  aagtgatgca  gcaatgctgg  gaggcagacc  cagcagtgcg   4020
acccaccttc  agagtactag  tgggggaggt  ggagcagata  gtgtctgcac  tgcttgggga   4080
ccattatgtg  cagctgccag  caacctacat  gaacttgggc  cccagcacct  cgcatgagat   4140
gaatgtgcgt  ccagaacagc  cgcagttctc  acccatgcca  gggaatgtac  gccggccccg   4200
gccactctca  gagcctcctc  ggcccacttg  acttagttct  tgggctggac  ctgcttagct   4260
gccttgagct  aaccccaagg  ctgcctctgg  gccatgccag  gccagagcag  tggccctcca   4320
ccttgttcct  gccctttaac  tttcagaggc  aataggtaaa  tgggcccatt  aggtccctca   4380
ctccacagag  tgagccagtg  agggcagtcc  tgcaacatgt  atttatggag  tgcctgctgt   4440
ggaccctgtc  ttctgggcac  agtggactca  gcagtgacca  caccaacact  gacccttgaa   4500
ccaataaagg  aacaaatgac  tattaaagca  caaaaaaaaa  a                        4541
```

FIG. 1B-1 SEQ ID NO: 2

Met Glu Leu Leu Pro Pro Leu Pro Gln Ser Phe Leu Leu Leu Leu Leu
5 10 15
Leu Pro Ala Lys Pro Ala Ala Gly Glu Asp Trp Gln Cys Pro Arg Thr
20 25 30
Pro Tyr Ala Ala Ser Arg Asp Phe Asp Val Lys Tyr Val Val Pro Ser
35 40 45
Phe Ser Ala Gly Gly Leu Val Gln Ala Met Val Thr Tyr Glu Gly Asp
50 55 60
Arg Asn Glu Ser Ala Val Phe Val Ala Ile Arg Asn Arg Leu His Val
65 70 75 80
Leu Gly Pro Asp Leu Lys Ser Val Gln Ser Leu Ala Thr Gly Pro Ala
85 90 95
Gly Asp Pro Gly Cys Gln Thr Cys Ala Ala Cys Gly Pro Gly Pro His
100 105 110
Gly Pro Pro Gly Asp Thr Asp Thr Lys Val Leu Val Leu Asp Pro Ala
115 120 125
Leu Pro Ala Leu Val Ser Cys Gly Ser Ser Leu Gln Gly Arg Cys Phe
130 135 140
Leu His Asp Leu Glu Pro Gln Gly Thr Ala Val His Leu Ala Ala Pro
145 150 155 160
Ala Cys Leu Phe Ser Ala His His Asn Arg Pro Asp Asp Cys Pro Asp
165 170 175
Cys Val Ala Ser Pro Leu Gly Thr Arg Val Thr Val Val Glu Gln Gly
180 185 190
Gln Ala Ser Tyr Phe Tyr Val Ala Ser Ser Leu Asp Ala Ala Val Ala
195 200 205
Gly Ser Phe Ser Pro Arg Ser Val Ser Ile Arg Arg Leu Lys Ala Asp
210 215 220
Ala Ser Gly Phe Ala Pro Gly Phe Val Ala Leu Ser Val Leu Pro Lys
225 230 235 240
His Leu Val Ser Tyr Ser Ile Glu Tyr Val His Ser Phe His Thr Gly
245 250 255
Ala Phe Val Tyr Phe Leu Thr Val Gln Pro Ala Ser Val Thr Asp Asp
260 265 270
Pro Ser Ala Leu His Thr Arg Leu Ala Arg Leu Ser Ala Thr Glu Pro
275 280 285
Glu Leu Gly Asp Tyr Arg Glu Leu Val Leu Asp Cys Arg Phe Ala Pro
290 295 300
Lys Arg Arg Arg Arg Gly Ala Pro Glu Gly Gly Gln Pro Tyr Pro Val
305 310 315 320
Leu Gln Val Ala His Ser Ala Pro Val Gly Ala Gln Leu Ala Thr Glu
325 330 335
Leu Ser Ile Ala Glu Gly Gln Glu Val Leu Phe Gly Val Phe Val Thr
340 345 350
Gly Lys Asp Gly Gly Pro Gly Val Gly Pro Asn Ser Val Val Cys Ala
355 360 365
Phe Pro Ile Asp Leu Leu Asp Thr Leu Ile Asp Glu Gly Val Glu Arg
370 375 380
Cys Cys Glu Ser Pro Val His Pro Gly Leu Arg Arg Gly Leu Asp Phe
385 390 395 400
Phe Gln Ser Pro Ser Phe Cys Pro Asn Pro Pro Gly Leu Glu Ala Leu
405 410 415
Ser Pro Asn Thr Ser Cys Arg His Phe Pro Leu Leu Val Ser Ser Ser
420 425 430
Phe Ser Arg Val Asp Leu Phe Asn Gly Leu Leu Gly Pro Val Gln Val
435 440 445
Thr Ala Leu Tyr Val Thr Arg Leu Asp Asn Val Thr Val Ala His Met
450 455 460
Gly Thr Met Asp Gly Arg Ile Leu Gln Val Glu Leu Val Arg Ser Leu
465 470 475 480

FIG. 1B-2 SEQ ID NO: 2 cont.

```
Asn Tyr Leu Leu Tyr Val Ser Asn Phe Ser Leu Gly Asp Ser Gly Gln
                485                 490                 495
Pro Val Gln Arg Asp Val Ser Arg Leu Gly Asp His Leu Leu Phe Ala
            500                 505                 510
Ser Gly Asp Gln Val Phe Gln Val Pro Ile Arg Gly Pro Gly Cys Arg
        515                 520                 525
His Phe Leu Thr Cys Gly Arg Cys Leu Arg Ala Trp His Phe Met Gly
    530                 535                 540
Cys Gly Trp Cys Gly Asn Met Cys Gly Gln Gln Lys Glu Cys Pro Gly
545                 550                 555                 560
Ser Trp Gln Gln Asp His Cys Pro Pro Lys Leu Thr Glu Phe His Pro
                565                 570                 575
His Ser Gly Pro Leu Arg Gly Ser Thr Arg Leu Thr Leu Cys Gly Ser
            580                 585                 590
Asn Phe Tyr Leu His Pro Ser Gly Leu Val Pro Glu Gly Thr His Gln
        595                 600                 605
Val Thr Val Gly Gln Ser Pro Cys Arg Pro Leu Pro Lys Asp Ser Ser
    610                 615                 620
Lys Leu Arg Pro Val Pro Arg Lys Asp Phe Val Glu Glu Phe Glu Cys
625                 630                 635                 640
Glu Leu Glu Pro Leu Gly Thr Gln Ala Val Gly Pro Thr Asn Val Ser
                645                 650                 655
Leu Thr Val Thr Asn Met Pro Pro Gly Lys His Phe Arg Val Asp Gly
            660                 665                 670
Thr Ser Val Leu Arg Gly Phe Ser Phe Met Glu Pro Val Leu Ile Ala
        675                 680                 685
Val Gln Pro Leu Phe Gly Pro Arg Ala Gly Gly Thr Cys Leu Thr Leu
    690                 695                 700
Glu Gly Gln Ser Leu Ser Val Gly Thr Ser Arg Ala Val Leu Val Asn
705                 710                 715                 720
Gly Thr Glu Cys Leu Leu Ala Arg Val Ser Glu Gly Gln Leu Leu Cys
                725                 730                 735
Ala Thr Pro Pro Gly Ala Thr Val Ala Ser Val Pro Leu Ser Leu Gln
            740                 745                 750
Val Gly Gly Ala Gln Val Pro Gly Ser Trp Thr Phe Gln Tyr Arg Glu
        755                 760                 765
Asp Pro Val Val Leu Ser Ile Ser Pro Asn Cys Gly Tyr Ile Asn Ser
    770                 775                 780
His Ile Thr Ile Cys Gly Gln His Leu Thr Ser Ala Trp His Leu Val
785                 790                 795                 800
Leu Ser Phe His Asp Gly Leu Arg Ala Val Glu Ser Arg Cys Glu Arg
                805                 810                 815
Gln Leu Pro Glu Gln Gln Leu Cys Arg Leu Pro Glu Tyr Val Val Arg
            820                 825                 830
Asp Pro Gln Gly Trp Val Ala Gly Asn Leu Ser Ala Arg Gly Asp Gly
        835                 840                 845
Ala Ala Gly Phe Thr Leu Pro Gly Phe Arg Phe Leu Pro Pro Pro His
    850                 855                 860
Pro Pro Ser Ala Asn Leu Val Pro Leu Lys Pro Glu Glu His Ala Ile
865                 870                 875                 880
Lys Phe Glu Tyr Ile Gly Leu Gly Ala Val Ala Asp Cys Val Gly Ile
                885                 890                 895
Asn Val Thr Val Gly Gly Glu Ser Cys Gln His Glu Phe Arg Gly Asp
            900                 905                 910
Met Val Val Cys Pro Leu Pro Pro Ser Leu Gln Leu Gly Gln Asp Gly
        915                 920                 925
Ala Pro Leu Gln Val Cys Val Asp Gly Glu Cys His Ile Leu Gly Arg
    930                 935                 940
Val Val Arg Pro Gly Pro Asp Gly Val Pro Gln Ser Thr Leu Leu Gly
945                 950                 955                 960
```

FIG. 1B-3 SEQ ID NO: 2 cont.

```
Ile Leu Leu Pro Leu Leu Leu Leu Val Ala Ala Leu Ala Thr Ala Leu
                965                 970                 975
Val Phe Ser Tyr Trp Trp Arg Arg Lys Gln Leu Val Leu Pro Pro Asn
            980                 985                 990
Leu Asn Asp Leu Ala Ser Leu Asp Gln Thr Ala Gly Ala Thr Pro Leu
        995                 1000                1005
Pro Ile Leu Tyr Ser Gly Ser Asp Tyr Arg Ser Gly Leu Ala Leu Pro
    1010                1015                1020
Ala Ile Asp Gly Leu Asp Ser Thr Thr Cys Val His Gly Ala Ser Phe
1025                1030                1035                1040
Ser Asp Ser Glu Asp Glu Ser Cys Val Pro Leu Leu Arg Lys Glu Ser
                1045                1050                1055
Ile Gln Leu Arg Asp Leu Asp Ser Ala Leu Leu Ala Glu Val Lys Asp
            1060                1065                1070
Val Leu Ile Pro His Glu Arg Val Val Thr His Ser Asp Arg Val Ile
        1075                1080                1085
Gly Lys Gly His Phe Gly Val Val Tyr His Gly Glu Tyr Ile Asp Gln
    1090                1095                1100
Ala Gln Asn Arg Ile Gln Cys Ala Ile Lys Ser Leu Ser Arg Ile Thr
1105                1110                1115                1120
Glu Met Gln Gln Val Glu Ala Phe Leu Arg Glu Gly Leu Leu Met Arg
                1125                1130                1135
Gly Leu Asn His Pro Asn Val Leu Ala Leu Ile Gly Ile Met Leu Pro
            1140                1145                1150
Pro Glu Gly Leu Pro His Val Leu Leu Pro Tyr Met Cys His Gly Asp
        1155                1160                1165
Leu Leu Gln Phe Ile Arg Ser Pro Gln Arg Asn Pro Thr Val Lys Asp
    1170                1175                1180
Leu Ile Ser Phe Gly Leu Gln Val Ala Arg Gly Met Glu Tyr Leu Ala
1185                1190                1195                1200
Glu Gln Lys Phe Val His Arg Asp Leu Ala Ala Arg Asn Cys Met Leu
                1205                1210                1215
Asp Glu Ser Phe Thr Val Lys Val Ala Asp Phe Gly Leu Ala Arg Asp
            1220                1225                1230
Ile Leu Asp Arg Glu Tyr Tyr Ser Val Gln Gln His Arg His Ala Arg
        1235                1240                1245
Leu Pro Val Lys Trp Met Ala Leu Glu Ser Leu Gln Thr Tyr Arg Phe
    1250                1255                1260
Thr Thr Lys Ser Asp Val Trp Ser Phe Gly Val Leu Leu Trp Glu Leu
1265                1270                1275                1280
Leu Thr Arg Gly Ala Pro Pro Tyr Arg His Ile Asp Pro Phe Asp Leu
                1285                1290                1295
Thr His Phe Leu Ala Gln Gly Arg Arg Leu Pro Gln Pro Glu Tyr Cys
            1300                1305                1310
Pro Asp Ser Leu Tyr Gln Val Met Gln Gln Cys Trp Glu Ala Asp Pro
        1315                1320                1325
Ala Val Arg Pro Thr Phe Arg Val Leu Val Gly Glu Val Glu Gln Ile
    1330                1335                1340
Val Ser Ala Leu Leu Gly Asp His Tyr Val Gln Leu Pro Ala Thr Tyr
1345                1350                1355                1360
Met Asn Leu Gly Pro Ser Thr Ser His Glu Met Asn Val Arg Pro Glu
                1365                1370                1375
Gln Pro Gln Phe Ser Pro Met Pro Gly Asn Val Arg Arg Pro Arg Pro
            1380                1385                1390
Leu Ser Glu Pro Pro Arg Pro Thr
        1395                1400
```

FIG. 1C-1 Coding Sequence (SEQ ID NO: 1 & 2)

```
atg  gag  ctc  ctc  ccg  ccg  ctg  cct  cag  tcc  ttc  ctg  ttg  ctg  ctg  ctg   48
Met  Glu  Leu  Leu  Pro  Pro  Leu  Pro  Gln  Ser  Phe  Leu  Leu  Leu  Leu  Leu
                    5                        10                       15
ttg  cct  gcc  aag  ccc  gcg  gcg  ggc  gag  gac  tgg  cag  tgc  ccg  cgc  acc   96
Leu  Pro  Ala  Lys  Pro  Ala  Ala  Gly  Glu  Asp  Trp  Gln  Cys  Pro  Arg  Thr
               20                       25                       30
ccc  tac  gcg  gcc  tct  cgc  gac  ttt  gac  gtg  aag  tac  gtg  gtg  ccc  agc  144
Pro  Tyr  Ala  Ala  Ser  Arg  Asp  Phe  Asp  Val  Lys  Tyr  Val  Val  Pro  Ser
          35                       40                       45
ttc  tcc  gcc  gga  ggc  ctg  gta  cag  gcc  atg  gtg  acc  tac  gag  ggc  gac  192
Phe  Ser  Ala  Gly  Gly  Leu  Val  Gln  Ala  Met  Val  Thr  Tyr  Glu  Gly  Asp
     50                       55                       60
aga  aat  gag  agt  gct  gtg  ttt  gta  gcc  ata  cgc  aat  cgc  ctg  cat  gtg  240
Arg  Asn  Glu  Ser  Ala  Val  Phe  Val  Ala  Ile  Arg  Asn  Arg  Leu  His  Val
65                       70                       75                       80
ctt  ggg  cct  gac  ctg  aag  tct  gtc  cag  agc  ctg  gcc  acg  ggc  cct  gct  288
Leu  Gly  Pro  Asp  Leu  Lys  Ser  Val  Gln  Ser  Leu  Ala  Thr  Gly  Pro  Ala
                    85                       90                       95
gga  gac  cct  ggc  tgc  cag  acg  tgt  gca  gcc  tgt  ggc  cca  gga  ccc  cac  336
Gly  Asp  Pro  Gly  Cys  Gln  Thr  Cys  Ala  Ala  Cys  Gly  Pro  Gly  Pro  His
               100                      105                      110
ggc  cct  ccc  ggt  gac  aca  gac  aca  aag  gtg  ctg  gtg  ctg  gat  ccc  gcg  384
Gly  Pro  Pro  Gly  Asp  Thr  Asp  Thr  Lys  Val  Leu  Val  Leu  Asp  Pro  Ala
          115                      120                      125
ctg  cct  gcg  ctg  gtc  agt  tgt  ggc  tcc  agc  ctg  cag  ggc  cgc  tgc  ttc  432
Leu  Pro  Ala  Leu  Val  Ser  Cys  Gly  Ser  Ser  Leu  Gln  Gly  Arg  Cys  Phe
     130                      135                      140
ctg  cat  gac  cta  gag  ccc  caa  ggg  aca  gcc  gtg  cat  ctg  gca  gcg  cca  480
Leu  His  Asp  Leu  Glu  Pro  Gln  Gly  Thr  Ala  Val  His  Leu  Ala  Ala  Pro
145                      150                      155                      160
gcc  tgc  ctc  ttc  tca  gcc  cac  cat  aac  cgg  ccc  gat  gac  tgc  ccc  gac  528
Ala  Cys  Leu  Phe  Ser  Ala  His  His  Asn  Arg  Pro  Asp  Asp  Cys  Pro  Asp
                    165                      170                      175
tgt  gtg  gcc  agc  cca  ttg  ggc  acc  cgt  gta  act  gtg  gtt  gag  caa  ggc  576
Cys  Val  Ala  Ser  Pro  Leu  Gly  Thr  Arg  Val  Thr  Val  Val  Glu  Gln  Gly
               180                      185                      190
cag  gcc  tcc  tat  ttc  tac  gtg  gca  tcc  tca  ctg  gac  gca  gcc  gtg  gct  624
Gln  Ala  Ser  Tyr  Phe  Tyr  Val  Ala  Ser  Ser  Leu  Asp  Ala  Ala  Val  Ala
          195                      200                      205
ggc  agc  ttc  agc  cca  cgc  tca  gtg  tct  atc  agg  cgt  ctc  aag  gct  gac  672
Gly  Ser  Phe  Ser  Pro  Arg  Ser  Val  Ser  Ile  Arg  Arg  Leu  Lys  Ala  Asp
     210                      215                      220
gcc  tcg  gga  ttc  gca  ccg  ggc  ttt  gtg  gcg  ttg  tca  gtg  ctg  ccc  aag  720
Ala  Ser  Gly  Phe  Ala  Pro  Gly  Phe  Val  Ala  Leu  Ser  Val  Leu  Pro  Lys
225                      230                      235                      240
cat  ctt  gtc  tcc  tac  agt  att  gaa  tac  gtg  cac  agc  ttc  cac  acg  gga  768
His  Leu  Val  Ser  Tyr  Ser  Ile  Glu  Tyr  Val  His  Ser  Phe  His  Thr  Gly
                    245                      250                      255
gcc  ttc  gta  tac  ttc  ctg  act  gta  cag  ccg  gcc  agc  gtg  aca  gat  gat  816
Ala  Phe  Val  Tyr  Phe  Leu  Thr  Val  Gln  Pro  Ala  Ser  Val  Thr  Asp  Asp
               260                      265                      270
cct  agt  gcc  ctg  cac  aca  cgc  ctg  gca  cgg  ctt  agc  gcc  act  gag  cca  864
Pro  Ser  Ala  Leu  His  Thr  Arg  Leu  Ala  Arg  Leu  Ser  Ala  Thr  Glu  Pro
          275                      280                      285
gag  ttg  ggt  gac  tat  cgg  gag  ctg  gtc  ctc  gac  tgc  aga  ttt  gct  cca  912
Glu  Leu  Gly  Asp  Tyr  Arg  Glu  Leu  Val  Leu  Asp  Cys  Arg  Phe  Ala  Pro
     290                      295                      300
aaa  cgc  agg  cgc  cgg  ggg  gcc  cca  gaa  ggc  gga  cag  ccc  tac  cct  gtg  960
Lys  Arg  Arg  Arg  Arg  Gly  Ala  Pro  Glu  Gly  Gly  Gln  Pro  Tyr  Pro  Val
305                      310                      315                      320
```

FIG. 1C-2 Coding Sequence (SEQ ID NO: 1 & 2) cont.

```
ctg cag gtg gcc cac tcc gct cca gtg ggt gcc caa ctt gcc act gag 1008
Leu Gln Val Ala His Ser Ala Pro Val Gly Ala Gln Leu Ala Thr Glu
                325                 330                 335
ctg agc atc gcc gag ggc cag gaa gta cta ttt ggg gtc ttt gtg act 1056
Leu Ser Ile Ala Glu Gly Gln Glu Val Leu Phe Gly Val Phe Val Thr
            340                 345                 350
ggc aag gat ggt ggt cct ggc gtg ggc ccc aac tct gtc gtc tgt gcc 1104
Gly Lys Asp Gly Gly Pro Gly Val Gly Pro Asn Ser Val Val Cys Ala
        355                 360                 365
ttc ccc att gac ctg ctg gac aca cta att gat gag ggt gtg gag cgc 1152
Phe Pro Ile Asp Leu Leu Asp Thr Leu Ile Asp Glu Gly Val Glu Arg
    370                 375                 380
tgt tgt gaa tcc cca gtc cat cca ggc ctc cgg cga ggc ctc gac ttc 1200
Cys Cys Glu Ser Pro Val His Pro Gly Leu Arg Arg Gly Leu Asp Phe
385                 390                 395                 400
ttc cag tcg ccc agt ttt tgc ccc aac ccg cct ggc ctg gaa gcc ctc 1248
Phe Gln Ser Pro Ser Phe Cys Pro Asn Pro Pro Gly Leu Glu Ala Leu
                405                 410                 415
agc ccc aac acc agc tgc cgc cac ttc cct ctg ctg gtc agt agc agc 1296
Ser Pro Asn Thr Ser Cys Arg His Phe Pro Leu Leu Val Ser Ser Ser
            420                 425                 430
ttc tca cgt gtg gac cta ttc aat ggg ctg ttg gga cca gta cag gtc 1344
Phe Ser Arg Val Asp Leu Phe Asn Gly Leu Leu Gly Pro Val Gln Val
        435                 440                 445
act gca ttg tat gtg aca cgc ctt gac aac gtc aca gtg gca cac atg 1392
Thr Ala Leu Tyr Val Thr Arg Leu Asp Asn Val Thr Val Ala His Met
    450                 455                 460
ggc aca atg gat ggg cgt atc ctg cag gtg gag ctg gtc agg tca cta 1440
Gly Thr Met Asp Gly Arg Ile Leu Gln Val Glu Leu Val Arg Ser Leu
465                 470                 475                 480
aac tac ttg ctg tat gtg tcc aac ttc tca ctg ggt gac agt ggg cag 1488
Asn Tyr Leu Leu Tyr Val Ser Asn Phe Ser Leu Gly Asp Ser Gly Gln
                485                 490                 495
ccc gtg cag cgg gat gtc agt cgt ctt ggg gac cac cta ctc ttt gcc 1536
Pro Val Gln Arg Asp Val Ser Arg Leu Gly Asp His Leu Leu Phe Ala
            500                 505                 510
tct ggg gac cag gtt ttc cag gta cct atc cga ggc cct ggc tgc cgc 1584
Ser Gly Asp Gln Val Phe Gln Val Pro Ile Arg Gly Pro Gly Cys Arg
        515                 520                 525
cac ttc ctg acc tgt ggg cgt tgc cta agg gca tgg cat ttc atg ggc 1632
His Phe Leu Thr Cys Gly Arg Cys Leu Arg Ala Trp His Phe Met Gly
    530                 535                 540
tgt ggc tgg tgt ggg aac atg tgc ggc cag cag aag gag tgt cct ggc 1680
Cys Gly Trp Cys Gly Asn Met Cys Gly Gln Gln Lys Glu Cys Pro Gly
545                 550                 555                 560
tcc tgg caa cag gac cac tgc cca cct aag ctt act gag ttc cac ccc 1728
Ser Trp Gln Gln Asp His Cys Pro Pro Lys Leu Thr Glu Phe His Pro
                565                 570                 575
cac agt gga cct cta agg ggc agt aca agg ctg acc ctg tgt ggc tcc 1776
His Ser Gly Pro Leu Arg Gly Ser Thr Arg Leu Thr Leu Cys Gly Ser
            580                 585                 590
aac ttc tac ctt cac cct tct ggt ctg gtg cct gag gga acc cat cag 1824
Asn Phe Tyr Leu His Pro Ser Gly Leu Val Pro Glu Gly Thr His Gln
        595                 600                 605
gtc act gtg ggc caa agt ccc tgc cgg cca ctg ccc aag gac agc tca 1872
Val Thr Val Gly Gln Ser Pro Cys Arg Pro Leu Pro Lys Asp Ser Ser
    610                 615                 620
aaa ctc aga cca gtg ccc cgg aaa gac ttt gta gag gag ttt gag tgt 1920
Lys Leu Arg Pro Val Pro Arg Lys Asp Phe Val Glu Glu Phe Glu Cys
625                 630                 635                 640
```

FIG. 1C-3 Coding Sequence (SEQ ID NO: 1 & 2) cont.

gaa ctg gag ccc ttg ggc acc cag gca gtg ggg cct acc aac gtc agc 1968
Glu Leu Glu Pro Leu Gly Thr Gln Ala Val Gly Pro Thr Asn Val Ser
645 650 655 ctc acc gtg act aac atg cca ccg ggc aag cac ttc cgg gta gac ggc 2016
Leu Thr Val Thr Asn Met Pro Pro Gly Lys His Phe Arg Val Asp Gly
660 665 670 acc tcc gtg ctg aga ggc ttc tct ttc atg gag cca gtg ctg ata gca 2064
Thr Ser Val Leu Arg Gly Phe Ser Phe Met Glu Pro Val Leu Ile Ala
675 680 685 gtg caa ccc ctc ttt ggc cca cgg gca gga ggc acc tgt ctc act ctt 2112
Val Gln Pro Leu Phe Gly Pro Arg Ala Gly Gly Thr Cys Leu Thr Leu
690 695 700 gaa ggc cag agt ctg tct gta ggc acc agc cgg gct gtg ctg gtc aat 2160
Glu Gly Gln Ser Leu Ser Val Gly Thr Ser Arg Ala Val Leu Val Asn
705 710 715 720 ggg act gag tgt ctg cta gca cgg gtc agt gag ggg cag ctt tta tgt 2208
Gly Thr Glu Cys Leu Leu Ala Arg Val Ser Glu Gly Gln Leu Leu Cys
725 730 735 gcc aca ccc cct ggg gcc acg gtg gcc agt gtc ccc ctt agc ctg cag 2256
Ala Thr Pro Pro Gly Ala Thr Val Ala Ser Val Pro Leu Ser Leu Gln
740 745 750 gtg ggg ggt gcc cag gta cct ggt tcc tgg acc ttc cag tac aga gaa 2304
Val Gly Gly Ala Gln Val Pro Gly Ser Trp Thr Phe Gln Tyr Arg Glu
755 760 765 gac cct gtc gtg cta agc atc agc ccc aac tgt ggc tac atc aac tcc 2352
Asp Pro Val Val Leu Ser Ile Ser Pro Asn Cys Gly Tyr Ile Asn Ser
770 775 780 cac atc acc atc tgt ggc cag cat cta act tca gca tgg cac tta gtg 2400
His Ile Thr Ile Cys Gly Gln His Leu Thr Ser Ala Trp His Leu Val
785 790 795 800 ctg tca ttc cat gac ggg ctt agg gca gtg gaa agc agg tgt gag agg 2448
Leu Ser Phe His Asp Gly Leu Arg Ala Val Glu Ser Arg Cys Glu Arg
805 810 815 cag ctt cca gag cag cag ctg tgc cgc ctt cct gaa tat gtg gtc cga 2496
Gln Leu Pro Glu Gln Gln Leu Cys Arg Leu Pro Glu Tyr Val Val Arg
820 825 830 gac ccc cag gga tgg gtg gca ggg aat ctg agt gcc cga ggg gat gga 2544
Asp Pro Gln Gly Trp Val Ala Gly Asn Leu Ser Ala Arg Gly Asp Gly
835 840 845 gct gct ggc ttt aca ctg cct ggc ttt cgc ttc cta ccc cca ccc cat 2592
Ala Ala Gly Phe Thr Leu Pro Gly Phe Arg Phe Leu Pro Pro Pro His
850 855 860 cca ccc agt gcc aac cta gtt cca ctg aag cct gag gag cat gcc att 2640
Pro Pro Ser Ala Asn Leu Val Pro Leu Lys Pro Glu Glu His Ala Ile
865 870 875 880 aag ttt gag tat att ggg ctg ggc gct gtg gct gac tgt gtg ggt atc 2688
Lys Phe Glu Tyr Ile Gly Leu Gly Ala Val Ala Asp Cys Val Gly Ile
885 890 895 aac gtg acc gtg ggt ggt gag agc tgc cag cac gag ttc cgg ggg gac 2736
Asn Val Thr Val Gly Gly Glu Ser Cys Gln His Glu Phe Arg Gly Asp
900 905 910 atg gtt gtc tgc ccc ctg ccc cca tcc ctg cag ctt ggc cag gat ggt 2784
Met Val Val Cys Pro Leu Pro Pro Ser Leu Gln Leu Gly Gln Asp Gly
915 920 925 gcc cca ttg cag gtc tgc gta gat ggt gaa tgt cat atc ctg ggt aga 2832
Ala Pro Leu Gln Val Cys Val Asp Gly Glu Cys His Ile Leu Gly Arg
930 935 940 gtg gtg cgg cca ggg cca gat ggg gtc cca cag agc acg ctc ctt ggt 2880
Val Val Arg Pro Gly Pro Asp Gly Val Pro Gln Ser Thr Leu Leu Gly
945 950 955 960

FIG. 1C-4 Coding Sequence (SEQ ID NO: 1 & 2) cont.

```
atc ctg ctg cct ttg ctg ctg ctt gtg gct gca ctg gcg act gca ctg 2928
Ile Leu Leu Pro Leu Leu Leu Leu Val Ala Ala Leu Ala Thr Ala Leu
                965                 970                 975
gtc ttc agc tac tgg tgg cgg agg aag cag cta gtt ctt cct ccc aac 2976
Val Phe Ser Tyr Trp Trp Arg Arg Lys Gln Leu Val Leu Pro Pro Asn
            980                 985                 990
ctg aat gac ctg gca tcc ctg gac cag act gct gga gcc aca ccc ctg 3024
Leu Asn Asp Leu Ala Ser Leu Asp Gln Thr Ala Gly Ala Thr Pro Leu
        995                 1000                1005
cct att ctg tac tcg ggc tct gac tac aga agt ggc ctt gca ctc cct 3072
Pro Ile Leu Tyr Ser Gly Ser Asp Tyr Arg Ser Gly Leu Ala Leu Pro
    1010                1015                1020
gcc att gat ggt ctg gat tcc acc act tgt gtc cat gga gca tcc ttc 3120
Ala Ile Asp Gly Leu Asp Ser Thr Thr Cys Val His Gly Ala Ser Phe
1025                1030                1035                1040
tcc gat agt gaa gat gaa tcc tgt gtg cca ctg ctg cgg aaa gag tcc 3168
Ser Asp Ser Glu Asp Glu Ser Cys Val Pro Leu Leu Arg Lys Glu Ser
                1045                1050                1055
atc cag cta agg gac ctg gac tct gcg ctc ttg gct gag gtc aag gat 3216
Ile Gln Leu Arg Asp Leu Asp Ser Ala Leu Leu Ala Glu Val Lys Asp
            1060                1065                1070
gtg ctg att ccc cat gag cgg gtg gtc acc cac agt gac cga gtc att 3264
Val Leu Ile Pro His Glu Arg Val Val Thr His Ser Asp Arg Val Ile
        1075                1080                1085
ggc aaa ggc cac ttt gga gtt gtc tac cac gga gaa tac ata gac cag 3312
Gly Lys Gly His Phe Gly Val Val Tyr His Gly Glu Tyr Ile Asp Gln
    1090                1095                1100
gcc cag aat cga atc caa tgt gcc atc aag tca cta agt cgc atc aca 3360
Ala Gln Asn Arg Ile Gln Cys Ala Ile Lys Ser Leu Ser Arg Ile Thr
1105                1110                1115                1120
gag atg cag cag gtg gag gcc ttc ctg cga gag ggg ctg ctc atg cgt 3408
Glu Met Gln Gln Val Glu Ala Phe Leu Arg Glu Gly Leu Leu Met Arg
                1125                1130                1135
ggc ctg aac cac ccg aat gtg ctg gct ctc att ggt atc atg ttg cca 3456
Gly Leu Asn His Pro Asn Val Leu Ala Leu Ile Gly Ile Met Leu Pro
            1140                1145                1150
cct gag ggc ctg ccc cat gtg ctg ctg ccc tat atg tgc cac ggt gac 3504
Pro Glu Gly Leu Pro His Val Leu Leu Pro Tyr Met Cys His Gly Asp
        1155                1160                1165
ctg ctc cag ttc atc cgc tca cct cag cgg aac ccc acc gtg aag gac 3552
Leu Leu Gln Phe Ile Arg Ser Pro Gln Arg Asn Pro Thr Val Lys Asp
    1170                1175                1180
ctc atc agc ttt ggc ctg cag gta gcc cgc ggc atg gag tac ctg gca 3600
Leu Ile Ser Phe Gly Leu Gln Val Ala Arg Gly Met Glu Tyr Leu Ala
1185                1190                1195                1200
gag cag aag ttt gtg cac agg gac ctg gct gcg cgg aac tgc atg ctg 3648
Glu Gln Lys Phe Val His Arg Asp Leu Ala Ala Arg Asn Cys Met Leu
                1205                1210                1215
gac gag tca ttc aca gtc aag gtg gct gac ttt ggt ttg gcc cgc gac 3696
Asp Glu Ser Phe Thr Val Lys Val Ala Asp Phe Gly Leu Ala Arg Asp
            1220                1225                1230
atc ctg gac agg gag tac tat agt gtt caa cag cat cgc cac gct cgc 3744
Ile Leu Asp Arg Glu Tyr Tyr Ser Val Gln Gln His Arg His Ala Arg
        1235                1240                1245
cta cct gtg aag tgg atg gcg ctg gag agc ctg cag acc tat aga ttt 3792
Leu Pro Val Lys Trp Met Ala Leu Glu Ser Leu Gln Thr Tyr Arg Phe
    1250                1255                1260
acc acc aag tct gat gtg tgg tca ttt ggt gtg ctg ctg tgg gaa ctg 3840
Thr Thr Lys Ser Asp Val Trp Ser Phe Gly Val Leu Leu Trp Glu Leu
1265                1270                1275                1280
```

FIG. 1C-5 Coding Sequence (SEQ ID NO: 1 & 2) cont.

```
ctg aca cgg ggt gcc cca cca tac cgc cac att gac cct ttt gac ctt 3888
Leu Thr Arg Gly Ala Pro Pro Tyr Arg His Ile Asp Pro Phe Asp Leu
                1285                1290                1295
acc cac ttc ctg gcc cag ggt cgg cgc ctg ccc cag cct gag tat tgc 3936
Thr His Phe Leu Ala Gln Gly Arg Arg Leu Pro Gln Pro Glu Tyr Cys
            1300                1305                1310
cct gat tct ctg tac caa gtg atg cag caa tgc tgg gag gca gac cca 3984
Pro Asp Ser Leu Tyr Gln Val Met Gln Gln Cys Trp Glu Ala Asp Pro
        1315                1320                1325
gca gtg cga ccc acc ttc aga gta cta gtg ggg gag gtg gag cag ata 4032
Ala Val Arg Pro Thr Phe Arg Val Leu Val Gly Glu Val Glu Gln Ile
    1330                1335                1340
gtg tct gca ctg ctt ggg gac cat tat gtg cag ctg cca gca acc tac 4080
Val Ser Ala Leu Leu Gly Asp His Tyr Val Gln Leu Pro Ala Thr Tyr
1345                1350                1355                1360
atg aac ttg ggc ccc agc acc tcg cat gag atg aat gtg cgt cca gaa 4128
Met Asn Leu Gly Pro Ser Thr Ser His Glu Met Asn Val Arg Pro Glu
                1365                1370                1375
cag ccg cag ttc tca ccc atg cca ggg aat gta cgc cgg ccc cgg cca 4176
Gln Pro Gln Phe Ser Pro Met Pro Gly Asn Val Arg Arg Pro Arg Pro
            1380                1385                1390
ctc tca gag cct cct cgg ccc act                                 4200
Leu Ser Glu Pro Pro Arg Pro Thr
        1395                1400
```

FIG. 2A-1 SEQ ID NO: 3

```
ggatcctcta gggtcccagc tcgcctcgat ggagctcctc ccgccgctgc ctcagtcctt 60
cctgttgctg ctgctgttgc ctgccaagcc cgcggcgggc gaggactggc agtgcccgcg 120
caccccctac gcggcctctc gcgactttga cgtgaagtac gtggtgccca gcttctccgc 180
cggaggcctg gtacaggcca tggtgaccta cgagggcgac agaaatgaga gtgctgtgtt 240
tgtagccata cgcaatcgcc tgcatgtgct tgggcctgac ctgaagtctg tccagagcct 300
ggccacgggc cctgctggag accctggctg ccagacgtgt gcagcctgtg gcccaggacc 360
ccacggccct cccggtgaca cagacacaaa ggtgctggtg ctggatcccg cgctgcctgc 420
gctggtcagt tgtggctcca gcctgcaggg ccgctgcttc ctgcatgacc tagagcccca 480
agggacagcc gtgcatctgg cagcgccagc ctgcctcttc tcagcccacc ataaccggcc 540
cgatgactgc cccgactgtg tggccagccc attgggcacc cgtgtaactg tggttgagca 600
aggccaggcc tcctatttct acgtggcatc ctcactggac gcagccgtgg ctggcagctt 660
cagcccacgc tcagtgtcta tcaggcgtct caaggctgac gcctcgggat tcgcaccggg 720
ctttgtggcg ttgtcagtgc tgcccaagca tcttgtctcc tacagtattg aatacgtgca 780
cagcttccac acgggagcct tcgtatactt cctgactgta cagccggcca gcgtgacaga 840
tgatcctagt gccctgcaca cacgcctggc acggcttagc gccactgagc cagagttggg 900
tgactatcgg gagctggtcc tcgactgcag atttgctcca aaacgcaggc gccggggggc 960
cccagaaggc ggacagccct accctgtgct gcaggtggcc cactccgctc cagtgggtgc 1020
ccaacttgcc actgagctga gcatcgccga gggccaggaa gtactatttg gggtctttgt 1080
gactggcaag gatggtggtc ctggcgtggg ccccaactct gtcgtctgtg ccttccccat 1140
tgacctgctg gacacactaa ttgatgaggg tgtggagcgc tgttgtgaat ccccagtcca 1200
tccaggcctc cggcgaggcc tcgacttctt ccagtcgccc agtttttgcc ccaacccgcc 1260
tggcctggaa gccctcagcc ccaacaccag ctgccgccac ttccctctgc tggtcagtag 1320
cagcttctca cgtgtggacc tattcaatgg gctgttggga ccagtacagg tcactgcatt 1380
gtatgtgaca cgccttgaca acgtcacagt ggcacacatg ggcacaatgg atgggcgtat 1440
cctgcaggtg gagctggtca ggtcactaaa ctacttgctg tatgtgtcca acttctcact 1500
gggtgacagt gggcagcccg tgcagcggga tgtcagtcgt cttggggacc acctactctt 1560
tgcctctggg gaccaggttt tccaggtacc tatccgaggc cctggctgcc gccacttcct 1620
gacctgtggg cgttgcctaa gggcatggca tttcatgggc tgtggctggt gtgggaacat 1680
gtgcggccag cagaaggagt gtcctggctc ctggcaacag gaccactgcc cacctaagct 1740
tactgagttc cacccccaca gtggacctct aaggggcagt acaaggctga ccctgtgtgg 1800
ctccaacttc taccttcacc cttctggtct ggtgcctgag ggaacccatc aggtcactgt 1860
gggccaaagt ccctgccggc cactgcccaa ggacagctca aaactcagac cagtgccccg 1920
gaaagacttt gtagaggagt ttgagtgtga actggagccc ttgggcaccc aggcagtggg 1980
gcctaccaac gtcagcctca ccgtgactaa catgccaccg ggcaagcact tccgggtaga 2040
cggcacctcc gtgctgagag gcttctcttt catggagcca gtgctgatag cagtgcaacc 2100
cctctttggc ccacgggcag gaggcacctg tctcactctt gaaggccaga gtctgtctgt 2160
aggcaccagc cgggctgtgc tggtcaatgg gactgagtgt ctgctagcac gggtcagtga 2220
ggggcagctt ttatgtgcca cacccccctgg ggccacggtg gccagtgtcc cccttagcct 2280
```

FIG. 2A-2 SEQ ID NO: 3 cont.

```
gcaggtgggg ggtgcccagg tacctggttc ctggaccttc cagtacagag aagaccctgt 2340
cgtgctaagc atcagcccca actgtggcta catcaactcc cacatcacca tctgtggcca 2400
gcatctaact tcagcatggc acttagtgct gtcattccat gacgggctta gggcagtgga 2460
aagcaggtgt gagaggcagc ttccagagca gcagctgtgc cgccttcctg aatatgtggt 2520
ccgagacccc cagggatggg tggcagggaa tctgagtgcc cgaggggatg gagctgctgg 2580
ctttacactg cctggctttc gcttcctacc cccaccccat ccacccagtg ccaacctagt 2640
tccactgaag cctgaggagc atgccattaa gtttgagtat attgggctgg gcgctgtggc 2700
tgactgtgtg ggtatcaacg tgaccgtggg tggtgagagc tgccagcacg agttccgggg 2760
ggacatggtt gtctgccccc tgcccccatc cctgcagctt ggccaggatg gtgccccatt 2820
gcaggtctgc gtagatgcac tccctgccat tgatggtctg gattccacca cttgtgtcca 2880
tggagcatcc ttctccgata gtgaagatga atcctgtgtg ccactgctgc ggaaagagtc 2940
catccagcta agggacctgg actctgcgct cttggctgag gtcaaggatg tgctgattcc 3000
ccatgagcgg gtggtcaccc acagtgaccg agtcattggc aaaggccact ttggagttgt 3060
ctaccacgga gaatacatag accaggccca gaatcgaatc caatgtgcca tcaagtcact 3120
aagtcgcatc acagagatgc agcaggtgga ggccttcctg cgagaggggc tgctcatgcg 3180
tggcctgaac cacccgaatg tgctggctct cattggtatc atgttgccac ctgagggcct 3240
gccccatgtg ctgctgccct atatgtgcca cggtgacctg ctccagttca tccgctcacc 3300
tcagcggaac ccccaccgtga aggacctcat cagctttggc ctgcaggtag cccgcggcat 3360
ggagtacctg gcagagcaga agtttgtgca cagggacctg gctgcgcgga actgcatgct 3420
ggacgagtca ttcacagtca aggtggctga ctttggtttg gcccgcgaca tcctggacag 3480
ggagtactat agtgttcaac agcatcgcca cgctcgccta cctgtgaagt ggatggcgct 3540
ggagagcctg cagacctata gatttaccac caagtctgat gtggtaccaa gtgatgcagc 3600
aatgctggga ggcagaccca gcagtgcgac ccaccttcag agtactagtg ggggaggtgg 3660
agcagatagt gtctgcactg cttggggacc attatgtgca gctgccagca acctacatga 3720
acttgagcta accccaaggc tgcctctggg ccatgccagg ccagagcagt ggccctccac 3780
cttgttcctg ccctttaact ttcagaggca ataggtaaat gggcccatta ggtccctcac 3840
tccacagagt gagccagtga gggcagtcct gcaacatgta tttatggagt gcctgctgtg 3900
gaccctgtct tctgggcaca gtggactcag cagtgaccac accaacactg acccttgaac 3960
caataaagga acaaatgact attaaagcac aaaaaaaaaa 4000
```

FIG. 2B-1    SEQ ID NO: 4

```
Met  Glu  Leu  Leu  Pro  Pro  Leu  Pro  Gln  Ser  Phe  Leu  Leu  Leu  Leu  Leu
                    5                        10                       15
Leu  Pro  Ala  Lys  Pro  Ala  Ala  Gly  Glu  Asp  Trp  Gln  Cys  Pro  Arg  Thr
               20                       25                       30
Pro  Tyr  Ala  Ala  Ser  Arg  Asp  Phe  Asp  Val  Lys  Tyr  Val  Val  Pro  Ser
          35                       40                       45
Phe  Ser  Ala  Gly  Gly  Leu  Val  Gln  Ala  Met  Val  Thr  Tyr  Glu  Gly  Asp
     50                       55                       60
Arg  Asn  Glu  Ser  Ala  Val  Phe  Val  Ala  Ile  Arg  Asn  Arg  Leu  His  Val
65                       70                       75                       80
Leu  Gly  Pro  Asp  Leu  Lys  Ser  Val  Gln  Ser  Leu  Ala  Thr  Gly  Pro  Ala
                    85                       90                       95
Gly  Asp  Pro  Gly  Cys  Gln  Thr  Cys  Ala  Ala  Cys  Gly  Pro  Gly  Pro  His
               100                      105                      110
Gly  Pro  Pro  Gly  Asp  Thr  Asp  Thr  Lys  Val  Leu  Val  Leu  Asp  Pro  Ala
          115                      120                      125
Leu  Pro  Ala  Leu  Val  Ser  Cys  Gly  Ser  Ser  Leu  Gln  Gly  Arg  Cys  Phe
     130                      135                      140
Leu  His  Asp  Leu  Glu  Pro  Gln  Gly  Thr  Ala  Val  His  Leu  Ala  Ala  Pro
145                      150                      155                      160
Ala  Cys  Leu  Phe  Ser  Ala  His  His  Asn  Arg  Pro  Asp  Asp  Cys  Pro  Asp
                    165                      170                      175
Cys  Val  Ala  Ser  Pro  Leu  Gly  Thr  Arg  Val  Thr  Val  Val  Glu  Gln  Gly
               180                      185                      190
Gln  Ala  Ser  Tyr  Phe  Tyr  Val  Ala  Ser  Ser  Leu  Asp  Ala  Ala  Val  Ala
          195                      200                      205
Gly  Ser  Phe  Ser  Pro  Arg  Ser  Val  Ser  Ile  Arg  Arg  Leu  Lys  Ala  Asp
     210                      215                      220
Ala  Ser  Gly  Phe  Ala  Pro  Gly  Phe  Val  Ala  Leu  Ser  Val  Leu  Pro  Lys
225                      230                      235                      240
His  Leu  Val  Ser  Tyr  Ser  Ile  Glu  Tyr  Val  His  Ser  Phe  His  Thr  Gly
                    245                      250                      255
Ala  Phe  Val  Tyr  Phe  Leu  Thr  Val  Gln  Pro  Ala  Ser  Val  Thr  Asp  Asp
               260                      265                      270
Pro  Ser  Ala  Leu  His  Thr  Arg  Leu  Ala  Arg  Leu  Ser  Ala  Thr  Glu  Pro
          275                      280                      285
Glu  Leu  Gly  Asp  Tyr  Arg  Glu  Leu  Val  Leu  Asp  Cys  Arg  Phe  Ala  Pro
     290                      295                      300
Lys  Arg  Arg  Arg  Arg  Gly  Ala  Pro  Glu  Gly  Gly  Gln  Pro  Tyr  Pro  Val
305                      310                      315                      320
Leu  Gln  Val  Ala  His  Ser  Ala  Pro  Val  Gly  Ala  Gln  Leu  Ala  Thr  Glu
                    325                      330                      335
Leu  Ser  Ile  Ala  Glu  Gly  Gln  Glu  Val  Leu  Phe  Gly  Val  Phe  Val  Thr
               340                      345                      350
Gly  Lys  Asp  Gly  Gly  Pro  Gly  Val  Gly  Pro  Asn  Ser  Val  Val  Cys  Ala
          355                      360                      365
Phe  Pro  Ile  Asp  Leu  Leu  Asp  Thr  Leu  Ile  Asp  Glu  Gly  Val  Glu  Arg
     370                      375                      380
Cys  Cys  Glu  Ser  Pro  Val  His  Pro  Gly  Leu  Arg  Arg  Gly  Leu  Asp  Phe
385                      390                      395                      400
Phe  Gln  Ser  Pro  Ser  Phe  Cys  Pro  Asn  Pro  Pro  Gly  Leu  Glu  Ala  Leu
                    405                      410                      415
Ser  Pro  Asn  Thr  Ser  Cys  Arg  His  Phe  Pro  Leu  Leu  Val  Ser  Ser  Ser
               420                      425                      430
Phe  Ser  Arg  Val  Asp  Leu  Phe  Asn  Gly  Leu  Leu  Gly  Pro  Val  Gln  Val
          435                      440                      445
Thr  Ala  Leu  Tyr  Val  Thr  Arg  Leu  Asp  Asn  Val  Thr  Val  Ala  His  Met
     450                      455                      460
Gly  Thr  Met  Asp  Gly  Arg  Ile  Leu  Gln  Val  Glu  Leu  Val  Arg  Ser  Leu
465                      470                      475                      480
```

FIG. 2B-2 SEQ ID NO: 4 cont.

| | | | | | | | | | | | | | | | |
|---|---|---|---|---|---|---|---|---|---|---|---|---|---|---|---|
| Asn | Tyr | Leu | Leu | Tyr | Val | Ser | Asn | Phe | Ser | Leu | Gly | Asp | Ser | Gly | Gln |
| | | | | 485 | | | | | 490 | | | | | 495 | |
| Pro | Val | Gln | Arg | Asp | Val | Ser | Arg | Leu | Gly | Asp | His | Leu | Leu | Phe | Ala |
| | | | 500 | | | | | 505 | | | | | 510 | | |
| Ser | Gly | Asp | Gln | Val | Phe | Gln | Val | Pro | Ile | Arg | Gly | Pro | Gly | Cys | Arg |
| | | 515 | | | | | 520 | | | | | 525 | | | |
| His | Phe | Leu | Thr | Cys | Gly | Arg | Cys | Leu | Arg | Ala | Trp | His | Phe | Met | Gly |
| | 530 | | | | | 535 | | | | | 540 | | | | |
| Cys | Gly | Trp | Cys | Gly | Asn | Met | Cys | Gly | Gln | Gln | Lys | Glu | Cys | Pro | Gly |
| 545 | | | | | 550 | | | | | 555 | | | | | 560 |
| Ser | Trp | Gln | Gln | Asp | His | Cys | Pro | Pro | Lys | Leu | Thr | Glu | Phe | His | Pro |
| | | | | 565 | | | | | 570 | | | | | 575 | |
| His | Ser | Gly | Pro | Leu | Arg | Gly | Ser | Thr | Arg | Leu | Thr | Leu | Cys | Gly | Ser |
| | | | 580 | | | | | 585 | | | | | 590 | | |
| Asn | Phe | Tyr | Leu | His | Pro | Ser | Gly | Leu | Val | Pro | Glu | Gly | Thr | His | Gln |
| | | 595 | | | | | 600 | | | | | 605 | | | |
| Val | Thr | Val | Gly | Gln | Ser | Pro | Cys | Arg | Pro | Leu | Pro | Lys | Asp | Ser | Ser |
| | 610 | | | | | 615 | | | | | 620 | | | | |
| Lys | Leu | Arg | Pro | Val | Pro | Arg | Lys | Asp | Phe | Val | Glu | Glu | Phe | Glu | Cys |
| 625 | | | | | 630 | | | | | 635 | | | | | 640 |
| Glu | Leu | Glu | Pro | Leu | Gly | Thr | Gln | Ala | Val | Gly | Pro | Thr | Asn | Val | Ser |
| | | | | 645 | | | | | 650 | | | | | 655 | |
| Leu | Thr | Val | Thr | Asn | Met | Pro | Pro | Gly | Lys | His | Phe | Arg | Val | Asp | Gly |
| | | | 660 | | | | | 665 | | | | | 670 | | |
| Thr | Ser | Val | Leu | Arg | Gly | Phe | Ser | Phe | Met | Glu | Pro | Val | Leu | Ile | Ala |
| | | 675 | | | | | 680 | | | | | 685 | | | |
| Val | Gln | Pro | Leu | Phe | Gly | Pro | Arg | Ala | Gly | Gly | Thr | Cys | Leu | Thr | Leu |
| | 690 | | | | | 695 | | | | | 700 | | | | |
| Glu | Gly | Gln | Ser | Leu | Ser | Val | Gly | Thr | Ser | Arg | Ala | Val | Leu | Val | Asn |
| 705 | | | | | 710 | | | | | 715 | | | | | 720 |
| Gly | Thr | Glu | Cys | Leu | Leu | Ala | Arg | Val | Ser | Glu | Gly | Gln | Leu | Leu | Cys |
| | | | | 725 | | | | | 730 | | | | | 735 | |
| Ala | Thr | Pro | Pro | Gly | Ala | Thr | Val | Ala | Ser | Val | Pro | Leu | Ser | Leu | Gln |
| | | | 740 | | | | | 745 | | | | | 750 | | |
| Val | Gly | Gly | Ala | Gln | Val | Pro | Gly | Ser | Trp | Thr | Phe | Gln | Tyr | Arg | Glu |
| | | 755 | | | | | 760 | | | | | 765 | | | |
| Asp | Pro | Val | Val | Leu | Ser | Ile | Ser | Pro | Asn | Cys | Gly | Tyr | Ile | Asn | Ser |
| | 770 | | | | | 775 | | | | | 780 | | | | |
| His | Ile | Thr | Ile | Cys | Gly | Gln | His | Leu | Thr | Ser | Ala | Trp | His | Leu | Val |
| 785 | | | | | 790 | | | | | 795 | | | | | 800 |
| Leu | Ser | Phe | His | Asp | Gly | Leu | Arg | Ala | Val | Glu | Ser | Arg | Cys | Glu | Arg |
| | | | | 805 | | | | | 810 | | | | | 815 | |
| Gln | Leu | Pro | Glu | Gln | Gln | Leu | Cys | Arg | Leu | Pro | Glu | Tyr | Val | Val | Arg |
| | | | 820 | | | | | 825 | | | | | 830 | | |
| Asp | Pro | Gln | Gly | Trp | Val | Ala | Gly | Asn | Leu | Ser | Ala | Arg | Gly | Asp | Gly |
| | | 835 | | | | | 840 | | | | | 845 | | | |
| Ala | Ala | Gly | Phe | Thr | Leu | Pro | Gly | Phe | Arg | Phe | Leu | Pro | Pro | Pro | His |
| | 850 | | | | | 855 | | | | | 860 | | | | |
| Pro | Pro | Ser | Ala | Asn | Leu | Val | Pro | Leu | Lys | Pro | Glu | Glu | His | Ala | Ile |
| 865 | | | | | 870 | | | | | 875 | | | | | 880 |
| Lys | Phe | Glu | Tyr | Ile | Gly | Leu | Gly | Ala | Val | Ala | Asp | Cys | Val | Gly | Ile |
| | | | | 885 | | | | | 890 | | | | | 895 | |
| Asn | Val | Thr | Val | Gly | Gly | Glu | Ser | Cys | Gln | His | Glu | Phe | Arg | Gly | Asp |
| | | | 900 | | | | | 905 | | | | | 910 | | |
| Met | Val | Val | Cys | Pro | Leu | Pro | Pro | Ser | Leu | Gln | Leu | Gly | Gln | Asp | Gly |
| | | 915 | | | | | 920 | | | | | 925 | | | |
| Ala | Pro | Leu | Gln | Val | Cys | Val | Asp | Ala | Leu | Pro | Ala | Ile | Asp | Gly | Leu |
| | 930 | | | | | 935 | | | | | 940 | | | | |
| Asp | Ser | Thr | Thr | Cys | Val | His | Gly | Ala | Ser | Phe | Ser | Asp | Ser | Glu | Asp |
| 945 | | | | | 950 | | | | | 955 | | | | | 960 |

FIG. 2B-3 SEQ ID NO: 4 cont.

```
Glu Ser Cys Val Pro Leu Leu Arg Lys Glu Ser Ile Gln Leu Arg Asp
                965                 970                 975
Leu Asp Ser Ala Leu Leu Ala Glu Val Lys Asp Val Leu Ile Pro His
            980                 985                 990
Glu Arg Val Val Thr His Ser Asp Arg Val Ile Gly Lys Gly His Phe
        995                1000                1005
Gly Val Val Tyr His Gly Glu Tyr Ile Asp Gln Ala Gln Asn Arg Ile
    1010                1015                1020
Gln Cys Ala Ile Lys Ser Leu Ser Arg Ile Thr Glu Met Gln Gln Val
1025                1030                1035                1040
Glu Ala Phe Leu Arg Glu Gly Leu Leu Met Arg Gly Leu Asn His Pro
                1045                1050                1055
Asn Val Leu Ala Leu Ile Gly Ile Met Leu Pro Pro Glu Gly Leu Pro
            1060                1065                1070
His Val Leu Leu Pro Tyr Met Cys His Gly Asp Leu Leu Gln Phe Ile
        1075                1080                1085
Arg Ser Pro Gln Arg Asn Pro Thr Val Lys Asp Leu Ile Ser Phe Gly
    1090                1095                1100
Leu Gln Val Ala Arg Gly Met Glu Tyr Leu Ala Glu Gln Lys Phe Val
1105                1110                1115                1120
His Arg Asp Leu Ala Ala Arg Asn Cys Met Leu Asp Glu Ser Phe Thr
                1125                1130                1135
Val Lys Val Ala Asp Phe Gly Leu Ala Arg Asp Ile Leu Asp Arg Glu
            1140                1145                1150
Tyr Tyr Ser Val Gln Gln His Arg His Ala Arg Leu Pro Val Lys Trp
        1155                1160                1165
Met Ala Leu Glu Ser Leu Gln Thr Tyr Arg Phe Thr Thr Lys Ser Asp
    1170                1175                1180
Val Val Pro Ser Asp Ala Ala Met Leu Gly Gly Arg Pro Ser Ser Ala
1185                1190                1195                1200
Thr His Leu Gln Ser Thr Ser Gly Gly Gly Gly Ala Asp Ser Val Cys
                1205                1210                1215
Thr Ala Trp Gly Pro Leu Cys Ala Ala Ala Ser Asn Leu His Glu Leu
            1220                1225                1230
Glu Leu Thr Pro Arg Leu Pro Leu Gly His Ala Arg Pro Glu Gln Trp
        1235                1240                1245
Pro Ser Thr Leu Phe Leu Pro Phe Asn Phe Gln Arg Gln
    1250                1255                1260
```

FIG. 2C-1 Coding Sequence (SEQ ID NO: 3 & 4)

```
atg  gag  ctc  ctc  ccg  ccg  ctg  cct  cag  tcc  ttc  ctg  ttg  ctg  ctg  ctg    48
Met  Glu  Leu  Leu  Pro  Pro  Leu  Pro  Gln  Ser  Phe  Leu  Leu  Leu  Leu  Leu
                    5                        10                       15
ttg  cct  gcc  aag  ccc  gcg  gcg  ggc  gag  gac  tgg  cag  tgc  ccg  cgc  acc    96
Leu  Pro  Ala  Lys  Pro  Ala  Ala  Gly  Glu  Asp  Trp  Gln  Cys  Pro  Arg  Thr
               20                       25                       30
ccc  tac  gcg  gcc  tct  cgc  gac  ttt  gac  gtg  aag  tac  gtg  gtg  ccc  agc   144
Pro  Tyr  Ala  Ala  Ser  Arg  Asp  Phe  Asp  Val  Lys  Tyr  Val  Val  Pro  Ser
          35                       40                       45
ttc  tcc  gcc  gga  ggc  ctg  gta  cag  gcc  atg  gtg  acc  tac  gag  ggc  gac   192
Phe  Ser  Ala  Gly  Gly  Leu  Val  Gln  Ala  Met  Val  Thr  Tyr  Glu  Gly  Asp
     50                       55                       60
aga  aat  gag  agt  gct  gtg  ttt  gta  gcc  ata  cgc  aat  cgc  ctg  cat  gtg   240
Arg  Asn  Glu  Ser  Ala  Val  Phe  Val  Ala  Ile  Arg  Asn  Arg  Leu  His  Val
65                       70                       75                       80
ctt  ggg  cct  gac  ctg  aag  tct  gtc  cag  agc  ctg  gcc  acg  ggc  cct  gct   288
Leu  Gly  Pro  Asp  Leu  Lys  Ser  Val  Gln  Ser  Leu  Ala  Thr  Gly  Pro  Ala
                    85                       90                       95
gga  gac  cct  ggc  tgc  cag  acg  tgt  gca  gcc  tgt  ggc  cca  gga  ccc  cac   336
Gly  Asp  Pro  Gly  Cys  Gln  Thr  Cys  Ala  Ala  Cys  Gly  Pro  Gly  Pro  His
               100                      105                      110
ggc  cct  ccc  ggt  gac  aca  gac  aca  aag  gtg  ctg  gtg  ctg  gat  ccc  gcg   384
Gly  Pro  Pro  Gly  Asp  Thr  Asp  Thr  Lys  Val  Leu  Val  Leu  Asp  Pro  Ala
          115                      120                      125
ctg  cct  gcg  ctg  gtc  agt  tgt  ggc  tcc  agc  ctg  cag  ggc  cgc  tgc  ttc   432
Leu  Pro  Ala  Leu  Val  Ser  Cys  Gly  Ser  Ser  Leu  Gln  Gly  Arg  Cys  Phe
     130                      135                      140
ctg  cat  gac  cta  gag  ccc  caa  ggg  aca  gcc  gtg  cat  ctg  gca  gcg  cca   480
Leu  His  Asp  Leu  Glu  Pro  Gln  Gly  Thr  Ala  Val  His  Leu  Ala  Ala  Pro
145                      150                      155                      160
gcc  tgc  ctc  ttc  tca  gcc  cac  cat  aac  cgg  ccc  gat  gac  tgc  ccc  gac   528
Ala  Cys  Leu  Phe  Ser  Ala  His  His  Asn  Arg  Pro  Asp  Asp  Cys  Pro  Asp
                    165                      170                      175
tgt  gtg  gcc  agc  cca  ttg  ggc  acc  cgt  gta  act  gtg  gtt  gag  caa  ggc   576
Cys  Val  Ala  Ser  Pro  Leu  Gly  Thr  Arg  Val  Thr  Val  Val  Glu  Gln  Gly
               180                      185                      190
cag  gcc  tcc  tat  ttc  tac  gtg  gca  tcc  tca  ctg  gac  gca  gcc  gtg  gct   624
Gln  Ala  Ser  Tyr  Phe  Tyr  Val  Ala  Ser  Ser  Leu  Asp  Ala  Ala  Val  Ala
          195                      200                      205
ggc  agc  ttc  agc  cca  cgc  tca  gtg  tct  atc  agg  cgt  ctc  aag  gct  gac   672
Gly  Ser  Phe  Ser  Pro  Arg  Ser  Val  Ser  Ile  Arg  Arg  Leu  Lys  Ala  Asp
     210                      215                      220
gcc  tcg  gga  ttc  gca  ccg  ggc  ttt  gtg  gcg  ttg  tca  gtg  ctg  ccc  aag   720
Ala  Ser  Gly  Phe  Ala  Pro  Gly  Phe  Val  Ala  Leu  Ser  Val  Leu  Pro  Lys
225                      230                      235                      240
cat  ctt  gtc  tcc  tac  agt  att  gaa  tac  gtg  cac  agc  ttc  cac  acg  gga   768
His  Leu  Val  Ser  Tyr  Ser  Ile  Glu  Tyr  Val  His  Ser  Phe  His  Thr  Gly
                    245                      250                      255
gcc  ttc  gta  tac  ttc  ctg  act  gta  cag  ccg  gcc  agc  gtg  aca  gat  gat   816
Ala  Phe  Val  Tyr  Phe  Leu  Thr  Val  Gln  Pro  Ala  Ser  Val  Thr  Asp  Asp
               260                      265                      270
cct  agt  gcc  ctg  cac  aca  cgc  ctg  gca  cgg  ctt  agc  gcc  act  gag  cca   864
Pro  Ser  Ala  Leu  His  Thr  Arg  Leu  Ala  Arg  Leu  Ser  Ala  Thr  Glu  Pro
          275                      280                      285
gag  ttg  ggt  gac  tat  cgg  gag  ctg  gtc  ctc  gac  tgc  aga  ttt  gct  cca   912
Glu  Leu  Gly  Asp  Tyr  Arg  Glu  Leu  Val  Leu  Asp  Cys  Arg  Phe  Ala  Pro
     290                      295                      300
aaa  cgc  agg  cgc  cgg  ggg  gcc  cca  gaa  ggc  gga  cag  ccc  tac  cct  gtg   960
Lys  Arg  Arg  Arg  Arg  Gly  Ala  Pro  Glu  Gly  Gly  Gln  Pro  Tyr  Pro  Val
305                      310                      315                      320
```

FIG. 2C-2 Coding Sequence (SEQ ID NO: 3 & 4) cont.

| | | | | | | | | | | | | | | | | |
|---|---|---|---|---|---|---|---|---|---|---|---|---|---|---|---|---|
| ctg | cag | gtg | gcc | cac | tcc | gct | cca | gtg | ggt | gcc | caa | ctt | gcc | act | gag | 1008 |
| Leu | Gln | Val | Ala | His | Ser | Ala | Pro | Val | Gly | Ala | Gln | Leu | Ala | Thr | Glu | |
| | | | | 325 | | | | | 330 | | | | | 335 | | |
| ctg | agc | atc | gcc | gag | ggc | cag | gaa | gta | cta | ttt | ggg | gtc | ttt | gtg | act | 1056 |
| Leu | Ser | Ile | Ala | Glu | Gly | Gln | Glu | Val | Leu | Phe | Gly | Val | Phe | Val | Thr | |
| | | | 340 | | | | | 345 | | | | | 350 | | | |
| ggc | aag | gat | ggt | ggt | cct | ggc | gtg | ggc | ccc | aac | tct | gtc | gtc | tgt | gcc | 1104 |
| Gly | Lys | Asp | Gly | Gly | Pro | Gly | Val | Gly | Pro | Asn | Ser | Val | Val | Cys | Ala | |
| | | 355 | | | | | 360 | | | | | 365 | | | | |
| ttc | ccc | att | gac | ctg | ctg | gac | aca | cta | att | gat | gag | ggt | gtg | gag | cgc | 1152 |
| Phe | Pro | Ile | Asp | Leu | Leu | Asp | Thr | Leu | Ile | Asp | Glu | Gly | Val | Glu | Arg | |
| | 370 | | | | | 375 | | | | | 380 | | | | | |
| tgt | tgt | gaa | tcc | cca | gtc | cat | cca | ggc | ctc | cgg | cga | ggc | ctc | gac | ttc | 1200 |
| Cys | Cys | Glu | Ser | Pro | Val | His | Pro | Gly | Leu | Arg | Arg | Gly | Leu | Asp | Phe | |
| 385 | | | | | 390 | | | | | 395 | | | | | 400 | |
| ttc | cag | tcg | ccc | agt | ttt | tgc | ccc | aac | ccg | cct | ggc | ctg | gaa | gcc | ctc | 1248 |
| Phe | Gln | Ser | Pro | Ser | Phe | Cys | Pro | Asn | Pro | Pro | Gly | Leu | Glu | Ala | Leu | |
| | | | | 405 | | | | | 410 | | | | | 415 | | |
| agc | ccc | aac | acc | agc | tgc | cgc | cac | ttc | cct | ctg | ctg | gtc | agt | agc | agc | 1296 |
| Ser | Pro | Asn | Thr | Ser | Cys | Arg | His | Phe | Pro | Leu | Leu | Val | Ser | Ser | Ser | |
| | | | 420 | | | | | 425 | | | | | 430 | | | |
| ttc | tca | cgt | gtg | gac | cta | ttc | aat | ggg | ctg | ttg | gga | cca | gta | cag | gtc | 1344 |
| Phe | Ser | Arg | Val | Asp | Leu | Phe | Asn | Gly | Leu | Leu | Gly | Pro | Val | Gln | Val | |
| | | 435 | | | | | 440 | | | | | 445 | | | | |
| act | gca | ttg | tat | gtg | aca | cgc | ctt | gac | aac | gtc | aca | gtg | gca | cac | atg | 1392 |
| Thr | Ala | Leu | Tyr | Val | Thr | Arg | Leu | Asp | Asn | Val | Thr | Val | Ala | His | Met | |
| | 450 | | | | | 455 | | | | | 460 | | | | | |
| ggc | aca | atg | gat | ggg | cgt | atc | ctg | cag | gtg | gag | ctg | gtc | agg | tca | cta | 1440 |
| Gly | Thr | Met | Asp | Gly | Arg | Ile | Leu | Gln | Val | Glu | Leu | Val | Arg | Ser | Leu | |
| 465 | | | | | 470 | | | | | 475 | | | | | 480 | |
| aac | tac | ttg | ctg | tat | gtg | tcc | aac | ttc | tca | ctg | ggt | gac | agt | ggg | cag | 1488 |
| Asn | Tyr | Leu | Leu | Tyr | Val | Ser | Asn | Phe | Ser | Leu | Gly | Asp | Ser | Gly | Gln | |
| | | | | 485 | | | | | 490 | | | | | 495 | | |
| ccc | gtg | cag | cgg | gat | gtc | agt | cgt | ctt | ggg | gac | cac | cta | ctc | ttt | gcc | 1536 |
| Pro | Val | Gln | Arg | Asp | Val | Ser | Arg | Leu | Gly | Asp | His | Leu | Leu | Phe | Ala | |
| | | | 500 | | | | | 505 | | | | | 510 | | | |
| tct | ggg | gac | cag | gtt | ttc | cag | gta | cct | atc | cga | ggc | cct | ggc | tgc | cgc | 1584 |
| Ser | Gly | Asp | Gln | Val | Phe | Gln | Val | Pro | Ile | Arg | Gly | Pro | Gly | Cys | Arg | |
| | | 515 | | | | | 520 | | | | | 525 | | | | |
| cac | ttc | ctg | acc | tgt | ggg | cgt | tgc | cta | agg | gca | tgg | cat | ttc | atg | ggc | 1632 |
| His | Phe | Leu | Thr | Cys | Gly | Arg | Cys | Leu | Arg | Ala | Trp | His | Phe | Met | Gly | |
| | 530 | | | | | 535 | | | | | 540 | | | | | |
| tgt | ggc | tgg | tgt | ggg | aac | atg | tgc | ggc | cag | cag | aag | gag | tgt | cct | ggc | 1680 |
| Cys | Gly | Trp | Cys | Gly | Asn | Met | Cys | Gly | Gln | Gln | Lys | Glu | Cys | Pro | Gly | |
| 545 | | | | | 550 | | | | | 555 | | | | | 560 | |
| tcc | tgg | caa | cag | gac | cac | tgc | cca | cct | aag | ctt | act | gag | ttc | cac | ccc | 1728 |
| Ser | Trp | Gln | Gln | Asp | His | Cys | Pro | Pro | Lys | Leu | Thr | Glu | Phe | His | Pro | |
| | | | | 565 | | | | | 570 | | | | | 575 | | |
| cac | agt | gga | cct | cta | agg | ggc | agt | aca | agg | ctg | acc | ctg | tgt | ggc | tcc | 1776 |
| His | Ser | Gly | Pro | Leu | Arg | Gly | Ser | Thr | Arg | Leu | Thr | Leu | Cys | Gly | Ser | |
| | | | 580 | | | | | 585 | | | | | 590 | | | |
| aac | ttc | tac | ctt | cac | cct | tct | ggt | ctg | gtg | cct | gag | gga | acc | cat | cag | 1824 |
| Asn | Phe | Tyr | Leu | His | Pro | Ser | Gly | Leu | Val | Pro | Glu | Gly | Thr | His | Gln | |
| | | 595 | | | | | 600 | | | | | 605 | | | | |
| gtc | act | gtg | ggc | caa | agt | ccc | tgc | cgg | cca | ctg | ccc | aag | gac | agc | tca | 1872 |
| Val | Thr | Val | Gly | Gln | Ser | Pro | Cys | Arg | Pro | Leu | Pro | Lys | Asp | Ser | Ser | |
| | 610 | | | | | 615 | | | | | 620 | | | | | |
| aaa | ctc | aga | cca | gtg | ccc | cgg | aaa | gac | ttt | gta | gag | gag | ttt | gag | tgt | 1920 |
| Lys | Leu | Arg | Pro | Val | Pro | Arg | Lys | Asp | Phe | Val | Glu | Glu | Phe | Glu | Cys | |
| 625 | | | | | 630 | | | | | 635 | | | | | 640 | |

FIG. 2C-3 Coding Sequence (SEQ ID NO: 3 & 4) cont.

```
gaa   ctg   gag   ccc   ttg   ggc   acc   cag   gca   gtg   ggg   cct   acc   aac   gtc   agc   1968
Glu   Leu   Glu   Pro   Leu   Gly   Thr   Gln   Ala   Val   Gly   Pro   Thr   Asn   Val   Ser
                        645                           650                           655
ctc   acc   gtg   act   aac   atg   cca   ccg   ggc   aag   cac   ttc   cgg   gta   gac   ggc   2016
Leu   Thr   Val   Thr   Asn   Met   Pro   Pro   Gly   Lys   His   Phe   Arg   Val   Asp   Gly
                  660                           665                           670
acc   tcc   gtg   ctg   aga   ggc   ttc   tct   ttc   atg   gag   cca   gtg   ctg   ata   gca   2064
Thr   Ser   Val   Leu   Arg   Gly   Phe   Ser   Phe   Met   Glu   Pro   Val   Leu   Ile   Ala
            675                           680                           685
gtg   caa   ccc   ctc   ttt   ggc   cca   cgg   gca   gga   ggc   acc   tgt   ctc   act   ctt   2112
Val   Gln   Pro   Leu   Phe   Gly   Pro   Arg   Ala   Gly   Gly   Thr   Cys   Leu   Thr   Leu
      690                           695                           700
gaa   ggc   cag   agt   ctg   tct   gta   ggc   acc   agc   cgg   gct   gtg   ctg   gtc   aat   2160
Glu   Gly   Gln   Ser   Leu   Ser   Val   Gly   Thr   Ser   Arg   Ala   Val   Leu   Val   Asn
705                           710                           715                           720
ggg   act   gag   tgt   ctg   cta   gca   cgg   gtc   agt   gag   ggg   cag   ctt   tta   tgt   2208
Gly   Thr   Glu   Cys   Leu   Leu   Ala   Arg   Val   Ser   Glu   Gly   Gln   Leu   Leu   Cys
                        725                           730                           735
gcc   aca   ccc   cct   ggg   gcc   acg   gtg   gcc   agt   gtc   ccc   ctt   agc   ctg   cag   2256
Ala   Thr   Pro   Pro   Gly   Ala   Thr   Val   Ala   Ser   Val   Pro   Leu   Ser   Leu   Gln
                  740                           745                           750
gtg   ggg   ggt   gcc   cag   gta   cct   ggt   tcc   tgg   acc   ttc   cag   tac   aga   gaa   2304
Val   Gly   Gly   Ala   Gln   Val   Pro   Gly   Ser   Trp   Thr   Phe   Gln   Tyr   Arg   Glu
            755                           760                           765
gac   cct   gtc   gtg   cta   agc   atc   agc   ccc   aac   tgt   ggc   tac   atc   aac   tcc   2352
Asp   Pro   Val   Val   Leu   Ser   Ile   Ser   Pro   Asn   Cys   Gly   Tyr   Ile   Asn   Ser
      770                           775                           780
cac   atc   acc   atc   tgt   ggc   cag   cat   cta   act   tca   gca   tgg   cac   tta   gtg   2400
His   Ile   Thr   Ile   Cys   Gly   Gln   His   Leu   Thr   Ser   Ala   Trp   His   Leu   Val
785                           790                           795                           800
ctg   tca   ttc   cat   gac   ggg   ctt   agg   gca   gtg   gaa   agc   agg   tgt   gag   agg   2448
Leu   Ser   Phe   His   Asp   Gly   Leu   Arg   Ala   Val   Glu   Ser   Arg   Cys   Glu   Arg
                        805                           810                           815
cag   ctt   cca   gag   cag   cag   ctg   tgc   cgc   ctt   cct   gaa   tat   gtg   gtc   cga   2496
Gln   Leu   Pro   Glu   Gln   Gln   Leu   Cys   Arg   Leu   Pro   Glu   Tyr   Val   Val   Arg
                  820                           825                           830
gac   ccc   cag   gga   tgg   gtg   gca   ggg   aat   ctg   agt   gcc   cga   ggg   gat   gga   2544
Asp   Pro   Gln   Gly   Trp   Val   Ala   Gly   Asn   Leu   Ser   Ala   Arg   Gly   Asp   Gly
            835                           840                           845
gct   gct   ggc   ttt   aca   ctg   cct   ggc   ttt   cgc   ttc   cta   ccc   cca   ccc   cat   2592
Ala   Ala   Gly   Phe   Thr   Leu   Pro   Gly   Phe   Arg   Phe   Leu   Pro   Pro   Pro   His
      850                           855                           860
cca   ccc   agt   gcc   aac   cta   gtt   cca   ctg   aag   cct   gag   gag   cat   gcc   att   2640
Pro   Pro   Ser   Ala   Asn   Leu   Val   Pro   Leu   Lys   Pro   Glu   Glu   His   Ala   Ile
865                           870                           875                           880
aag   ttt   gag   tat   att   ggg   ctg   ggc   gct   gtg   gct   gac   tgt   gtg   ggt   atc   2688
Lys   Phe   Glu   Tyr   Ile   Gly   Leu   Gly   Ala   Val   Ala   Asp   Cys   Val   Gly   Ile
                        885                           890                           895
aac   gtg   acc   gtg   ggt   ggt   gag   agc   tgc   cag   cac   gag   ttc   cgg   ggg   gac   2736
Asn   Val   Thr   Val   Gly   Gly   Glu   Ser   Cys   Gln   His   Glu   Phe   Arg   Gly   Asp
                  900                           905                           910
atg   gtt   gtc   tgc   ccc   ctg   ccc   cca   tcc   ctg   cag   ctt   ggc   cag   gat   ggt   2784
Met   Val   Val   Cys   Pro   Leu   Pro   Pro   Ser   Leu   Gln   Leu   Gly   Gln   Asp   Gly
            915                           920                           925
gcc   cca   ttg   cag   gtc   tgc   gta   gat   gca   ctc   cct   gcc   att   gat   ggt   ctg   2832
Ala   Pro   Leu   Gln   Val   Cys   Val   Asp   Ala   Leu   Pro   Ala   Ile   Asp   Gly   Leu
      930                           935                           940
gat   tcc   acc   act   tgt   gtc   cat   gga   gca   tcc   ttc   tcc   gat   agt   gaa   gat   2880
Asp   Ser   Thr   Thr   Cys   Val   His   Gly   Ala   Ser   Phe   Ser   Asp   Ser   Glu   Asp
945                           950                           955                           960
```

FIG. 2C-4 Coding Sequence (SEQ ID NO: 3 & 4) cont.

```
gaa tcc tgt gtg cca ctg ctg cgg aaa gag tcc atc cag cta agg gac 2928
Glu Ser Cys Val Pro Leu Leu Arg Lys Glu Ser Ile Gln Leu Arg Asp
                965                 970                 975
ctg gac tct gcg ctc ttg gct gag gtc aag gat gtg ctg att ccc cat 2976
Leu Asp Ser Ala Leu Leu Ala Glu Val Lys Asp Val Leu Ile Pro His
            980                 985                 990
gag cgg gtg gtc acc cac agt gac cga gtc att ggc aaa ggc cac ttt 3024
Glu Arg Val Val Thr His Ser Asp Arg Val Ile Gly Lys Gly His Phe
        995                 1000                1005
gga gtt gtc tac cac gga gaa tac ata gac cag gcc cag aat cga atc 3072
Gly Val Val Tyr His Gly Glu Tyr Ile Asp Gln Ala Gln Asn Arg Ile
    1010                1015                1020
caa tgt gcc atc aag tca cta agt cgc atc aca gag atg cag cag gtg 3120
Gln Cys Ala Ile Lys Ser Leu Ser Arg Ile Thr Glu Met Gln Gln Val
1025                1030                1035                1040
gag gcc ttc ctg cga gag ggg ctg ctc atg cgt ggc ctg aac cac ccg 3168
Glu Ala Phe Leu Arg Glu Gly Leu Leu Met Arg Gly Leu Asn His Pro
                1045                1050                1055
aat gtg ctg gct ctc att ggt atc atg ttg cca cct gag ggc ctg ccc 3216
Asn Val Leu Ala Leu Ile Gly Ile Met Leu Pro Pro Glu Gly Leu Pro
            1060                1065                1070
cat gtg ctg ctg ccc tat atg tgc cac ggt gac ctg ctc cag ttc atc 3264
His Val Leu Leu Pro Tyr Met Cys His Gly Asp Leu Leu Gln Phe Ile
        1075                1080                1085
cgc tca cct cag cgg aac ccc acc gtg aag gac ctc atc agc ttt ggc 3312
Arg Ser Pro Gln Arg Asn Pro Thr Val Lys Asp Leu Ile Ser Phe Gly
    1090                1095                1100
ctg cag gta gcc cgc ggc atg gag tac ctg gca gag cag aag ttt gtg 3360
Leu Gln Val Ala Arg Gly Met Glu Tyr Leu Ala Glu Gln Lys Phe Val
1105                1110                1115                1120
cac agg gac ctg gct gcg cgg aac tgc atg ctg gac gag tca ttc aca 3408
His Arg Asp Leu Ala Ala Arg Asn Cys Met Leu Asp Glu Ser Phe Thr
                1125                1130                1135
gtc aag gtg gct gac ttt ggt ttg gcc cgc gac atc ctg gac agg gag 3456
Val Lys Val Ala Asp Phe Gly Leu Ala Arg Asp Ile Leu Asp Arg Glu
            1140                1145                1150
tac tat agt gtt caa cag cat cgc cac gct cgc cta cct gtg aag tgg 3504
Tyr Tyr Ser Val Gln Gln His Arg His Ala Arg Leu Pro Val Lys Trp
        1155                1160                1165
atg gcg ctg gag agc ctg cag acc tat aga ttt acc acc aag tct gat 3552
Met Ala Leu Glu Ser Leu Gln Thr Tyr Arg Phe Thr Thr Lys Ser Asp
    1170                1175                1180
gtg gta cca agt gat gca gca atg ctg gga ggc aga ccc agc agt gcg 3600
Val Val Pro Ser Asp Ala Ala Met Leu Gly Gly Arg Pro Ser Ser Ala
1185                1190                1195                1200
acc cac ctt cag agt act agt ggg gga ggt gga gca gat agt gtc tgc 3648
Thr His Leu Gln Ser Thr Ser Gly Gly Gly Gly Ala Asp Ser Val Cys
                1205                1210                1215
act gct tgg gga cca tta tgt gca gct gcc agc aac cta cat gaa ctt 3696
Thr Ala Trp Gly Pro Leu Cys Ala Ala Ala Ser Asn Leu His Glu Leu
            1220                1225                1230
gag cta acc cca agg ctg cct ctg ggc cat gcc agg cca gag cag tgg 3744
Glu Leu Thr Pro Arg Leu Pro Leu Gly His Ala Arg Pro Glu Gln Trp
        1235                1240                1245
ccc tcc acc ttg ttc ctg ccc ttt aac ttt cag agg caa             3783
Pro Ser Thr Leu Phe Leu Pro Phe Asn Phe Gln Arg Gln
    1250                1255                1260
```

FIG. 3A-1 SEQ ID NO: 5

```
ggatcctcta gggtcccagc tcgcctcgat ggagctcctc ccgccgctgc ctcagtcctt 60
cctgttgctg ctgctgttgc ctgccaagcc cgcggcgggc gaggactggc agtgcccgcg 120
caccccctac gcggcctctc gcgactttga cgtgaagtac gtggtgccca gcttctccgc 180
cggaggcctg gtacaggcca tggtgaccta cgagggcgac agaaatgaga gtgctgtgtt 240
tgtagccata cgcaatcgcc tgcatgtgct tgggcctgac ctgaagtctg tccagagcct 300
ggccacgggc cctgctggag accctggctg ccagacgtgt gcagcctgtg gcccaggacc 360
ccacggccct cccggtgaca cagacacaaa ggtgctggtg ctggatcccg cgctgcctgc 420
gctggtcagt tgtggctcca gcctgcaggg ccgctgcttc ctgcatgacc tagagcccca 480
agggacagcc gtgcatctgg cagcgccagc ctgcctcttc tcagcccacc ataaccggcc 540
cgatgactgc cccgactgtg tggccagccc attgggcacc cgtgtaactg tggttgagca 600
aggccaggcc tcctatttct acgtggcatc ctcactggac gcagccgtgg ctggcagctt 660
cagcccacgc tcagtgtcta tcaggcgtct caaggctgac gcctcgggat tcgcaccggg 720
ctttgtggcg ttgtcagtgc tgcccaagca tcttgtctcc tacagtattg aatacgtgca 780
cagcttccac acgggagcct tcgtatactt cctgactgta cagccggcca gcgtgacaga 840
tgatcctagt gccctgcaca cacgcctggc acggcttagc gccactgagc cagagttggg 900
tgactatcgg gagctggtcc tcgactgcag atttgctcca aaacgcaggc gccgggggc 960
cccagaaggc ggacagccct accctgtgct gcaggtggcc cactccgctc cagtgggtgc 1020
ccaacttgcc actgagctga gcatcgccga gggccaggaa gtactatttg ggtctttgt 1080
gactggcaag gatggtggtc ctggcgtggg ccccaactct gtcgtctgtg ccttccccat 1140
tgacctgctg gacacactaa ttgatgaggg tgtggagcgc tgttgtgaat ccccagtcca 1200
tccaggcctc cggcgaggcc tcgacttctt ccagtcgccc agtttttgcc ccaacccgcc 1260
tggcctggaa gccctcagcc ccaacaccag ctgccgccac ttccctctgc tggtcagtag 1320
cagcttctca cgtgtggacc tattcaatgg gctgttggga ccagtacagg tcactgcatt 1380
gtatgtgaca cgccttgaca acgtcacagt ggcacacatg ggcacaatgg atgggcgtat 1440
cctgcaggtg gagctggtca ggtcactaaa ctacttgctg tatgtgtcca acttctcact 1500
gggtgacagt gggcagcccg tgcagcggga tgtcagtcgt cttggggacc acctactctt 1560
tgcctctggg gaccaggttt tccaggtacc tatccgaggc cctggctgcc gccacttcct 1620
gacctgtggg cgttgcctaa gggcatggca tttcatgggc tgtggctggt gtgggaacat 1680
gtgcggccag cagaaggagt gtcctggctc ctggcaacag gaccactgcc cacctaagct 1740
tactgagttc cacccccaca gtggacctct aaggggcagt acaaggctga ccctgtgtgg 1800
ctccaacttc taccttcacc cttctggtct ggtgcctgag ggaacccatc aggtcactgt 1860
gggccaaagt ccctgccggc cactgcccaa ggacagctca aaactcagac cagtgccccg 1920
gaaagacttt gtagaggagt ttgagtgtga actggagccc ttgggcaccc aggcagtggg 1980
gcctaccaac gtcagcctca ccgtgactaa catgccaccg ggcaagcact tccgggtaga 2040
cggcacctcc gtgctgagag gcttctcttt catggagcca gtgctgatag cagtgcaacc 2100
cctctttggc ccacgggcag gaggcacctg tctcactctt gaaggccaga gtctgtctgt 2160
aggcaccagc cgggctgtgc tggtcaatgg gactgagtgt ctgctagcac gggtcagtga 2220
ggggcagctt ttatgtgcca cacccctgg ggccacggtg gccagtgtcc cccttagcct 2280
```

FIG. 3A-2 SEQ ID NO: 5 cont.

```
gcaggtgggg ggtgcccagg tacctggttc ctggaccttc cagtacagag aagaccctgt 2340
cgtgctaagc atcagcccca actgtggcta catcaactcc cacatcacca tctgtggcca 2400
gcatctaact tcagcatggc acttagtgct gtcattccat gacgggctta gggcagtgga 2460
aagcaggtgt gagaggcagc ttccagagca gcagctgtgc cgccttcctg aatatgtggt 2520
ccgagacccc cagggatggg tggcagggaa tctgagtgcc cgaggggatg gagctgctgg 2580
ctttacactg cctggctttc gcttcctacc cccaccccat ccacccagtg ccaacctagt 2640
tccactgaag cctgaggagc atgccattaa gtttgagctt ggccaggatg gtgccccatt 2700
gcaggtctgc gtagatgcac tccctgccat tgatggtctg gattccacca cttgtgtcca 2760
tggagcatcc ttctccgata gtgaagatga atcctgtgtg ccactgctgc ggaaagagtc 2820
catccagcta agggacctgg actctgcgct cttggctgag gtcaaggatg tgctgattcc 2880
ccatgagcgg gtggtcaccc acagtgaccg agtcattggc aaaggccact ttggagttgt 2940
ctaccacgga gaatacatag accaggccca gaatcgaatc caatgtgcca tcaagtcact 3000
aagtcgcatc acagagatgc agcaggtgga ggccttcctg cgagaggggc tgctcatgcg 3060
tggcctgaac cacccgaatg tgctggctct cattggtatc atgttgccac ctgagggcct 3120
gccccatgtg ctgctgccct atatgtgcca cggtgacctg ctccagttca tccgctcacc 3180
tcagcggaac cccaccgtga aggacctcat cagctttggc ctgcaggtag cccgcggcat 3240
ggagtacctg gcagagcaga agtttgtgca cagggacctg gctgcgcgga actgcatgct 3300
ggacgagtca ttcacagtca aggtggctga ctttggtttg gcccgcgaca tcctggacag 3360
ggagtactat agtgttcaac agcatcgcca cgctcgccta cctgtgaagt ggatggcgct 3420
ggagagcctg cagacctata gatttaccac caagtctgat gtggtaccaa gtgatgcagc 3480
aatgctggga ggcagaccca gcagtgcgac ccaccttcag agtactagtg gggaggtgg 3540
agcagatagt gtctgcactg cttggggacc attatgtgca gctgccagca acctacatga 3600
acttgagcta accccaaggc tgcctctggg ccatgccagg ccagagcagt ggccctccac 3660
cttgttcctg ccctttaact ttcagaggca ataggtaaat gggcccatta ggtccctcac 3720
tccacagagt gagccagtga gggcagtcct gcaacatgta tttatggagt gcctgctgtg 3780
gaccctgtct tctgggcaca gtggactcag cagtgaccac accaacactg acccttgaac 3840
caataaagga acaaatgact attaaagcac aaaaaaaaaa 3880
```

FIG. 3B-1 SEQ ID NO: 6

Met Glu Leu Leu Pro Pro Leu Pro Gln Ser Phe Leu Leu Leu Leu Leu
5 10 15
Leu Pro Ala Lys Pro Ala Ala Gly Glu Asp Trp Gln Cys Pro Arg Thr
20 25 30
Pro Tyr Ala Ala Ser Arg Asp Phe Asp Val Lys Tyr Val Val Pro Ser
35 40 45
Phe Ser Ala Gly Gly Leu Val Gln Ala Met Val Thr Tyr Glu Gly Asp
50 55 60
Arg Asn Glu Ser Ala Val Phe Val Ala Ile Arg Asn Arg Leu His Val
65 70 75 80
Leu Gly Pro Asp Leu Lys Ser Val Gln Ser Leu Ala Thr Gly Pro Ala
85 90 95
Gly Asp Pro Gly Cys Gln Thr Cys Ala Ala Cys Gly Pro Gly Pro His
100 105 110
Gly Pro Pro Gly Asp Thr Asp Thr Lys Val Leu Val Leu Asp Pro Ala
115 120 125
Leu Pro Ala Leu Val Ser Cys Gly Ser Ser Leu Gln Gly Arg Cys Phe
130 135 140
Leu His Asp Leu Glu Pro Gln Gly Thr Ala Val His Leu Ala Ala Pro
145 150 155 160
Ala Cys Leu Phe Ser Ala His His Asn Arg Pro Asp Asp Cys Pro Asp
165 170 175
Cys Val Ala Ser Pro Leu Gly Thr Arg Val Thr Val Val Glu Gln Gly
180 185 190
Gln Ala Ser Tyr Phe Tyr Val Ala Ser Ser Leu Asp Ala Ala Val Ala
195 200 205
Gly Ser Phe Ser Pro Arg Ser Val Ser Ile Arg Arg Leu Lys Ala Asp
210 215 220
Ala Ser Gly Phe Ala Pro Gly Phe Val Ala Leu Ser Val Leu Pro Lys
225 230 235 240
His Leu Val Ser Tyr Ser Ile Glu Tyr Val His Ser Phe His Thr Gly
245 250 255
Ala Phe Val Tyr Phe Leu Thr Val Gln Pro Ala Ser Val Thr Asp Asp
260 265 270
Pro Ser Ala Leu His Thr Arg Leu Ala Arg Leu Ser Ala Thr Glu Pro
275 280 285
Glu Leu Gly Asp Tyr Arg Glu Leu Val Leu Asp Cys Arg Phe Ala Pro
290 295 300
Lys Arg Arg Arg Arg Gly Ala Pro Glu Gly Gly Gln Pro Tyr Pro Val
305 310 315 320
Leu Gln Val Ala His Ser Ala Pro Val Gly Ala Gln Leu Ala Thr Glu
325 330 335
Leu Ser Ile Ala Glu Gly Gln Glu Val Leu Phe Gly Val Phe Val Thr
340 345 350
Gly Lys Asp Gly Gly Pro Gly Val Gly Pro Asn Ser Val Val Cys Ala
355 360 365
Phe Pro Ile Asp Leu Leu Asp Thr Leu Ile Asp Glu Gly Val Glu Arg
370 375 380
Cys Cys Glu Ser Pro Val His Pro Gly Leu Arg Arg Gly Leu Asp Phe
385 390 395 400
Phe Gln Ser Pro Ser Phe Cys Pro Asn Pro Pro Gly Leu Glu Ala Leu
405 410 415
Ser Pro Asn Thr Ser Cys Arg His Phe Pro Leu Leu Val Ser Ser Ser
420 425 430
Phe Ser Arg Val Asp Leu Phe Asn Gly Leu Leu Gly Pro Val Gln Val
435 440 445
Thr Ala Leu Tyr Val Thr Arg Leu Asp Asn Val Thr Val Ala His Met
450 455 460
Gly Thr Met Asp Gly Arg Ile Leu Gln Val Glu Leu Val Arg Ser Leu
465 470 475 480

FIG. 3B-2 SEQ ID NO: 6 cont.

| | | | | | | | | | | | | | | | |
|---|---|---|---|---|---|---|---|---|---|---|---|---|---|---|---|
| Asn | Tyr | Leu | Leu | Tyr | Val | Ser | Asn | Phe | Ser | Leu | Gly | Asp | Ser | Gly | Gln |
| | | | | 485 | | | | | 490 | | | | | 495 | |
| Pro | Val | Gln | Arg | Asp | Val | Ser | Arg | Leu | Gly | Asp | His | Leu | Leu | Phe | Ala |
| | | | 500 | | | | | 505 | | | | | 510 | | |
| Ser | Gly | Asp | Gln | Val | Phe | Gln | Val | Pro | Ile | Arg | Gly | Pro | Gly | Cys | Arg |
| | | 515 | | | | | 520 | | | | | 525 | | | |
| His | Phe | Leu | Thr | Cys | Gly | Arg | Cys | Leu | Arg | Ala | Trp | His | Phe | Met | Gly |
| | 530 | | | | | 535 | | | | | 540 | | | | |
| Cys | Gly | Trp | Cys | Gly | Asn | Met | Cys | Gly | Gln | Gln | Lys | Glu | Cys | Pro | Gly |
| 545 | | | | | 550 | | | | | 555 | | | | | 560 |
| Ser | Trp | Gln | Gln | Asp | His | Cys | Pro | Pro | Lys | Leu | Thr | Glu | Phe | His | Pro |
| | | | | 565 | | | | | 570 | | | | | 575 | |
| His | Ser | Gly | Pro | Leu | Arg | Gly | Ser | Thr | Arg | Leu | Thr | Leu | Cys | Gly | Ser |
| | | | 580 | | | | | 585 | | | | | 590 | | |
| Asn | Phe | Tyr | Leu | His | Pro | Ser | Gly | Leu | Val | Pro | Glu | Gly | Thr | His | Gln |
| | | 595 | | | | | 600 | | | | | 605 | | | |
| Val | Thr | Val | Gly | Gln | Ser | Pro | Cys | Arg | Pro | Leu | Pro | Lys | Asp | Ser | Ser |
| | 610 | | | | | 615 | | | | | 620 | | | | |
| Lys | Leu | Arg | Pro | Val | Pro | Arg | Lys | Asp | Phe | Val | Glu | Glu | Phe | Glu | Cys |
| 625 | | | | | 630 | | | | | 635 | | | | | 640 |
| Glu | Leu | Glu | Pro | Leu | Gly | Thr | Gln | Ala | Val | Gly | Pro | Thr | Asn | Val | Ser |
| | | | | 645 | | | | | 650 | | | | | 655 | |
| Leu | Thr | Val | Thr | Asn | Met | Pro | Pro | Gly | Lys | His | Phe | Arg | Val | Asp | Gly |
| | | | 660 | | | | | 665 | | | | | 670 | | |
| Thr | Ser | Val | Leu | Arg | Gly | Phe | Ser | Phe | Met | Glu | Pro | Val | Leu | Ile | Ala |
| | | 675 | | | | | 680 | | | | | 685 | | | |
| Val | Gln | Pro | Leu | Phe | Gly | Pro | Arg | Ala | Gly | Gly | Thr | Cys | Leu | Thr | Leu |
| | 690 | | | | | 695 | | | | | 700 | | | | |
| Glu | Gly | Gln | Ser | Leu | Ser | Val | Gly | Thr | Ser | Arg | Ala | Val | Leu | Val | Asn |
| 705 | | | | | 710 | | | | | 715 | | | | | 720 |
| Gly | Thr | Glu | Cys | Leu | Leu | Ala | Arg | Val | Ser | Glu | Gly | Gln | Leu | Leu | Cys |
| | | | | 725 | | | | | 730 | | | | | 735 | |
| Ala | Thr | Pro | Pro | Gly | Ala | Thr | Val | Ala | Ser | Val | Pro | Leu | Ser | Leu | Gln |
| | | | 740 | | | | | 745 | | | | | 750 | | |
| Val | Gly | Gly | Ala | Gln | Val | Pro | Gly | Ser | Trp | Thr | Phe | Gln | Tyr | Arg | Glu |
| | | 755 | | | | | 760 | | | | | 765 | | | |
| Asp | Pro | Val | Val | Leu | Ser | Ile | Ser | Pro | Asn | Cys | Gly | Tyr | Ile | Asn | Ser |
| | 770 | | | | | 775 | | | | | 780 | | | | |
| His | Ile | Thr | Ile | Cys | Gly | Gln | His | Leu | Thr | Ser | Ala | Trp | His | Leu | Val |
| 785 | | | | | 790 | | | | | 795 | | | | | 800 |
| Leu | Ser | Phe | His | Asp | Gly | Leu | Arg | Ala | Val | Glu | Ser | Arg | Cys | Glu | Arg |
| | | | | 805 | | | | | 810 | | | | | 815 | |
| Gln | Leu | Pro | Glu | Gln | Gln | Leu | Cys | Arg | Leu | Pro | Glu | Tyr | Val | Val | Arg |
| | | | 820 | | | | | 825 | | | | | 830 | | |
| Asp | Pro | Gln | Gly | Trp | Val | Ala | Gly | Asn | Leu | Ser | Ala | Arg | Gly | Asp | Gly |
| | | 835 | | | | | 840 | | | | | 845 | | | |
| Ala | Ala | Gly | Phe | Thr | Leu | Pro | Gly | Phe | Arg | Phe | Leu | Pro | Pro | Pro | His |
| | 850 | | | | | 855 | | | | | 860 | | | | |
| Pro | Pro | Ser | Ala | Asn | Leu | Val | Pro | Leu | Lys | Pro | Glu | Glu | His | Ala | Ile |
| 865 | | | | | 870 | | | | | 875 | | | | | 880 |
| Lys | Phe | Glu | Leu | Gly | Gln | Asp | Gly | Ala | Pro | Leu | Gln | Val | Cys | Val | Asp |
| | | | | 885 | | | | | 890 | | | | | 895 | |
| Ala | Leu | Pro | Ala | Ile | Asp | Gly | Leu | Asp | Ser | Thr | Thr | Cys | Val | His | Gly |
| | | | 900 | | | | | 905 | | | | | 910 | | |
| Ala | Ser | Phe | Ser | Asp | Ser | Glu | Asp | Glu | Ser | Cys | Val | Pro | Leu | Leu | Arg |
| | | 915 | | | | | 920 | | | | | 925 | | | |
| Lys | Glu | Ser | Ile | Gln | Leu | Arg | Asp | Leu | Asp | Ser | Ala | Leu | Leu | Ala | Glu |
| | 930 | | | | | 935 | | | | | 940 | | | | |
| Val | Lys | Asp | Val | Leu | Ile | Pro | His | Glu | Arg | Val | Val | Thr | His | Ser | Asp |
| 945 | | | | | 950 | | | | | 955 | | | | | 960 |

FIG. 3B-3 SEQ ID NO: 6 cont.

```
Arg Val Ile Gly Lys Gly His Phe Gly Val Val Tyr His Gly Glu Tyr
                965                 970                 975
Ile Asp Gln Ala Gln Asn Arg Ile Gln Cys Ala Ile Lys Ser Leu Ser
            980                 985                 990
Arg Ile Thr Glu Met Gln Gln Val Glu Ala Phe Leu Arg Glu Gly Leu
        995                 1000                1005
Leu Met Arg Gly Leu Asn His Pro Asn Val Leu Ala Leu Ile Gly Ile
    1010                1015                1020
Met Leu Pro Pro Glu Gly Leu Pro His Val Leu Leu Pro Tyr Met Cys
1025                1030                1035                1040
His Gly Asp Leu Leu Gln Phe Ile Arg Ser Pro Gln Arg Asn Pro Thr
                1045                1050                1055
Val Lys Asp Leu Ile Ser Phe Gly Leu Gln Val Ala Arg Gly Met Glu
            1060                1065                1070
Tyr Leu Ala Glu Gln Lys Phe Val His Arg Asp Leu Ala Ala Arg Asn
        1075                1080                1085
Cys Met Leu Asp Glu Ser Phe Thr Val Lys Val Ala Asp Phe Gly Leu
    1090                1095                1100
Ala Arg Asp Ile Leu Asp Arg Glu Tyr Tyr Ser Val Gln Gln His Arg
1105                1110                1115                1120
His Ala Arg Leu Pro Val Lys Trp Met Ala Leu Glu Ser Leu Gln Thr
                1125                1130                1135
Tyr Arg Phe Thr Thr Lys Ser Asp Val Val Pro Ser Asp Ala Ala Met
            1140                1145                1150
Leu Gly Gly Arg Pro Ser Ser Ala Thr His Leu Gln Ser Thr Ser Gly
        1155                1160                1165
Gly Gly Gly Ala Asp Ser Val Cys Thr Ala Trp Gly Pro Leu Cys Ala
    1170                1175                1180
Ala Ala Ser Asn Leu His Glu Leu Glu Leu Thr Pro Arg Leu Pro Leu
1185                1190                1195                1200
Gly His Ala Arg Pro Glu Gln Trp Pro Ser Thr Leu Phe Leu Pro Phe
                1205                1210                1215
Asn Phe Gln Arg Gln
            1220
```

FIG. 3C-1 Coding Sequence (SEQ ID NO: 5 & 6)

| | | | | | | | | | | | | | | | | |
|---|---|---|---|---|---|---|---|---|---|---|---|---|---|---|---|---|
| atg | gag | ctc | ctc | ccg | ccg | ctg | cct | cag | tcc | ttc | ctg | ttg | ctg | ctg | ctg | 48 |
| Met | Glu | Leu | Leu | Pro | Pro | Leu | Pro | Gln | Ser | Phe | Leu | Leu | Leu | Leu | Leu | |
| | | | | 5 | | | | | 10 | | | | | 15 | | |
| ttg | cct | gcc | aag | ccc | gcg | gcg | ggc | gag | gac | tgg | cag | tgc | ccg | cgc | acc | 96 |
| Leu | Pro | Ala | Lys | Pro | Ala | Ala | Gly | Glu | Asp | Trp | Gln | Cys | Pro | Arg | Thr | |
| | | | 20 | | | | | 25 | | | | | 30 | | | |
| ccc | tac | gcg | gcc | tct | cgc | gac | ttt | gac | gtg | aag | tac | gtg | gtg | ccc | agc | 144 |
| Pro | Tyr | Ala | Ala | Ser | Arg | Asp | Phe | Asp | Val | Lys | Tyr | Val | Val | Pro | Ser | |
| | | 35 | | | | | 40 | | | | | 45 | | | | |
| ttc | tcc | gcc | gga | ggc | ctg | gta | cag | gcc | atg | gtg | acc | tac | gag | ggc | gac | 192 |
| Phe | Ser | Ala | Gly | Gly | Leu | Val | Gln | Ala | Met | Val | Thr | Tyr | Glu | Gly | Asp | |
| | 50 | | | | | 55 | | | | | 60 | | | | | |
| aga | aat | gag | agt | gct | gtg | ttt | gta | gcc | ata | cgc | aat | cgc | ctg | cat | gtg | 240 |
| Arg | Asn | Glu | Ser | Ala | Val | Phe | Val | Ala | Ile | Arg | Asn | Arg | Leu | His | Val | |
| 65 | | | | | 70 | | | | | 75 | | | | | 80 | |
| ctt | ggg | cct | gac | ctg | aag | tct | gtc | cag | agc | ctg | gcc | acg | ggc | cct | gct | 288 |
| Leu | Gly | Pro | Asp | Leu | Lys | Ser | Val | Gln | Ser | Leu | Ala | Thr | Gly | Pro | Ala | |
| | | | | 85 | | | | | 90 | | | | | 95 | | |
| gga | gac | cct | ggc | tgc | cag | acg | tgt | gca | gcc | tgt | ggc | cca | gga | ccc | cac | 336 |
| Gly | Asp | Pro | Gly | Cys | Gln | Thr | Cys | Ala | Ala | Cys | Gly | Pro | Gly | Pro | His | |
| | | | 100 | | | | | 105 | | | | | 110 | | | |
| ggc | cct | ccc | ggt | gac | aca | gac | aca | aag | gtg | ctg | gtg | ctg | gat | ccc | gcg | 384 |
| Gly | Pro | Pro | Gly | Asp | Thr | Asp | Thr | Lys | Val | Leu | Val | Leu | Asp | Pro | Ala | |
| | | 115 | | | | | 120 | | | | | 125 | | | | |
| ctg | cct | gcg | ctg | gtc | agt | tgt | ggc | tcc | agc | ctg | cag | ggc | cgc | tgc | ttc | 432 |
| Leu | Pro | Ala | Leu | Val | Ser | Cys | Gly | Ser | Ser | Leu | Gln | Gly | Arg | Cys | Phe | |
| | 130 | | | | | 135 | | | | | 140 | | | | | |
| ctg | cat | gac | cta | gag | ccc | caa | ggg | aca | gcc | gtg | cat | ctg | gca | gcg | cca | 480 |
| Leu | His | Asp | Leu | Glu | Pro | Gln | Gly | Thr | Ala | Val | His | Leu | Ala | Ala | Pro | |
| 145 | | | | | 150 | | | | | 155 | | | | | 160 | |
| gcc | tgc | ctc | ttc | tca | gcc | cac | cat | aac | cgg | ccc | gat | gac | tgc | ccc | gac | 528 |
| Ala | Cys | Leu | Phe | Ser | Ala | His | His | Asn | Arg | Pro | Asp | Asp | Cys | Pro | Asp | |
| | | | | 165 | | | | | 170 | | | | | 175 | | |
| tgt | gtg | gcc | agc | cca | ttg | ggc | acc | cgt | gta | act | gtg | gtt | gag | caa | ggc | 576 |
| Cys | Val | Ala | Ser | Pro | Leu | Gly | Thr | Arg | Val | Thr | Val | Val | Glu | Gln | Gly | |
| | | | 180 | | | | | 185 | | | | | 190 | | | |
| cag | gcc | tcc | tat | ttc | tac | gtg | gca | tcc | tca | ctg | gac | gca | gcc | gtg | gct | 624 |
| Gln | Ala | Ser | Tyr | Phe | Tyr | Val | Ala | Ser | Ser | Leu | Asp | Ala | Ala | Val | Ala | |
| | | 195 | | | | | 200 | | | | | 205 | | | | |
| ggc | agc | ttc | agc | cca | cgc | tca | gtg | tct | atc | agg | cgt | ctc | aag | gct | gac | 672 |
| Gly | Ser | Phe | Ser | Pro | Arg | Ser | Val | Ser | Ile | Arg | Arg | Leu | Lys | Ala | Asp | |
| | 210 | | | | | 215 | | | | | 220 | | | | | |
| gcc | tcg | gga | ttc | gca | ccg | ggc | ttt | gtg | gcg | ttg | tca | gtg | ctg | ccc | aag | 720 |
| Ala | Ser | Gly | Phe | Ala | Pro | Gly | Phe | Val | Ala | Leu | Ser | Val | Leu | Pro | Lys | |
| 225 | | | | | 230 | | | | | 235 | | | | | 240 | |
| cat | ctt | gtc | tcc | tac | agt | att | gaa | tac | gtg | cac | agc | ttc | cac | acg | gga | 768 |
| His | Leu | Val | Ser | Tyr | Ser | Ile | Glu | Tyr | Val | His | Ser | Phe | His | Thr | Gly | |
| | | | | 245 | | | | | 250 | | | | | 255 | | |
| gcc | ttc | gta | tac | ttc | ctg | act | gta | cag | ccg | gcc | agc | gtg | aca | gat | gat | 816 |
| Ala | Phe | Val | Tyr | Phe | Leu | Thr | Val | Gln | Pro | Ala | Ser | Val | Thr | Asp | Asp | |
| | | | 260 | | | | | 265 | | | | | 270 | | | |
| cct | agt | gcc | ctg | cac | aca | cgc | ctg | gca | cgg | ctt | agc | gcc | act | gag | cca | 864 |
| Pro | Ser | Ala | Leu | His | Thr | Arg | Leu | Ala | Arg | Leu | Ser | Ala | Thr | Glu | Pro | |
| | | 275 | | | | | 280 | | | | | 285 | | | | |
| gag | ttg | ggt | gac | tat | cgg | gag | ctg | gtc | ctc | gac | tgc | aga | ttt | gct | cca | 912 |
| Glu | Leu | Gly | Asp | Tyr | Arg | Glu | Leu | Val | Leu | Asp | Cys | Arg | Phe | Ala | Pro | |
| | 290 | | | | | 295 | | | | | 300 | | | | | |
| aaa | cgc | agg | cgc | cgg | ggg | gcc | cca | gaa | ggc | gga | cag | ccc | tac | cct | gtg | 960 |
| Lys | Arg | Arg | Arg | Arg | Gly | Ala | Pro | Glu | Gly | Gly | Gln | Pro | Tyr | Pro | Val | |
| 305 | | | | | 310 | | | | | 315 | | | | | 320 | |

FIG. 3C-2 Coding Sequence (SEQ ID NO: 5 & 6) cont.

```
ctg cag gtg gcc cac tcc gct cca gtg ggt gcc caa ctt gcc act gag 1008
Leu Gln Val Ala His Ser Ala Pro Val Gly Ala Gln Leu Ala Thr Glu
                325                 330                 335
ctg agc atc gcc gag ggc cag gaa gta cta ttt ggg gtc ttt gtg act 1056
Leu Ser Ile Ala Glu Gly Gln Glu Val Leu Phe Gly Val Phe Val Thr
            340                 345                 350
ggc aag gat ggt ggt cct ggc gtg ggc ccc aac tct gtc gtc tgt gcc 1104
Gly Lys Asp Gly Gly Pro Gly Val Gly Pro Asn Ser Val Val Cys Ala
        355                 360                 365
ttc ccc att gac ctg ctg gac aca cta att gat gag ggt gtg gag cgc 1152
Phe Pro Ile Asp Leu Leu Asp Thr Leu Ile Asp Glu Gly Val Glu Arg
    370                 375                 380
tgt tgt gaa tcc cca gtc cat cca ggc ctc cgg cga ggc ctc gac ttc 1200
Cys Cys Glu Ser Pro Val His Pro Gly Leu Arg Arg Gly Leu Asp Phe
385                 390                 395                 400
ttc cag tcg ccc agt ttt tgc ccc aac ccg cct ggc ctg gaa gcc ctc 1248
Phe Gln Ser Pro Ser Phe Cys Pro Asn Pro Pro Gly Leu Glu Ala Leu
                405                 410                 415
agc ccc aac acc agc tgc cgc cac ttc cct ctg ctg gtc agt agc agc 1296
Ser Pro Asn Thr Ser Cys Arg His Phe Pro Leu Leu Val Ser Ser Ser
            420                 425                 430
ttc tca cgt gtg gac cta ttc aat ggg ctg ttg gga cca gta cag gtc 1344
Phe Ser Arg Val Asp Leu Phe Asn Gly Leu Leu Gly Pro Val Gln Val
        435                 440                 445
act gca ttg tat gtg aca cgc ctt gac aac gtc aca gtg gca cac atg 1392
Thr Ala Leu Tyr Val Thr Arg Leu Asp Asn Val Thr Val Ala His Met
    450                 455                 460
ggc aca atg gat ggg cgt atc ctg cag gtg gag ctg gtc agg tca cta 1440
Gly Thr Met Asp Gly Arg Ile Leu Gln Val Glu Leu Val Arg Ser Leu
465                 470                 475                 480
aac tac ttg ctg tat gtg tcc aac ttc tca ctg ggt gac agt ggg cag 1488
Asn Tyr Leu Leu Tyr Val Ser Asn Phe Ser Leu Gly Asp Ser Gly Gln
                485                 490                 495
ccc gtg cag cgg gat gtc agt cgt ctt ggg gac cac cta ctc ttt gcc 1536
Pro Val Gln Arg Asp Val Ser Arg Leu Gly Asp His Leu Leu Phe Ala
            500                 505                 510
tct ggg gac cag gtt ttc cag gta cct atc cga ggc cct ggc tgc cgc 1584
Ser Gly Asp Gln Val Phe Gln Val Pro Ile Arg Gly Pro Gly Cys Arg
        515                 520                 525
cac ttc ctg acc tgt ggg cgt tgc cta agg gca tgg cat ttc atg ggc 1632
His Phe Leu Thr Cys Gly Arg Cys Leu Arg Ala Trp His Phe Met Gly
    530                 535                 540
tgt ggc tgg tgt ggg aac atg tgc ggc cag cag aag gag tgt cct ggc 1680
Cys Gly Trp Cys Gly Asn Met Cys Gly Gln Gln Lys Glu Cys Pro Gly
545                 550                 555                 560
tcc tgg caa cag gac cac tgc cca cct aag ctt act gag ttc cac ccc 1728
Ser Trp Gln Gln Asp His Cys Pro Pro Lys Leu Thr Glu Phe His Pro
                565                 570                 575
cac agt gga cct cta agg ggc agt aca agg ctg acc ctg tgt ggc tcc 1776
His Ser Gly Pro Leu Arg Gly Ser Thr Arg Leu Thr Leu Cys Gly Ser
            580                 585                 590
aac ttc tac ctt cac cct tct ggt ctg gtg cct gag gga acc cat cag 1824
Asn Phe Tyr Leu His Pro Ser Gly Leu Val Pro Glu Gly Thr His Gln
        595                 600                 605
gtc act gtg ggc caa agt ccc tgc cgg cca ctg ccc aag gac agc tca 1872
Val Thr Val Gly Gln Ser Pro Cys Arg Pro Leu Pro Lys Asp Ser Ser
    610                 615                 620
aaa ctc aga cca gtg ccc cgg aaa gac ttt gta gag gag ttt gag tgt 1920
Lys Leu Arg Pro Val Pro Arg Lys Asp Phe Val Glu Glu Phe Glu Cys
625                 630                 635                 640
```

FIG. 3C-3 Coding Sequence (SEQ ID NO: 5 & 6) cont.

```
gaa ctg gag ccc ttg ggc acc cag gca gtg ggg cct acc aac gtc agc 1968
Glu Leu Glu Pro Leu Gly Thr Gln Ala Val Gly Pro Thr Asn Val Ser
                645                 650                 655
ctc acc gtg act aac atg cca ccg ggc aag cac ttc cgg gta gac ggc 2016
Leu Thr Val Thr Asn Met Pro Pro Gly Lys His Phe Arg Val Asp Gly
            660                 665                 670
acc tcc gtg ctg aga ggc ttc tct ttc atg gag cca gtg ctg ata gca 2064
Thr Ser Val Leu Arg Gly Phe Ser Phe Met Glu Pro Val Leu Ile Ala
        675                 680                 685
gtg caa ccc ctc ttt ggc cca cgg gca gga ggc acc tgt ctc act ctt 2112
Val Gln Pro Leu Phe Gly Pro Arg Ala Gly Gly Thr Cys Leu Thr Leu
    690                 695                 700
gaa ggc cag agt ctg tct gta ggc acc agc cgg gct gtg ctg gtc aat 2160
Glu Gly Gln Ser Leu Ser Val Gly Thr Ser Arg Ala Val Leu Val Asn
705                 710                 715                 720
ggg act gag tgt ctg cta gca cgg gtc agt gag ggg cag ctt tta tgt 2208
Gly Thr Glu Cys Leu Leu Ala Arg Val Ser Glu Gly Gln Leu Leu Cys
                725                 730                 735
gcc aca ccc cct ggg gcc acg gtg gcc agt gtc ccc ctt agc ctg cag 2256
Ala Thr Pro Pro Gly Ala Thr Val Ala Ser Val Pro Leu Ser Leu Gln
            740                 745                 750
gtg ggg ggt gcc cag gta cct ggt tcc tgg acc ttc cag tac aga gaa 2304
Val Gly Gly Ala Gln Val Pro Gly Ser Trp Thr Phe Gln Tyr Arg Glu
        755                 760                 765
gac cct gtc gtg cta agc atc agc ccc aac tgt ggc tac atc aac tcc 2352
Asp Pro Val Val Leu Ser Ile Ser Pro Asn Cys Gly Tyr Ile Asn Ser
    770                 775                 780
cac atc acc atc tgt ggc cag cat cta act tca gca tgg cac tta gtg 2400
His Ile Thr Ile Cys Gly Gln His Leu Thr Ser Ala Trp His Leu Val
785                 790                 795                 800
ctg tca ttc cat gac ggg ctt agg gca gtg gaa agc agg tgt gag agg 2448
Leu Ser Phe His Asp Gly Leu Arg Ala Val Glu Ser Arg Cys Glu Arg
                805                 810                 815
cag ctt cca gag cag cag ctg tgc cgc ctt cct gaa tat gtg gtc cga 2496
Gln Leu Pro Glu Gln Gln Leu Cys Arg Leu Pro Glu Tyr Val Val Arg
            820                 825                 830
gac ccc cag gga tgg gtg gca ggg aat ctg agt gcc cga ggg gat gga 2544
Asp Pro Gln Gly Trp Val Ala Gly Asn Leu Ser Ala Arg Gly Asp Gly
        835                 840                 845
gct gct ggc ttt aca ctg cct ggc ttt cgc ttc cta ccc cca ccc cat 2592
Ala Ala Gly Phe Thr Leu Pro Gly Phe Arg Phe Leu Pro Pro Pro His
    850                 855                 860
cca ccc agt gcc aac cta gtt cca ctg aag cct gag gag cat gcc att 2640
Pro Pro Ser Ala Asn Leu Val Pro Leu Lys Pro Glu Glu His Ala Ile
865                 870                 875                 880
aag ttt gag ctt ggc cag gat ggt gcc cca ttg cag gtc tgc gta gat 2688
Lys Phe Glu Leu Gly Gln Asp Gly Ala Pro Leu Gln Val Cys Val Asp
                885                 890                 895
gca ctc cct gcc att gat ggt ctg gat tcc acc act tgt gtc cat gga 2736
Ala Leu Pro Ala Ile Asp Gly Leu Asp Ser Thr Thr Cys Val His Gly
            900                 905                 910
gca tcc ttc tcc gat agt gaa gat gaa tcc tgt gtg cca ctg ctg cgg 2784
Ala Ser Phe Ser Asp Ser Glu Asp Glu Ser Cys Val Pro Leu Leu Arg
        915                 920                 925
aaa gag tcc atc cag cta agg gac ctg gac tct gcg ctc ttg gct gag 2832
Lys Glu Ser Ile Gln Leu Arg Asp Leu Asp Ser Ala Leu Leu Ala Glu
    930                 935                 940
gtc aag gat gtg ctg att ccc cat gag cgg gtg gtc acc cac agt gac 2880
Val Lys Asp Val Leu Ile Pro His Glu Arg Val Val Thr His Ser Asp
945                 950                 955                 960
```

FIG. 3C-4 Coding Sequence (SEQ ID NO: 5 & 6) cont.

```
cga  gtc  att  ggc  aaa  ggc  cac  ttt  gga  gtt  gtc  tac  cac  gga  gaa  tac  2928
Arg  Val  Ile  Gly  Lys  Gly  His  Phe  Gly  Val  Val  Tyr  His  Gly  Glu  Tyr
                    965                      970                      975
ata  gac  cag  gcc  cag  aat  cga  atc  caa  tgt  gcc  atc  aag  tca  cta  agt  2976
Ile  Asp  Gln  Ala  Gln  Asn  Arg  Ile  Gln  Cys  Ala  Ile  Lys  Ser  Leu  Ser
               980                      985                      990
cgc  atc  aca  gag  atg  cag  cag  gtg  gag  gcc  ttc  ctg  cga  gag  ggg  ctg  3024
Arg  Ile  Thr  Glu  Met  Gln  Gln  Val  Glu  Ala  Phe  Leu  Arg  Glu  Gly  Leu
          995                      1000                     1005
ctc  atg  cgt  ggc  ctg  aac  cac  ccg  aat  gtg  ctg  gct  ctc  att  ggt  atc  3072
Leu  Met  Arg  Gly  Leu  Asn  His  Pro  Asn  Val  Leu  Ala  Leu  Ile  Gly  Ile
     1010                     1015                     1020
atg  ttg  cca  cct  gag  ggc  ctg  ccc  cat  gtg  ctg  ctg  ccc  tat  atg  tgc  3120
Met  Leu  Pro  Pro  Glu  Gly  Leu  Pro  His  Val  Leu  Leu  Pro  Tyr  Met  Cys
1025                     1030                     1035                     1040
cac  ggt  gac  ctg  ctc  cag  ttc  atc  cgc  tca  cct  cag  cgg  aac  ccc  acc  3168
His  Gly  Asp  Leu  Leu  Gln  Phe  Ile  Arg  Ser  Pro  Gln  Arg  Asn  Pro  Thr
                    1045                     1050                     1055
gtg  aag  gac  ctc  atc  agc  ttt  ggc  ctg  cag  gta  gcc  cgc  ggc  atg  gag  3216
Val  Lys  Asp  Leu  Ile  Ser  Phe  Gly  Leu  Gln  Val  Ala  Arg  Gly  Met  Glu
               1060                     1065                     1070
tac  ctg  gca  gag  cag  aag  ttt  gtg  cac  agg  gac  ctg  gct  gcg  cgg  aac  3264
Tyr  Leu  Ala  Glu  Gln  Lys  Phe  Val  His  Arg  Asp  Leu  Ala  Ala  Arg  Asn
          1075                     1080                     1085
tgc  atg  ctg  gac  gag  tca  ttc  aca  gtc  aag  gtg  gct  gac  ttt  ggt  ttg  3312
Cys  Met  Leu  Asp  Glu  Ser  Phe  Thr  Val  Lys  Val  Ala  Asp  Phe  Gly  Leu
     1090                     1095                     1100
gcc  cgc  gac  atc  ctg  gac  agg  gag  tac  tat  agt  gtt  caa  cag  cat  cgc  3360
Ala  Arg  Asp  Ile  Leu  Asp  Arg  Glu  Tyr  Tyr  Ser  Val  Gln  Gln  His  Arg
1105                     1110                     1115                     1120
cac  gct  cgc  cta  cct  gtg  aag  tgg  atg  gcg  ctg  gag  agc  ctg  cag  acc  3408
His  Ala  Arg  Leu  Pro  Val  Lys  Trp  Met  Ala  Leu  Glu  Ser  Leu  Gln  Thr
                    1125                     1130                     1135
tat  aga  ttt  acc  acc  aag  tct  gat  gtg  gta  cca  agt  gat  gca  gca  atg  3456
Tyr  Arg  Phe  Thr  Thr  Lys  Ser  Asp  Val  Val  Pro  Ser  Asp  Ala  Ala  Met
               1140                     1145                     1150
ctg  gga  ggc  aga  ccc  agc  agt  gcg  acc  cac  ctt  cag  agt  act  agt  ggg  3504
Leu  Gly  Gly  Arg  Pro  Ser  Ser  Ala  Thr  His  Leu  Gln  Ser  Thr  Ser  Gly
          1155                     1160                     1165
gga  ggt  gga  gca  gat  agt  gtc  tgc  act  gct  tgg  gga  cca  tta  tgt  gca  3552
Gly  Gly  Gly  Ala  Asp  Ser  Val  Cys  Thr  Ala  Trp  Gly  Pro  Leu  Cys  Ala
     1170                     1175                     1180
gct  gcc  agc  aac  cta  cat  gaa  ctt  gag  cta  acc  cca  agg  ctg  cct  ctg  3600
Ala  Ala  Ser  Asn  Leu  His  Glu  Leu  Glu  Leu  Thr  Pro  Arg  Leu  Pro  Leu
1185                     1190                     1195                     1200
ggc  cat  gcc  agg  cca  gag  cag  tgg  ccc  tcc  acc  ttg  ttc  ctg  ccc  ttt  3648
Gly  His  Ala  Arg  Pro  Glu  Gln  Trp  Pro  Ser  Thr  Leu  Phe  Leu  Pro  Phe
                    1205                     1210                     1215
aac  ttt  cag  agg  caa                                                       3663
Asn  Phe  Gln  Arg  Gln
               1220
```

FIG. 4A-1 SEQ ID NO: 7

```
GGATCCTCTA GGGTCCCAGC TCGCCTCGAT GGAGCTCCTC CCGCCGCTGC CTCAGTCCTT   60
CCTGTTGCTG CTGCTGTTGC CTGCCAAGCC CGCGGCGGGC GAGGACTGGC AGTGCCCGCG  120
CACCCCCTAC GCGGCCTCTC GCGACTTTGA CGTGAAGTAC GTGGTGCCCA GCTTCTCCGC  180
CGGAGGCCTG GTACAGGCCA TGGTGACCTA CGAGGGCGAC AGAAATGAGA GTGCTGTGTT  240
TGTAGCCATA CGCAATCGCC TGCATGTGCT TGGGCCTGAC CTGAAGTCTG TCCAGAGCCT  300
GGCCACGGGC CCTGCTGGAG ACCCTGGCTG CCAGACGTGT GCAGCCTGTG GCCCAGGACC  360
CCACGGCCCT CCCGGTGACA CAGACACAAA GGTGCTGGTG CTGGATCCCG CGCTGCCTGC  420
GCTGGTCAGT TGTGGCTCCA GCCTGCAGGG CCGCTGCTTC CTGCATGACC TAGAGCCCCA  480
AGGGACAGCC GTGCATCTGG CAGCGCCAGC CTGCCTCTTC TCAGCCCACC ATAACCGGCC  540
CGATGACTGC CCCGACTGTG TGGCCAGCCC ATTGGGCACC CGTGTAACTG TGGTTGAGCA  600
AGGCCAGGCC TCCTATTTCT ACGTGGCATC CTCACTGGAC GCAGCCGTGG CTGGCAGCTT  660
CAGCCCACGC TCAGTGTCTA TCAGGCGTCT CAAGGCTGAC GCCTCGGGAT TCGCACCGGG  720
CTTTGTGGCG TTGTCAGTGC TGCCCAAGCA TCTTGTCTCC TACAGTATTG AATACGTGCA  780
CAGCTTCCAC ACGGGAGCCT TCGTATACTT CCTGACTGTA CAGCCGGCCA GCGTGACAGA  840
TGATCCTAGT GCCCTGCACA CACGCCTGGC ACGGCTTAGC GCCACTGAGC CAGAGTTGGG  900
TGACTATCGG GAGCTGGTCC TCGACTGCAG ATTTGCTCCA AAACGCAGGC GCCGGGGGGC  960
CCCAGAAGGC GGACAGCCCT ACCCTGTGCT GCAGGTGGCC CACTCCGCTC CAGTGGGTGC 1020
CCAACTTGCC ACTGAGCTGA GCATCGCCGA GGGCCAGGAA GTACTATTTG GGGTCTTTGT 1080
GACTGGCAAG GATGGTGGTC CTGGCGTGGG CCCCAACTCT GTCGTCTGTG CCTTCCCCAT 1140
TGACCTGCTG GACACACTAA TTGATGAGGG TGTGGAGCGC TGTTGTGAAT CCCCAGTCCA 1200
TCCAGGCCTC CGGCGAGGCC TCGACTTCTT CCAGTCGCCC AGTTTTTGCC CCAACCCGCC 1260
TGGCCTGGAA GCCCTCAGCC CCAACACCAG CTGCCGCCAC TTCCCTCTGC TGGTCAGTAG 1320
CAGCTTCTCA CGTGTGGACC TATTCAATGG GCTGTTGGGA CCAGTACAGG TCACTGCATT 1380
GTATGTGACA CGCCTTGACA ACGTCACAGT GGCACACATG GGCACAATGG ATGGGCGTAT 1440
CCTGCAGGTG GAGCTGGTCA GGTCACTAAA CTACTTGCTG TATGTGTCCA ACTTCTCACT 1500
GGGTGACAGT GGGCAGCCCG TGCAGCGGGA TGTCAGTCGT CTTGGGGACC ACCTACTCTT 1560
TGCCTCTGGG GACCAGGTTT TCCAGGTACC TATCCGAGGC CCTGGCTGCC GCCACTTCCT 1620
GACCTGTGGG CGTTGCCTAA GGGCATGGCA TTTCATGGGC TGTGGCTGGT GTGGGAACAT 1680
GTGCGGCCAG CAGAAGGAGT GTCCTGGCTC CTGGCAACAG GACCACTGCC CACCTAAGCT 1740
TACTGAGTTC CACCCCCACA GTGGACCTCT AAGGGGCAGT ACAAGGCTGA CCCTGTGTGG 1800
CTCCAACTTC TACCTTCACC CTTCTGGTCT GGTGCCTGAG GGAACCCATC AGGTCACTGT 1860
GGGCCAAAGT CCCTGCCGGC CACTGCCCAA GGACAGCTCA AAACTCAGAC CAGTGCCCCG 1920
GAAAGACTTT GTAGAGGAGT TTGAGTGTGA ACTGGAGCCC TTGGGCACCC AGGCAGTGGG 1980
GCCTACCAAC GTCAGCCTCA CCGTGACTAA CATGCCACCG GGCAAGCACT TCCGGGTAGA 2040
CGGCACCTCC GTGCTGAGAG GCTTCTCTTT CATGGAGCCA GTGCTGATAG CAGTGCAACC 2100
CCTCTTTGGC CCACGGGCAG GAGGCACCTG TCTCACTCTT GAAGGCCAGA GTCTGTCTGT 2160
AGGCACCAGC CGGGCTGTGC TGGTCAATGG GACTGAGTGT CTGCTAGCAC GGGTCAGTGA 2220
GGGGCAGCTT TTATGTGCCA CACCCCCTGG GGCCACGGTG GCCAGTGTCC CCCTTAGCCT 2280
```

FIG. 4A-2 SEQ ID NO: 7 cont.

```
GCAGGTGGGG  GGTGCCCAGG  TACCTGGTTC  CTGGACCTTC  CAGTACAGAG  AAGACCCTGT  2340
CGTGCTAAGC  ATCAGCCCCA  ACTGTGGCTA  CATCAACTCC  CACATCACCA  TCTGTGGCCA  2400
GCATCTAACT  TCAGCATGGC  ACTTAGTGCT  GTCATTCCAT  GACGGGCTTA  GGGCAGTGGA  2460
AAGCAGGTGT  GAGAGGCAGC  TTCCAGAGCA  GCAGCTGTGC  CGCCTTCCTG  AATATGTGGT  2520
CCGAGACCCC  CAGGGATGGG  TGGCAGGGAA  TCTGAGTGCC  CGAGGGGATG  GAGCTGCTGG  2580
CTTTACACTG  CCTGGCTTTC  GCTTCCTACC  CCCACCCCAT  CCACCCAGTG  CCAACCTAGT  2640
TCCACTGAAG  CCTGAGGAGC  ATGCCATTAA  GTTTGAGGTC  TGCGTAGATG  CACTCCCTGC  2700
CATTGATGGT  CTGGATTCCA  CCACTTGTGT  CCATGGAGCA  TCCTTCTCCG  ATAGTGAAGA  2760
TGAATCCTGT  GTGCCACTGC  TGCGGAAAGA  GTCCATCCAG  CTAAGGGACC  TGGACTCTGC  2820
GCTCTTGGCT  GAGGTCAAGG  ATGTGCTGAT  TCCCCATGAG  CGGGTGGTCA  CCCACAGTGA  2880
CCGAGTCATT  GGCAAAGGCC  ACTTTGGAGT  TGTCTACCAC  GGAGAATACA  TAGACCAGGC  2940
CCAGAATCGA  ATCCAATGTG  CCATCAAGTC  ACTAAGTCGC  ATCACAGAGA  TGCAGCAGGT  3000
GGAGGCCTTC  CTGCGAGAGG  GGCTGCTCAT  GCGTGGCCTG  AACCACCCGA  ATGTGCTGGC  3060
TCTCATTGGT  ATCATGTTGC  CACCTGAGGG  CCTGCCCCAT  GTGCTGCTGC  CCTATATGTG  3120
CCACGGTGAC  CTGCTCCAGT  TCATCCGCTC  ACCTCAGCGG  AACCCCACCG  TGAAGGACCT  3180
CATCAGCTTT  GGCCTGCAGG  TAGCCCGCGG  CATGGAGTAC  CTGGCAGAGC  AGAAGTTTGT  3240
GCACAGGGAC  CTGGCTGCGC  GGAACTGCAT  GCTGGACGAG  TCATTCACAG  TCAAGGTGGC  3300
TGACTTTGGT  TTGGCCCGCG  ACATCCTGGA  CAGGGAGTAC  TATAGTGTTC  AACAGCATCG  3360
CCACGCTCGC  CTACCTGTGA  AGTGGATGGC  GCTGGAGAGC  CTGCAGACCT  ATAGATTTAC  3420
CACCAAGTCT  GATGTGGTAC  CAAGTGATGC  AGCAATGCTG  GGAGGCAGAC  CCAGCAGTGC  3480
GACCCACCTT  CAGAGTACTA  GTGGGGGAGG  TGGAGCAGAT  AGTGTCTGCA  CTGCTTGGGG  3540
ACCATTATGT  GCAGCTGCCA  GCAACCTACA  TGAACTTGAG  CTAACCCCAA  GGCTGCCTCT  3600
GGGCCATGCC  AGGCCAGAGC  AGTGGCCCTC  CACCTTGTTC  CTGCCCTTTA  ACTTTCAGAG  3660
GCAATAGGTA  AATGGGCCCA  TTAGGTCCCT  CACTCCACAG  AGTGAGCCAG  TGAGGGCAGT  3720
CCTGCAACAT  GTATTTATGG  AGTGCCTGCT  GTGGACCCTG  TCTTCTGGGC  ACAGTGGACT  3780
CAGCAGTGAC  CACACCAACA  CTGACCCTTG  AACCAATAAA  GGAACAAATG  ACTATTAAAG  3840
CACAAAAAAA  AAA                                                        3853
```

FIG. 4B-1 SEQ ID NO: 8

| Met | Glu | Leu | Leu | Pro | Pro | Leu | Pro | Gln | Ser | Phe | Leu | Leu | Leu | Leu | Leu |
|---|---|---|---|---|---|---|---|---|---|---|---|---|---|---|---|
| | | | | 5 | | | | | 10 | | | | | 15 | |
| Leu | Pro | Ala | Lys | Pro | Ala | Ala | Gly | Glu | Asp | Trp | Gln | Cys | Pro | Arg | Thr |
| | | | 20 | | | | | 25 | | | | | 30 | | |
| Pro | Tyr | Ala | Ala | Ser | Arg | Asp | Phe | Asp | Val | Lys | Tyr | Val | Val | Pro | Ser |
| | | 35 | | | | | 40 | | | | | 45 | | | |
| Phe | Ser | Ala | Gly | Gly | Leu | Val | Gln | Ala | Met | Val | Thr | Tyr | Glu | Gly | Asp |
| | 50 | | | | | 55 | | | | | 60 | | | | |
| Arg | Asn | Glu | Ser | Ala | Val | Phe | Val | Ala | Ile | Arg | Asn | Arg | Leu | His | Val |
| 65 | | | | | 70 | | | | | 75 | | | | | 80 |
| Leu | Gly | Pro | Asp | Leu | Lys | Ser | Val | Gln | Ser | Leu | Ala | Thr | Gly | Pro | Ala |
| | | | | 85 | | | | | 90 | | | | | 95 | |
| Gly | Asp | Pro | Gly | Cys | Gln | Thr | Cys | Ala | Ala | Cys | Gly | Pro | Gly | Pro | His |
| | | | 100 | | | | | 105 | | | | | 110 | | |
| Gly | Pro | Pro | Gly | Asp | Thr | Asp | Thr | Lys | Val | Leu | Val | Leu | Asp | Pro | Ala |
| | | 115 | | | | | 120 | | | | | 125 | | | |
| Leu | Pro | Ala | Leu | Val | Ser | Cys | Gly | Ser | Ser | Leu | Gln | Gly | Arg | Cys | Phe |
| | 130 | | | | | 135 | | | | | 140 | | | | |
| Leu | His | Asp | Leu | Glu | Pro | Gln | Gly | Thr | Ala | Val | His | Leu | Ala | Ala | Pro |
| 145 | | | | | 150 | | | | | 155 | | | | | 160 |
| Ala | Cys | Leu | Phe | Ser | Ala | His | His | Asn | Arg | Pro | Asp | Asp | Cys | Pro | Asp |
| | | | | 165 | | | | | 170 | | | | | 175 | |
| Cys | Val | Ala | Ser | Pro | Leu | Gly | Thr | Arg | Val | Thr | Val | Val | Glu | Gln | Gly |
| | | | 180 | | | | | 185 | | | | | 190 | | |
| Gln | Ala | Ser | Tyr | Phe | Tyr | Val | Ala | Ser | Ser | Leu | Asp | Ala | Ala | Val | Ala |
| | | 195 | | | | | 200 | | | | | 205 | | | |
| Gly | Ser | Phe | Ser | Pro | Arg | Ser | Val | Ser | Ile | Arg | Arg | Leu | Lys | Ala | Asp |
| | 210 | | | | | 215 | | | | | 220 | | | | |
| Ala | Ser | Gly | Phe | Ala | Pro | Gly | Phe | Val | Ala | Leu | Ser | Val | Leu | Pro | Lys |
| 225 | | | | | 230 | | | | | 235 | | | | | 240 |
| His | Leu | Val | Ser | Tyr | Ser | Ile | Glu | Tyr | Val | His | Ser | Phe | His | Thr | Gly |
| | | | | 245 | | | | | 250 | | | | | 255 | |
| Ala | Phe | Val | Tyr | Phe | Leu | Thr | Val | Gln | Pro | Ala | Ser | Val | Thr | Asp | Asp |
| | | | 260 | | | | | 265 | | | | | 270 | | |
| Pro | Ser | Ala | Leu | His | Thr | Arg | Leu | Ala | Arg | Leu | Ser | Ala | Thr | Glu | Pro |
| | | 275 | | | | | 280 | | | | | 285 | | | |
| Glu | Leu | Gly | Asp | Tyr | Arg | Glu | Leu | Val | Leu | Asp | Cys | Arg | Phe | Ala | Pro |
| | 290 | | | | | 295 | | | | | 300 | | | | |
| Lys | Arg | Arg | Arg | Arg | Gly | Ala | Pro | Glu | Gly | Gly | Gln | Pro | Tyr | Pro | Val |
| 305 | | | | | 310 | | | | | 315 | | | | | 320 |
| Leu | Gln | Val | Ala | His | Ser | Ala | Pro | Val | Gly | Ala | Gln | Leu | Ala | Thr | Glu |
| | | | | 325 | | | | | 330 | | | | | 335 | |
| Leu | Ser | Ile | Ala | Glu | Gly | Gln | Glu | Val | Leu | Phe | Gly | Val | Phe | Val | Thr |
| | | | 340 | | | | | 345 | | | | | 350 | | |
| Gly | Lys | Asp | Gly | Gly | Pro | Gly | Val | Gly | Pro | Asn | Ser | Val | Val | Cys | Ala |
| | | 355 | | | | | 360 | | | | | 365 | | | |
| Phe | Pro | Ile | Asp | Leu | Leu | Asp | Thr | Leu | Ile | Asp | Glu | Gly | Val | Glu | Arg |
| | 370 | | | | | 375 | | | | | 380 | | | | |
| Cys | Cys | Glu | Ser | Pro | Val | His | Pro | Gly | Leu | Arg | Arg | Gly | Leu | Asp | Phe |
| 385 | | | | | 390 | | | | | 395 | | | | | 400 |
| Phe | Gln | Ser | Pro | Ser | Phe | Cys | Pro | Asn | Pro | Pro | Gly | Leu | Glu | Ala | Leu |
| | | | | 405 | | | | | 410 | | | | | 415 | |
| Ser | Pro | Asn | Thr | Ser | Cys | Arg | His | Phe | Pro | Leu | Leu | Val | Ser | Ser | Ser |
| | | | 420 | | | | | 425 | | | | | 430 | | |
| Phe | Ser | Arg | Val | Asp | Leu | Phe | Asn | Gly | Leu | Leu | Gly | Pro | Val | Gln | Val |
| | | 435 | | | | | 440 | | | | | 445 | | | |
| Thr | Ala | Leu | Tyr | Val | Thr | Arg | Leu | Asp | Asn | Val | Thr | Val | Ala | His | Met |
| | 450 | | | | | 455 | | | | | 460 | | | | |
| Gly | Thr | Met | Asp | Gly | Arg | Ile | Leu | Gln | Val | Glu | Leu | Val | Arg | Ser | Leu |
| 465 | | | | | 470 | | | | | 475 | | | | | 480 |

FIG. 4B-2 SEQ ID NO: 8 cont.

Asn Tyr Leu Leu Tyr Val Ser Asn Phe Ser Leu Gly Asp Ser Gly Gln
485 490 495

Pro Val Gln Arg Asp Val Ser Arg Leu Gly Asp His Leu Leu Phe Ala
500 505 510

Ser Gly Asp Gln Val Phe Gln Val Pro Ile Arg Gly Pro Gly Cys Arg
515 520 525

His Phe Leu Thr Cys Gly Arg Cys Leu Arg Ala Trp His Phe Met Gly
530 535 540

Cys Gly Trp Cys Gly Asn Met Cys Gly Gln Gln Lys Glu Cys Pro Gly
545 550 555 560

Ser Trp Gln Gln Asp His Cys Pro Pro Lys Leu Thr Glu Phe His Pro
565 570 575

His Ser Gly Pro Leu Arg Gly Ser Thr Arg Leu Thr Leu Cys Gly Ser
580 585 590

Asn Phe Tyr Leu His Pro Ser Gly Leu Val Pro Glu Gly Thr His Gln
595 600 605

Val Thr Val Gly Gln Ser Pro Cys Arg Pro Leu Pro Lys Asp Ser Ser
610 615 620

Lys Leu Arg Pro Val Pro Arg Lys Asp Phe Val Glu Glu Phe Glu Cys
625 630 635 640

Glu Leu Glu Pro Leu Gly Thr Gln Ala Val Gly Pro Thr Asn Val Ser
645 650 655

Leu Thr Val Thr Asn Met Pro Pro Gly Lys His Phe Arg Val Asp Gly
660 665 670

Thr Ser Val Leu Arg Gly Phe Ser Phe Met Glu Pro Val Leu Ile Ala
675 680 685

Val Gln Pro Leu Phe Gly Pro Arg Ala Gly Gly Thr Cys Leu Thr Leu
690 695 700

Glu Gly Gln Ser Leu Ser Val Gly Thr Ser Arg Ala Val Leu Val Asn
705 710 715 720

Gly Thr Glu Cys Leu Leu Ala Arg Val Ser Glu Gly Gln Leu Leu Cys
725 730 735

Ala Thr Pro Pro Gly Ala Thr Val Ala Ser Val Pro Leu Ser Leu Gln
740 745 750

Val Gly Gly Ala Gln Val Pro Gly Ser Trp Thr Phe Gln Tyr Arg Glu
755 760 765

Asp Pro Val Val Leu Ser Ile Ser Pro Asn Cys Gly Tyr Ile Asn Ser
770 775 780

His Ile Thr Ile Cys Gly Gln His Leu Thr Ser Ala Trp His Leu Val
785 790 795 800

Leu Ser Phe His Asp Gly Leu Arg Ala Val Glu Ser Arg Cys Glu Arg
805 810 815

Gln Leu Pro Glu Gln Gln Leu Cys Arg Leu Pro Glu Tyr Val Val Arg
820 825 830

Asp Pro Gln Gly Trp Val Ala Gly Asn Leu Ser Ala Arg Gly Asp Gly
835 840 845

Ala Ala Gly Phe Thr Leu Pro Gly Phe Arg Phe Leu Pro Pro Pro His
850 855 860

Pro Pro Ser Ala Asn Leu Val Pro Leu Lys Pro Glu Glu His Ala Ile
865 870 875 880

Lys Phe Glu Val Cys Val Asp Ala Leu Pro Ala Ile Asp Gly Leu Asp
885 890 895

Ser Thr Thr Cys Val His Gly Ala Ser Phe Ser Asp Ser Glu Asp Glu
900 905 910

Ser Cys Val Pro Leu Leu Arg Lys Glu Ser Ile Gln Leu Arg Asp Leu
915 920 925

Asp Ser Ala Leu Leu Ala Glu Val Lys Asp Val Leu Ile Pro His Glu
930 935 940

Arg Val Val Thr His Ser Asp Arg Val Ile Gly Lys Gly His Phe Gly
945 950 955 960

FIG. 4B-3 SEQ ID NO: 8 cont.

```
Val Val Tyr His Gly Glu Tyr Ile Asp Gln Ala Gln Asn Arg Ile Gln
                965                 970                 975
Cys Ala Ile Lys Ser Leu Ser Arg Ile Thr Glu Met Gln Gln Val Glu
            980                 985                 990
Ala Phe Leu Arg Glu Gly Leu Leu Met Arg Gly Leu Asn His Pro Asn
        995                 1000                1005
Val Leu Ala Leu Ile Gly Ile Met Leu Pro Pro Glu Gly Leu Pro His
    1010                1015                1020
Val Leu Leu Pro Tyr Met Cys His Gly Asp Leu Leu Gln Phe Ile Arg
1025                1030                1035                1040
Ser Pro Gln Arg Asn Pro Thr Val Lys Asp Leu Ile Ser Phe Gly Leu
                1045                1050                1055
Gln Val Ala Arg Gly Met Glu Tyr Leu Ala Glu Gln Lys Phe Val His
            1060                1065                1070
Arg Asp Leu Ala Ala Arg Asn Cys Met Leu Asp Glu Ser Phe Thr Val
        1075                1080                1085
Lys Val Ala Asp Phe Gly Leu Ala Arg Asp Ile Leu Asp Arg Glu Tyr
    1090                1095                1100
Tyr Ser Val Gln Gln His Arg His Ala Arg Leu Pro Val Lys Trp Met
1105                1110                1115                1120
Ala Leu Glu Ser Leu Gln Thr Tyr Arg Phe Thr Thr Lys Ser Asp Val
                1125                1130                1135
Val Pro Ser Asp Ala Ala Met Leu Gly Gly Arg Pro Ser Ser Ala Thr
            1140                1145                1150
His Leu Gln Ser Thr Ser Gly Gly Gly Gly Ala Asp Ser Val Cys Thr
        1155                1160                1165
Ala Trp Gly Pro Leu Cys Ala Ala Ala Ser Asn Leu His Glu Leu Glu
    1170                1175                1180
Leu Thr Pro Arg Leu Pro Leu Gly His Ala Arg Pro Glu Gln Trp Pro
1185                1190                1195                1200
Ser Thr Leu Phe Leu Pro Phe Asn Phe Gln Arg Gln
                1205                1210
```

FIG. 4C-1 Coding Sequence (SEQ ID NO: 7 & 8)

| | | | | | | | | | | | | | | | | |
|---|---|---|---|---|---|---|---|---|---|---|---|---|---|---|---|---|
| ATG | GAG | CTC | CTC | CCG | CCG | CTG | CCT | CAG | TCC | TTC | CTG | TTG | CTG | CTG | CTG | 48 |
| Met | Glu | Leu | Leu | Pro | Pro | Leu | Pro | Gln | Ser | Phe | Leu | Leu | Leu | Leu | Leu | |
| | | | | 5 | | | | | 10 | | | | | 15 | | |
| TTG | CCT | GCC | AAG | CCC | GCG | GCG | GGC | GAG | GAC | TGG | CAG | TGC | CCG | CGC | ACC | 96 |
| Leu | Pro | Ala | Lys | Pro | Ala | Ala | Gly | Glu | Asp | Trp | Gln | Cys | Pro | Arg | Thr | |
| | | | 20 | | | | | 25 | | | | | 30 | | | |
| CCC | TAC | GCG | GCC | TCT | CGC | GAC | TTT | GAC | GTG | AAG | TAC | GTG | GTG | CCC | AGC | 144 |
| Pro | Tyr | Ala | Ala | Ser | Arg | Asp | Phe | Asp | Val | Lys | Tyr | Val | Val | Pro | Ser | |
| | | 35 | | | | | 40 | | | | | 45 | | | | |
| TTC | TCC | GCC | GGA | GGC | CTG | GTA | CAG | GCC | ATG | GTG | ACC | TAC | GAG | GGC | GAC | 192 |
| Phe | Ser | Ala | Gly | Gly | Leu | Val | Gln | Ala | Met | Val | Thr | Tyr | Glu | Gly | Asp | |
| | 50 | | | | | 55 | | | | | 60 | | | | | |
| AGA | AAT | GAG | AGT | GCT | GTG | TTT | GTA | GCC | ATA | CGC | AAT | CGC | CTG | CAT | GTG | 240 |
| Arg | Asn | Glu | Ser | Ala | Val | Phe | Val | Ala | Ile | Arg | Asn | Arg | Leu | His | Val | |
| 65 | | | | | 70 | | | | | 75 | | | | | 80 | |
| CTT | GGG | CCT | GAC | CTG | AAG | TCT | GTC | CAG | AGC | CTG | GCC | ACG | GGC | CCT | GCT | 288 |
| Leu | Gly | Pro | Asp | Leu | Lys | Ser | Val | Gln | Ser | Leu | Ala | Thr | Gly | Pro | Ala | |
| | | | | 85 | | | | | 90 | | | | | 95 | | |
| GGA | GAC | CCT | GGC | TGC | CAG | ACG | TGT | GCA | GCC | TGT | GGC | CCA | GGA | CCC | CAC | 336 |
| Gly | Asp | Pro | Gly | Cys | Gln | Thr | Cys | Ala | Ala | Cys | Gly | Pro | Gly | Pro | His | |
| | | | 100 | | | | | 105 | | | | | 110 | | | |
| GGC | CCT | CCC | GGT | GAC | ACA | GAC | ACA | AAG | GTG | CTG | GTG | CTG | GAT | CCC | GCG | 384 |
| Gly | Pro | Pro | Gly | Asp | Thr | Asp | Thr | Lys | Val | Leu | Val | Leu | Asp | Pro | Ala | |
| | | 115 | | | | | 120 | | | | | 125 | | | | |
| CTG | CCT | GCG | CTG | GTC | AGT | TGT | GGC | TCC | AGC | CTG | CAG | GGC | CGC | TGC | TTC | 432 |
| Leu | Pro | Ala | Leu | Val | Ser | Cys | Gly | Ser | Ser | Leu | Gln | Gly | Arg | Cys | Phe | |
| | 130 | | | | | 135 | | | | | 140 | | | | | |
| CTG | CAT | GAC | CTA | GAG | CCC | CAA | GGG | ACA | GCC | GTG | CAT | CTG | GCA | GCG | CCA | 480 |
| Leu | His | Asp | Leu | Glu | Pro | Gln | Gly | Thr | Ala | Val | His | Leu | Ala | Ala | Pro | |
| 145 | | | | | 150 | | | | | 155 | | | | | 160 | |
| GCC | TGC | CTC | TTC | TCA | GCC | CAC | CAT | AAC | CGG | CCC | GAT | GAC | TGC | CCC | GAC | 528 |
| Ala | Cys | Leu | Phe | Ser | Ala | His | His | Asn | Arg | Pro | Asp | Asp | Cys | Pro | Asp | |
| | | | | 165 | | | | | 170 | | | | | 175 | | |
| TGT | GTG | GCC | AGC | CCA | TTG | GGC | ACC | CGT | GTA | ACT | GTG | GTT | GAG | CAA | GGC | 576 |
| Cys | Val | Ala | Ser | Pro | Leu | Gly | Thr | Arg | Val | Thr | Val | Val | Glu | Gln | Gly | |
| | | | 180 | | | | | 185 | | | | | 190 | | | |
| CAG | GCC | TCC | TAT | TTC | TAC | GTG | GCA | TCC | TCA | CTG | GAC | GCA | GCC | GTG | GCT | 624 |
| Gln | Ala | Ser | Tyr | Phe | Tyr | Val | Ala | Ser | Ser | Leu | Asp | Ala | Ala | Val | Ala | |
| | | 195 | | | | | 200 | | | | | 205 | | | | |
| GGC | AGC | TTC | AGC | CCA | CGC | TCA | GTG | TCT | ATC | AGG | CGT | CTC | AAG | GCT | GAC | 672 |
| Gly | Ser | Phe | Ser | Pro | Arg | Ser | Val | Ser | Ile | Arg | Arg | Leu | Lys | Ala | Asp | |
| | 210 | | | | | 215 | | | | | 220 | | | | | |
| GCC | TCG | GGA | TTC | GCA | CCG | GGC | TTT | GTG | GCG | TTG | TCA | GTG | CTG | CCC | AAG | 720 |
| Ala | Ser | Gly | Phe | Ala | Pro | Gly | Phe | Val | Ala | Leu | Ser | Val | Leu | Pro | Lys | |
| 225 | | | | | 230 | | | | | 235 | | | | | 240 | |
| CAT | CTT | GTC | TCC | TAC | AGT | ATT | GAA | TAC | GTG | CAC | AGC | TTC | CAC | ACG | GGA | 768 |
| His | Leu | Val | Ser | Tyr | Ser | Ile | Glu | Tyr | Val | His | Ser | Phe | His | Thr | Gly | |
| | | | | 245 | | | | | 250 | | | | | 255 | | |
| GCC | TTC | GTA | TAC | TTC | CTG | ACT | GTA | CAG | CCG | GCC | AGC | GTG | ACA | GAT | GAT | 816 |
| Ala | Phe | Val | Tyr | Phe | Leu | Thr | Val | Gln | Pro | Ala | Ser | Val | Thr | Asp | Asp | |
| | | | 260 | | | | | 265 | | | | | 270 | | | |
| CCT | AGT | GCC | CTG | CAC | ACA | CGC | CTG | GCA | CGG | CTT | AGC | GCC | ACT | GAG | CCA | 864 |
| Pro | Ser | Ala | Leu | His | Thr | Arg | Leu | Ala | Arg | Leu | Ser | Ala | Thr | Glu | Pro | |
| | | 275 | | | | | 280 | | | | | 285 | | | | |
| GAG | TTG | GGT | GAC | TAT | CGG | GAG | CTG | GTC | CTC | GAC | TGC | AGA | TTT | GCT | CCA | 912 |
| Glu | Leu | Gly | Asp | Tyr | Arg | Glu | Leu | Val | Leu | Asp | Cys | Arg | Phe | Ala | Pro | |
| | 290 | | | | | 295 | | | | | 300 | | | | | |
| AAA | CGC | AGG | CGC | CGG | GGG | GCC | CCA | GAA | GGC | GGA | CAG | CCC | TAC | CCT | GTG | 960 |
| Lys | Arg | Arg | Arg | Arg | Gly | Ala | Pro | Glu | Gly | Gly | Gln | Pro | Tyr | Pro | Val | |
| 305 | | | | | 310 | | | | | 315 | | | | | 320 | |

FIG. 4C-2 Coding Sequence (SEQ ID NO: 7 & 8) cont.

| | | | | | | | | | | | | | | | | |
|---|---|---|---|---|---|---|---|---|---|---|---|---|---|---|---|---|
| CTG | CAG | GTG | GCC | CAC | TCC | GCT | CCA | GTG | GGT | GCC | CAA | CTT | GCC | ACT | GAG | 1008 |
| Leu | Gln | Val | Ala | His | Ser | Ala | Pro | Val | Gly | Ala | Gln | Leu | Ala | Thr | Glu | |
| | | | | 325 | | | | | 330 | | | | | 335 | | |
| CTG | AGC | ATC | GCC | GAG | GGC | CAG | GAA | GTA | CTA | TTT | GGG | GTC | TTT | GTG | ACT | 1056 |
| Leu | Ser | Ile | Ala | Glu | Gly | Gln | Glu | Val | Leu | Phe | Gly | Val | Phe | Val | Thr | |
| | | | 340 | | | | | 345 | | | | | 350 | | | |
| GGC | AAG | GAT | GGT | GGT | CCT | GGC | GTG | GGC | CCC | AAC | TCT | GTC | GTC | TGT | GCC | 1104 |
| Gly | Lys | Asp | Gly | Gly | Pro | Gly | Val | Gly | Pro | Asn | Ser | Val | Val | Cys | Ala | |
| | | 355 | | | | | 360 | | | | | 365 | | | | |
| TTC | CCC | ATT | GAC | CTG | CTG | GAC | ACA | CTA | ATT | GAT | GAG | GGT | GTG | GAG | CGC | 1152 |
| Phe | Pro | Ile | Asp | Leu | Leu | Asp | Thr | Leu | Ile | Asp | Glu | Gly | Val | Glu | Arg | |
| | 370 | | | | | 375 | | | | | 380 | | | | | |
| TGT | TGT | GAA | TCC | CCA | GTC | CAT | CCA | GGC | CTC | CGG | CGA | GGC | CTC | GAC | TTC | 1200 |
| Cys | Cys | Glu | Ser | Pro | Val | His | Pro | Gly | Leu | Arg | Arg | Gly | Leu | Asp | Phe | |
| 385 | | | | | 390 | | | | | 395 | | | | | 400 | |
| TTC | CAG | TCG | CCC | AGT | TTT | TGC | CCC | AAC | CCG | CCT | GGC | CTG | GAA | GCC | CTC | 1248 |
| Phe | Gln | Ser | Pro | Ser | Phe | Cys | Pro | Asn | Pro | Pro | Gly | Leu | Glu | Ala | Leu | |
| | | | | 405 | | | | | 410 | | | | | 415 | | |
| AGC | CCC | AAC | ACC | AGC | TGC | CGC | CAC | TTC | CCT | CTG | CTG | GTC | AGT | AGC | AGC | 1296 |
| Ser | Pro | Asn | Thr | Ser | Cys | Arg | His | Phe | Pro | Leu | Leu | Val | Ser | Ser | Ser | |
| | | | 420 | | | | | 425 | | | | | 430 | | | |
| TTC | TCA | CGT | GTG | GAC | CTA | TTC | AAT | GGG | CTG | TTG | GGA | CCA | GTA | CAG | GTC | 1344 |
| Phe | Ser | Arg | Val | Asp | Leu | Phe | Asn | Gly | Leu | Leu | Gly | Pro | Val | Gln | Val | |
| | | 435 | | | | | 440 | | | | | 445 | | | | |
| ACT | GCA | TTG | TAT | GTG | ACA | CGC | CTT | GAC | AAC | GTC | ACA | GTG | GCA | CAC | ATG | 1392 |
| Thr | Ala | Leu | Tyr | Val | Thr | Arg | Leu | Asp | Asn | Val | Thr | Val | Ala | His | Met | |
| | 450 | | | | | 455 | | | | | 460 | | | | | |
| GGC | ACA | ATG | GAT | GGG | CGT | ATC | CTG | CAG | GTG | GAG | CTG | GTC | AGG | TCA | CTA | 1440 |
| Gly | Thr | Met | Asp | Gly | Arg | Ile | Leu | Gln | Val | Glu | Leu | Val | Arg | Ser | Leu | |
| 465 | | | | | 470 | | | | | 475 | | | | | 480 | |
| AAC | TAC | TTG | CTG | TAT | GTG | TCC | AAC | TTC | TCA | CTG | GGT | GAC | AGT | GGG | CAG | 1488 |
| Asn | Tyr | Leu | Leu | Tyr | Val | Ser | Asn | Phe | Ser | Leu | Gly | Asp | Ser | Gly | Gln | |
| | | | | 485 | | | | | 490 | | | | | 495 | | |
| CCC | GTG | CAG | CGG | GAT | GTC | AGT | CGT | CTT | GGG | GAC | CAC | CTA | CTC | TTT | GCC | 1536 |
| Pro | Val | Gln | Arg | Asp | Val | Ser | Arg | Leu | Gly | Asp | His | Leu | Leu | Phe | Ala | |
| | | | 500 | | | | | 505 | | | | | 510 | | | |
| TCT | GGG | GAC | CAG | GTT | TTC | CAG | GTA | CCT | ATC | CGA | GGC | CCT | GGC | TGC | CGC | 1584 |
| Ser | Gly | Asp | Gln | Val | Phe | Gln | Val | Pro | Ile | Arg | Gly | Pro | Gly | Cys | Arg | |
| | | 515 | | | | | 520 | | | | | 525 | | | | |
| CAC | TTC | CTG | ACC | TGT | GGG | CGT | TGC | CTA | AGG | GCA | TGG | CAT | TTC | ATG | GGC | 1632 |
| His | Phe | Leu | Thr | Cys | Gly | Arg | Cys | Leu | Arg | Ala | Trp | His | Phe | Met | Gly | |
| | 530 | | | | | 535 | | | | | 540 | | | | | |
| TGT | GGC | TGG | TGT | GGG | AAC | ATG | TGC | GGC | CAG | CAG | AAG | GAG | TGT | CCT | GGC | 1680 |
| Cys | Gly | Trp | Cys | Gly | Asn | Met | Cys | Gly | Gln | Gln | Lys | Glu | Cys | Pro | Gly | |
| 545 | | | | | 550 | | | | | 555 | | | | | 560 | |
| TCC | TGG | CAA | CAG | GAC | CAC | TGC | CCA | CCT | AAG | CTT | ACT | GAG | TTC | CAC | CCC | 1728 |
| Ser | Trp | Gln | Gln | Asp | His | Cys | Pro | Pro | Lys | Leu | Thr | Glu | Phe | His | Pro | |
| | | | | 565 | | | | | 570 | | | | | 575 | | |
| CAC | AGT | GGA | CCT | CTA | AGG | GGC | AGT | ACA | AGG | CTG | ACC | CTG | TGT | GGC | TCC | 1776 |
| His | Ser | Gly | Pro | Leu | Arg | Gly | Ser | Thr | Arg | Leu | Thr | Leu | Cys | Gly | Ser | |
| | | | 580 | | | | | 585 | | | | | 590 | | | |
| AAC | TTC | TAC | CTT | CAC | CCT | TCT | GGT | CTG | GTG | CCT | GAG | GGA | ACC | CAT | CAG | 1824 |
| Asn | Phe | Tyr | Leu | His | Pro | Ser | Gly | Leu | Val | Pro | Glu | Gly | Thr | His | Gln | |
| | | 595 | | | | | 600 | | | | | 605 | | | | |
| GTC | ACT | GTG | GGC | CAA | AGT | CCC | TGC | CGG | CCA | CTG | CCC | AAG | GAC | AGC | TCA | 1872 |
| Val | Thr | Val | Gly | Gln | Ser | Pro | Cys | Arg | Pro | Leu | Pro | Lys | Asp | Ser | Ser | |
| | 610 | | | | | 615 | | | | | 620 | | | | | |
| AAA | CTC | AGA | CCA | GTG | CCC | CGG | AAA | GAC | TTT | GTA | GAG | GAG | TTT | GAG | TGT | 1920 |
| Lys | Leu | Arg | Pro | Val | Pro | Arg | Lys | Asp | Phe | Val | Glu | Glu | Phe | Glu | Cys | |
| 625 | | | | | 630 | | | | | 635 | | | | | 640 | |

FIG. 4C-3 Coding Sequence (SEQ ID NO: 7 & 8) cont.

```
GAA  CTG  GAG  CCC  TTG  GGC  ACC  CAG  GCA  GTG  GGG  CCT  ACC  AAC  GTC  AGC  1968
Glu  Leu  Glu  Pro  Leu  Gly  Thr  Gln  Ala  Val  Gly  Pro  Thr  Asn  Val  Ser
                    645                      650                      655
CTC  ACC  GTG  ACT  AAC  ATG  CCA  CCG  GGC  AAG  CAC  TTC  CGG  GTA  GAC  GGC  2016
Leu  Thr  Val  Thr  Asn  Met  Pro  Pro  Gly  Lys  His  Phe  Arg  Val  Asp  Gly
               660                      665                      670
ACC  TCC  GTG  CTG  AGA  GGC  TTC  TCT  TTC  ATG  GAG  CCA  GTG  CTG  ATA  GCA  2064
Thr  Ser  Val  Leu  Arg  Gly  Phe  Ser  Phe  Met  Glu  Pro  Val  Leu  Ile  Ala
          675                      680                      685
GTG  CAA  CCC  CTC  TTT  GGC  CCA  CGG  GCA  GGA  GGC  ACC  TGT  CTC  ACT  CTT  2112
Val  Gln  Pro  Leu  Phe  Gly  Pro  Arg  Ala  Gly  Gly  Thr  Cys  Leu  Thr  Leu
     690                      695                      700
GAA  GGC  CAG  AGT  CTG  TCT  GTA  GGC  ACC  AGC  CGG  GCT  GTG  CTG  GTC  AAT  2160
Glu  Gly  Gln  Ser  Leu  Ser  Val  Gly  Thr  Ser  Arg  Ala  Val  Leu  Val  Asn
705                      710                      715                      720
GGG  ACT  GAG  TGT  CTG  CTA  GCA  CGG  GTC  AGT  GAG  GGG  CAG  CTT  TTA  TGT  2208
Gly  Thr  Glu  Cys  Leu  Leu  Ala  Arg  Val  Ser  Glu  Gly  Gln  Leu  Leu  Cys
                    725                      730                      735
GCC  ACA  CCC  CCT  GGG  GCC  ACG  GTG  GCC  AGT  GTC  CCC  CTT  AGC  CTG  CAG  2256
Ala  Thr  Pro  Pro  Gly  Ala  Thr  Val  Ala  Ser  Val  Pro  Leu  Ser  Leu  Gln
               740                      745                      750
GTG  GGG  GGT  GCC  CAG  GTA  CCT  GGT  TCC  TGG  ACC  TTC  CAG  TAC  AGA  GAA  2304
Val  Gly  Gly  Ala  Gln  Val  Pro  Gly  Ser  Trp  Thr  Phe  Gln  Tyr  Arg  Glu
          755                      760                      765
GAC  CCT  GTC  GTG  CTA  AGC  ATC  AGC  CCC  AAC  TGT  GGC  TAC  ATC  AAC  TCC  2352
Asp  Pro  Val  Val  Leu  Ser  Ile  Ser  Pro  Asn  Cys  Gly  Tyr  Ile  Asn  Ser
     770                      775                      780
CAC  ATC  ACC  ATC  TGT  GGC  CAG  CAT  CTA  ACT  TCA  GCA  TGG  CAC  TTA  GTG  2400
His  Ile  Thr  Ile  Cys  Gly  Gln  His  Leu  Thr  Ser  Ala  Trp  His  Leu  Val
785                      790                      795                      800
CTG  TCA  TTC  CAT  GAC  GGG  CTT  AGG  GCA  GTG  GAA  AGC  AGG  TGT  GAG  AGG  2448
Leu  Ser  Phe  His  Asp  Gly  Leu  Arg  Ala  Val  Glu  Ser  Arg  Cys  Glu  Arg
                    805                      810                      815
CAG  CTT  CCA  GAG  CAG  CAG  CTG  TGC  CGC  CTT  CCT  GAA  TAT  GTG  GTC  CGA  2496
Gln  Leu  Pro  Glu  Gln  Gln  Leu  Cys  Arg  Leu  Pro  Glu  Tyr  Val  Val  Arg
               820                      825                      830
GAC  CCC  CAG  GGA  TGG  GTG  GCA  GGG  AAT  CTG  AGT  GCC  CGA  GGG  GAT  GGA  2544
Asp  Pro  Gln  Gly  Trp  Val  Ala  Gly  Asn  Leu  Ser  Ala  Arg  Gly  Asp  Gly
          835                      840                      845
GCT  GCT  GGC  TTT  ACA  CTG  CCT  GGC  TTT  CGC  TTC  CTA  CCC  CCA  CCC  CAT  2592
Ala  Ala  Gly  Phe  Thr  Leu  Pro  Gly  Phe  Arg  Phe  Leu  Pro  Pro  Pro  His
     850                      855                      860
CCA  CCC  AGT  GCC  AAC  CTA  GTT  CCA  CTG  AAG  CCT  GAG  GAG  CAT  GCC  ATT  2640
Pro  Pro  Ser  Ala  Asn  Leu  Val  Pro  Leu  Lys  Pro  Glu  Glu  His  Ala  Ile
865                      870                      875                      880
AAG  TTT  GAG  GTC  TGC  GTA  GAT  GCA  CTC  CCT  GCC  ATT  GAT  GGT  CTG  GAT  2688
Lys  Phe  Glu  Val  Cys  Val  Asp  Ala  Leu  Pro  Ala  Ile  Asp  Gly  Leu  Asp
                    885                      890                      895
TCC  ACC  ACT  TGT  GTC  CAT  GGA  GCA  TCC  TTC  TCC  GAT  AGT  GAA  GAT  GAA  2736
Ser  Thr  Thr  Cys  Val  His  Gly  Ala  Ser  Phe  Ser  Asp  Ser  Glu  Asp  Glu
               900                      905                      910
TCC  TGT  GTG  CCA  CTG  CTG  CGG  AAA  GAG  TCC  ATC  CAG  CTA  AGG  GAC  CTG  2784
Ser  Cys  Val  Pro  Leu  Leu  Arg  Lys  Glu  Ser  Ile  Gln  Leu  Arg  Asp  Leu
          915                      920                      925
GAC  TCT  GCG  CTC  TTG  GCT  GAG  GTC  AAG  GAT  GTG  CTG  ATT  CCC  CAT  GAG  2832
Asp  Ser  Ala  Leu  Leu  Ala  Glu  Val  Lys  Asp  Val  Leu  Ile  Pro  His  Glu
     930                      935                      940
CGG  GTG  GTC  ACC  CAC  AGT  GAC  CGA  GTC  ATT  GGC  AAA  GGC  CAC  TTT  GGA  2880
Arg  Val  Val  Thr  His  Ser  Asp  Arg  Val  Ile  Gly  Lys  Gly  His  Phe  Gly
945                      950                      955                      960
```

FIG. 4C-4 Coding Sequence (SEQ ID NO: 7 & 8) cont.

```
GTT   GTC   TAC   CAC   GGA   GAA   TAC   ATA   GAC   CAG   GCC   CAG   AAT   CGA   ATC   CAA   2928
Val   Val   Tyr   His   Gly   Glu   Tyr   Ile   Asp   Gln   Ala   Gln   Asn   Arg   Ile   Gln
                        965                           970                           975
TGT   GCC   ATC   AAG   TCA   CTA   AGT   CGC   ATC   ACA   GAG   ATG   CAG   CAG   GTG   GAG   2976
Cys   Ala   Ile   Lys   Ser   Leu   Ser   Arg   Ile   Thr   Glu   Met   Gln   Gln   Val   Glu
                  980                           985                           990
GCC   TTC   CTG   CGA   GAG   GGG   CTG   CTC   ATG   CGT   GGC   CTG   AAC   CAC   CCG   AAT   3024
Ala   Phe   Leu   Arg   Glu   Gly   Leu   Leu   Met   Arg   Gly   Leu   Asn   His   Pro   Asn
            995                           1000                          1005
GTG   CTG   GCT   CTC   ATT   GGT   ATC   ATG   TTG   CCA   CCT   GAG   GGC   CTG   CCC   CAT   3072
Val   Leu   Ala   Leu   Ile   Gly   Ile   Met   Leu   Pro   Pro   Glu   Gly   Leu   Pro   His
      1010                          1015                          1020
GTG   CTG   CTG   CCC   TAT   ATG   TGC   CAC   GGT   GAC   CTG   CTC   CAG   TTC   ATC   CGC   3120
Val   Leu   Leu   Pro   Tyr   Met   Cys   His   Gly   Asp   Leu   Leu   Gln   Phe   Ile   Arg
1025                          1030                          1035                          1040
TCA   CCT   CAG   CGG   AAC   CCC   ACC   GTG   AAG   GAC   CTC   ATC   AGC   TTT   GGC   CTG   3168
Ser   Pro   Gln   Arg   Asn   Pro   Thr   Val   Lys   Asp   Leu   Ile   Ser   Phe   Gly   Leu
                        1045                          1050                          1055
CAG   GTA   GCC   CGC   GGC   ATG   GAG   TAC   CTG   GCA   GAG   CAG   AAG   TTT   GTG   CAC   3216
Gln   Val   Ala   Arg   Gly   Met   Glu   Tyr   Leu   Ala   Glu   Gln   Lys   Phe   Val   His
                  1060                          1065                          1070
AGG   GAC   CTG   GCT   GCG   CGG   AAC   TGC   ATG   CTG   GAC   GAG   TCA   TTC   ACA   GTC   3264
Arg   Asp   Leu   Ala   Ala   Arg   Asn   Cys   Met   Leu   Asp   Glu   Ser   Phe   Thr   Val
            1075                          1080                          1085
AAG   GTG   GCT   GAC   TTT   GGT   TTG   GCC   CGC   GAC   ATC   CTG   GAC   AGG   GAG   TAC   3312
Lys   Val   Ala   Asp   Phe   Gly   Leu   Ala   Arg   Asp   Ile   Leu   Asp   Arg   Glu   Tyr
      1090                          1095                          1100
TAT   AGT   GTT   CAA   CAG   CAT   CGC   CAC   GCT   CGC   CTA   CCT   GTG   AAG   TGG   ATG   3360
Tyr   Ser   Val   Gln   Gln   His   Arg   His   Ala   Arg   Leu   Pro   Val   Lys   Trp   Met
1105                          1110                          1115                          1120
GCG   CTG   GAG   AGC   CTG   CAG   ACC   TAT   AGA   TTT   ACC   ACC   AAG   TCT   GAT   GTG   3408
Ala   Leu   Glu   Ser   Leu   Gln   Thr   Tyr   Arg   Phe   Thr   Thr   Lys   Ser   Asp   Val
                        1125                          1130                          1135
GTA   CCA   AGT   GAT   GCA   GCA   ATG   CTG   GGA   GGC   AGA   CCC   AGC   AGT   GCG   ACC   3456
Val   Pro   Ser   Asp   Ala   Ala   Met   Leu   Gly   Gly   Arg   Pro   Ser   Ser   Ala   Thr
                  1140                          1145                          1150
CAC   CTT   CAG   AGT   ACT   AGT   GGG   GGA   GGT   GGA   GCA   GAT   AGT   GTC   TGC   ACT   3504
His   Leu   Gln   Ser   Thr   Ser   Gly   Gly   Gly   Gly   Ala   Asp   Ser   Val   Cys   Thr
            1155                          1160                          1165
GCT   TGG   GGA   CCA   TTA   TGT   GCA   GCT   GCC   AGC   AAC   CTA   CAT   GAA   CTT   GAG   3552
Ala   Trp   Gly   Pro   Leu   Cys   Ala   Ala   Ala   Ser   Asn   Leu   His   Glu   Leu   Glu
      1170                          1175                          1180
CTA   ACC   CCA   AGG   CTG   CCT   CTG   GGC   CAT   GCC   AGG   CCA   GAG   CAG   TGG   CCC   3600
Leu   Thr   Pro   Arg   Leu   Pro   Leu   Gly   His   Ala   Arg   Pro   Glu   Gln   Trp   Pro
1185                          1190                          1195                          1200
TCC   ACC   TTG   TTC   CTG   CCC   TTT   AAC   TTT   CAG   AGG   CAA                           3636
Ser   Thr   Leu   Phe   Leu   Pro   Phe   Asn   Phe   Gln   Arg   Gln
                        1205                          1210
```

FIG. 5-1 SEQ ID NOs: 2, 4, 6, 8

```
Ron-V3 GGATCCTCTAGGGTC CCAGCTCGCCTCGAT GGAGCTCCTCCCGCC GCTGCCTCAGTCCTT CCTGTTGCTGCTGCT GTTGCCTGCCAAGCC   90
Ron-V2 GGATCCTCTAGGGTC CCAGCTCGCCTCGAT GGAGCTCCTCCCGCC GCTGCCTCAGTCCTT CCTGTTGCTGCTGCT GTTGCCTGCCAAGCC   90
Ron-V1 GGATCCTCTAGGGTC CCAGCTCGCCTCGAT GGAGCTCCTCCCGCC GCTGCCTCAGTCCTT CCTGTTGCTGCTGCT GTTGCCTGCCAAGCC   90
Ron    GGATCCTCTAGGGTC CCAGCTCGCCTCGAT GGAGCTCCTCCCGCC GCTGCCTCAGTCCTT CCTGTTGCTGCTGCT GTTGCCTGCCAAGCC   90

Ron-V3 CGCGGCGGGCGAGGA CTGGCAGTGCCCGCG CACCCCCTACGCGGC CTCTCGCGACTTTGA CGTGAAGTACGTGGT GCCCAGCTTCTCCGC  180
Ron-V2 CGCGGCGGGCGAGGA CTGGCAGTGCCCGCG CACCCCCTACGCGGC CTCTCGCGACTTTGA CGTGAAGTACGTGGT GCCCAGCTTCTCCGC  180
Ron-V1 CGCGGCGGGCGAGGA CTGGCAGTGCCCGCG CACCCCCTACGCGGC CTCTCGCGACTTTGA CGTGAAGTACGTGGT GCCCAGCTTCTCCGC  180
Ron    CGCGGCGGGCGAGGA CTGGCAGTGCCCGCG CACCCCCTACGCGGC CTCTCGCGACTTTGA CGTGAAGTACGTGGT GCCCAGCTTCTCCGC  180

Ron-V3 CGGAGGCCTGGTACA GGCCATGGTGACCTA CGAGGGCGACAGAAA TGAGAGTGCTGTGTT TGTAGCCATACGCAA TCGCCTGCATGTGCT  270
Ron-V2 CGGAGGCCTGGTACA GGCCATGGTGACCTA CGAGGGCGACAGAAA TGAGAGTGCTGTGTT TGTAGCCATACGCAA TCGCCTGCATGTGCT  270
Ron-V1 CGGAGGCCTGGTACA GGCCATGGTGACCTA CGAGGGCGACAGAAA TGAGAGTGCTGTGTT TGTAGCCATACGCAA TCGCCTGCATGTGCT  270
Ron    CGGAGGCCTGGTACA GGCCATGGTGACCTA CGAGGGCGACAGAAA TGAGAGTGCTGTGTT TGTAGCCATACGCAA TCGCCTGCATGTGCT  270

Ron-V3 TGGGCCTGACCTGAA GTCTGTCCAGAGCCT GGCCACGGGCCCTGC TGGAGACCCTGGCTG CCAGACGTGTGCAGC CTGTGGCCCAGGACC  360
Ron-V2 TGGGCCTGACCTGAA GTCTGTCCAGAGCCT GGCCACGGGCCCTGC TGGAGACCCTGGCTG CCAGACGTGTGCAGC CTGTGGCCCAGGACC  360
Ron-V1 TGGGCCTGACCTGAA GTCTGTCCAGAGCCT GGCCACGGGCCCTGC TGGAGACCCTGGCTG CCAGACGTGTGCAGC CTGTGGCCCAGGACC  360
Ron    TGGGCCTGACCTGAA GTCTGTCCAGAGCCT GGCCACGGGCCCTGC TGGAGACCCTGGCTG CCAGACGTGTGCAGC CTGTGGCCCAGGACC  360

Ron-V3 CCACGGCCCTCCCGG TGACACAGACACAAA GGTGCTGGTGCTGGA TCCCGCGCTGCCTGC GCTGGTCAGTTGTGG CTCCAGCCTGCAGGG  450
Ron-V2 CCACGGCCCTCCCGG TGACACAGACACAAA GGTGCTGGTGCTGGA TCCCGCGCTGCCTGC GCTGGTCAGTTGTGG CTCCAGCCTGCAGGG  450
Ron-V1 CCACGGCCCTCCCGG TGACACAGACACAAA GGTGCTGGTGCTGGA TCCCGCGCTGCCTGC GCTGGTCAGTTGTGG CTCCAGCCTGCAGGG  450
Ron    CCACGGCCCTCCCGG TGACACAGACACAAA GGTGCTGGTGCTGGA TCCCGCGCTGCCTGC GCTGGTCAGTTGTGG CTCCAGCCTGCAGGG  450
```

FIG. 5-2 SEQ ID NOs: 2, 4, 6, 8 cont.

```
Ron-V3 CCGCTGCTTCCTGCA TGACCTAGAGCCCCA AGGGACAGCCGTGCA TCTGGCAGCGCCAGC CTGCCTCTTCTCAGC CCACCATAACCGGCC 540
Ron-V2 CCGCTGCTTCCTGCA TGACCTAGAGCCCCA AGGGACAGCCGTGCA TCTGGCAGCGCCAGC CTGCCTCTTCTCAGC CCACCATAACCGGCC 540
Ron-V1 CCGCTGCTTCCTGCA TGACCTAGAGCCCCA AGGGACAGCCGTGCA TCTGGCAGCGCCAGC CTGCCTCTTCTCAGC CCACCATAACCGGCC 540
Ron    CCGCTGCTTCCTGCA TGACCTAGAGCCCCA AGGGACAGCCGTGCA TCTGGCAGCGCCAGC CTGCCTCTTCTCAGC CCACCATAACCGGCC 540

Ron-V3 CGATGACTGCCCCGA CTGTGTGGCCAGCCC ATTGGGCACCCGTGT AACTGTGGTTGAGCA AGGCCAGGCCTCCTA TTTCTACGTGGCATC 630
Ron-V2 CGATGACTGCCCCGA CTGTGTGGCCAGCCC ATTGGGCACCCGTGT AACTGTGGTTGAGCA AGGCCAGGCCTCCTA TTTCTACGTGGCATC 630
Ron-V1 CGATGACTGCCCCGA CTGTGTGGCCAGCCC ATTGGGCACCCGTGT AACTGTGGTTGAGCA AGGCCAGGCCTCCTA TTTCTACGTGGCATC 630
Ron    CGATGACTGCCCCGA CTGTGTGGCCAGCCC ATTGGGCACCCGTGT AACTGTGGTTGAGCA AGGCCAGGCCTCCTA TTTCTACGTGGCATC 630

Ron-V3 CTCACTGGACGCAGC CGTGGCTGGCAGCTT CAGCCCACGCTCAGT GTCTATCAGGCGTCT CAAGGCTGACGCCTC GGGATTCGCACCGGG 720
Ron-V2 CTCACTGGACGCAGC CGTGGCTGGCAGCTT CAGCCCACGCTCAGT GTCTATCAGGCGTCT CAAGGCTGACGCCTC GGGATTCGCACCGGG 720
Ron-V1 CTCACTGGACGCAGC CGTGGCTGGCAGCTT CAGCCCACGCTCAGT GTCTATCAGGCGTCT CAAGGCTGACGCCTC GGGATTCGCACCGGG 720
Ron    CTCACTGGACGCAGC CGTGGCTGGCAGCTT CAGCCCACGCTCAGT GTCTATCAGGCGTCT CAAGGCTGACGCCTC GGGATTCGCACCGGG 720

Ron-V3 CTTTGTGGCGTTGTC AGTGCTGCCCAAGCA TCTTGTCTCCTACAG TATTGAATACGTGCA CAGCTTCCACACGGG AGCCTTCGTATACTT 810
Ron-V2 CTTTGTGGCGTTGTC AGTGCTGCCCAAGCA TCTTGTCTCCTACAG TATTGAATACGTGCA CAGCTTCCACACGGG AGCCTTCGTATACTT 810
Ron-V1 CTTTGTGGCGTTGTC AGTGCTGCCCAAGCA TCTTGTCTCCTACAG TATTGAATACGTGCA CAGCTTCCACACGGG AGCCTTCGTATACTT 810
Ron    CTTTGTGGCGTTGTC AGTGCTGCCCAAGCA TCTTGTCTCCTACAG TATTGAATACGTGCA CAGCTTCCACACGGG AGCCTTCGTATACTT 810

Ron-V3 CCTGACTGTACAGCC GGCCAGCGTGACAGA TGATCCTAGTGCCCT GCACACACGCCTGGC ACGGCTTAGCGCCAC TGAGCCAGAGTTGGG 900
Ron-V2 CCTGACTGTACAGCC GGCCAGCGTGACAGA TGATCCTAGTGCCCT GCACACACGCCTGGC ACGGCTTAGCGCCAC TGAGCCAGAGTTGGG 900
Ron-V1 CCTGACTGTACAGCC GGCCAGCGTGACAGA TGATCCTAGTGCCCT GCACACACGCCTGGC ACGGCTTAGCGCCAC TGAGCCAGAGTTGGG 900
Ron    CCTGACTGTACAGCC GGCCAGCGTGACAGA TGATCCTAGTGCCCT GCACACACGCCTGGC ACGGCTTAGCGCCAC TGAGCCAGAGTTGGG 900
```

FIG. 5-3 SEQ ID NOs: 2, 4, 6, 8 cont.

```
Ron-V3 TGACTATCGGGAGCT GGTCCTCGACTGCAG ATTTGCTCCAAAACG CAGGCGCCGGGGGGC CCCAGAAGGCGGACA GCCCTACCCTGTGCT  990
Ron-V2 TGACTATCGGGAGCT GGTCCTCGACTGCAG ATTTGCTCCAAAACG CAGGCGCCGGGGGGC CCCAGAAGGCGGACA GCCCTACCCTGTGCT  990
Ron-V1 TGACTATCGGGAGCT GGTCCTCGACTGCAG ATTTGCTCCAAAACG CAGGCGCCGGGGGGC CCCAGAAGGCGGACA GCCCTACCCTGTGCT  990
Ron    TGACTATCGGGAGCT GGTCCTCGACTGCAG ATTTGCTCCAAAACG CAGGCGCCGGGGGGC CCCAGAAGGCGGACA GCCCTACCCTGTGCT  990

Ron-V3 GCAGGTGGCCCACTC CGCTCCAGTGGGTGC CCAACTTGCCACTGA GCTGAGCATCGCCGA GGGCCAGGAAGTACT ATTTGGGGTCTTTGT 1080
Ron-V2 GCAGGTGGCCCACTC CGCTCCAGTGGGTGC CCAACTTGCCACTGA GCTGAGCATCGCCGA GGGCCAGGAAGTACT ATTTGGGGTCTTTGT 1080
Ron-V1 GCAGGTGGCCCACTC CGCTCCAGTGGGTGC CCAACTTGCCACTGA GCTGAGCATCGCCGA GGGCCAGGAAGTACT ATTTGGGGTCTTTGT 1080
Ron    GCAGGTGGCCCACTC CGCTCCAGTGGGTGC CCAACTTGCCACTGA GCTGAGCATCGCCGA GGGCCAGGAAGTACT ATTTGGGGTCTTTGT 1080

Ron-V3 GACTGGCAAGGATGG TGGTCCTGGCGTGGG CCCCAACTCTGTCGT CTGTGCCTTCCCCAT TGACCTGCTGGACAC ACTAATTGATGAGGG 1170
Ron-V2 GACTGGCAAGGATGG TGGTCCTGGCGTGGG CCCCAACTCTGTCGT CTGTGCCTTCCCCAT TGACCTGCTGGACAC ACTAATTGATGAGGG 1170
Ron-V1 GACTGGCAAGGATGG TGGTCCTGGCGTGGG CCCCAACTCTGTCGT CTGTGCCTTCCCCAT TGACCTGCTGGACAC ACTAATTGATGAGGG 1170
Ron    GACTGGCAAGGATGG TGGTCCTGGCGTGGG CCCCAACTCTGTCGT CTGTGCCTTCCCCAT TGACCTGCTGGACAC ACTAATTGATGAGGG 1170

Ron-V3 TGTGGAGCGCTGTTG TGAATCCCCAGTCCA TCCAGGCCTCCGGCG AGGCCTCGACTTCTT CCAGTCGCCCAGTTT TTGCCCCAACCCGCC 1260
Ron-V2 TGTGGAGCGCTGTTG TGAATCCCCAGTCCA TCCAGGCCTCCGGCG AGGCCTCGACTTCTT CCAGTCGCCCAGTTT TTGCCCCAACCCGCC 1260
Ron-V1 TGTGGAGCGCTGTTG TGAATCCCCAGTCCA TCCAGGCCTCCGGCG AGGCCTCGACTTCTT CCAGTCGCCCAGTTT TTGCCCCAACCCGCC 1260
Ron    TGTGGAGCGCTGTTG TGAATCCCCAGTCCA TCCAGGCCTCCGGCG AGGCCTCGACTTCTT CCAGTCGCCCAGTTT TTGCCCCAACCCGCC 1260

Ron-V3 TGGCCTGGAAGCCCT CAGCCCCAACACCAG CTGCCGCCACTTCCC TCTGCTGGTCAGTAG CAGCTTCTCACGTGT GGACCTATTCAATGG 1350
Ron-V2 TGGCCTGGAAGCCCT CAGCCCCAACACCAG CTGCCGCCACTTCCC TCTGCTGGTCAGTAG CAGCTTCTCACGTGT GGACCTATTCAATGG 1350
Ron-V1 TGGCCTGGAAGCCCT CAGCCCCAACACCAG CTGCCGCCACTTCCC TCTGCTGGTCAGTAG CAGCTTCTCACGTGT GGACCTATTCAATGG 1350
Ron    TGGCCTGGAAGCCCT CAGCCCCAACACCAG CTGCCGCCACTTCCC TCTGCTGGTCAGTAG CAGCTTCTCACGTGT GGACCTATTCAATGG 1350
```

FIG. 5-4 SEQ ID NOs: 2, 4, 6, 8 cont.

```
Ron-V3 GCTGTTGGGACCAGT ACAGGTCACTGCATT GTATGTGACACGCCT TGACAACGTCACAGT GGCACACATGGGCAC AATGGATGGGCGTAT 1440
Ron-V2 GCTGTTGGGACCAGT ACAGGTCACTGCATT GTATGTGACACGCCT TGACAACGTCACAGT GGCACACATGGGCAC AATGGATGGGCGTAT 1440
Ron-V1 GCTGTTGGGACCAGT ACAGGTCACTGCATT GTATGTGACACGCCT TGACAACGTCACAGT GGCACACATGGGCAC AATGGATGGGCGTAT 1440
Ron    GCTGTTGGGACCAGT ACAGGTCACTGCATT GTATGTGACACGCCT TGACAACGTCACAGT GGCACACATGGGCAC AATGGATGGGCGTAT 1440

Ron-V3 CCTGCAGGTGGAGCT GGTCAGGTCACTAAA CTACTTGCTGTATGT GTCCAACTTCTCACT GGGTGACAGTGGGCA GCCCGTGCAGCGGGA 1530
Ron-V2 CCTGCAGGTGGAGCT GGTCAGGTCACTAAA CTACTTGCTGTATGT GTCCAACTTCTCACT GGGTGACAGTGGGCA GCCCGTGCAGCGGGA 1530
Ron-V1 CCTGCAGGTGGAGCT GGTCAGGTCACTAAA CTACTTGCTGTATGT GTCCAACTTCTCACT GGGTGACAGTGGGCA GCCCGTGCAGCGGGA 1530
Ron    CCTGCAGGTGGAGCT GGTCAGGTCACTAAA CTACTTGCTGTATGT GTCCAACTTCTCACT GGGTGACAGTGGGCA GCCCGTGCAGCGGGA 1530

Ron-V3 TGTCAGTCGTCTTGG GGACCACCTACTCTT TGCCTCTGGGGACCA GGTTTTCCAGGTACC TATCCGAGGCCCTGG CTGCCGCCACTTCCT 1620
Ron-V2 TGTCAGTCGTCTTGG GGACCACCTACTCTT TGCCTCTGGGGACCA GGTTTTCCAGGTACC TATCCGAGGCCCTGG CTGCCGCCACTTCCT 1620
Ron-V1 TGTCAGTCGTCTTGG GGACCACCTACTCTT TGCCTCTGGGGACCA GGTTTTCCAGGTACC TATCCGAGGCCCTGG CTGCCGCCACTTCCT 1620
Ron    TGTCAGTCGTCTTGG GGACCACCTACTCTT TGCCTCTGGGGACCA GGTTTTCCAGGTACC TATCCGAGGCCCTGG CTGCCGCCACTTCCT 1620

Ron-V3 GACCTGTGGGCGTTG CCTAAGGGCATGGCA TTTCATGGGCTGTGG CTGGTGTGGGAACAT GTGCGGCCAGCAGAA GGAGTGTCCTGGCTC 1710
Ron-V2 GACCTGTGGGCGTTG CCTAAGGGCATGGCA TTTCATGGGCTGTGG CTGGTGTGGGAACAT GTGCGGCCAGCAGAA GGAGTGTCCTGGCTC 1710
Ron-V1 GACCTGTGGGCGTTG CCTAAGGGCATGGCA TTTCATGGGCTGTGG CTGGTGTGGGAACAT GTGCGGCCAGCAGAA GGAGTGTCCTGGCTC 1710
Ron    GACCTGTGGGCGTTG CCTAAGGGCATGGCA TTTCATGGGCTGTGG CTGGTGTGGGAACAT GTGCGGCCAGCAGAA GGAGTGTCCTGGCTC 1710

Ron-V3 CTGGCAACAGGACCA CTGCCCACCTAAGCT TACTGAGTTCCACCC CCACAGTGGACCTCT AAGGGGCAGTACAAG GCTGACCCTGTGTGG 1800
Ron-V2 CTGGCAACAGGACCA CTGCCCACCTAAGCT TACTGAGTTCCACCC CCACAGTGGACCTCT AAGGGGCAGTACAAG GCTGACCCTGTGTGG 1800
Ron-V1 CTGGCAACAGGACCA CTGCCCACCTAAGCT TACTGAGTTCCACCC CCACAGTGGACCTCT AAGGGGCAGTACAAG GCTGACCCTGTGTGG 1800
Ron    CTGGCAACAGGACCA CTGCCCACCTAAGCT TACTGAGTTCCACCC CCACAGTGGACCTCT AAGGGGCAGTACAAG GCTGACCCTGTGTGG 1800
```

FIG. 5-5 SEQ ID NOs: 2, 4, 6, 8 cont.

```
Ron-V3 CTCCAACTTCTACCT TCACCCTTCTGGTCT GGTGCCTGAGGGAAC CCATCAGGTCACTGT GGGCCAAAGTCCCTG CCGGCCACTGCCCAA 1890
Ron-V2 CTCCAACTTCTACCT TCACCCTTCTGGTCT GGTGCCTGAGGGAAC CCATCAGGTCACTGT GGGCCAAAGTCCCTG CCGGCCACTGCCCAA 1890
Ron-V1 CTCCAACTTCTACCT TCACCCTTCTGGTCT GGTGCCTGAGGGAAC CCATCAGGTCACTGT GGGCCAAAGTCCCTG CCGGCCACTGCCCAA 1890
Ron    CTCCAACTTCTACCT TCACCCTTCTGGTCT GGTGCCTGAGGGAAC CCATCAGGTCACTGT GGGCCAAAGTCCCTG CCGGCCACTGCCCAA 1890

Ron-V3 GGACAGCTCAAAACT CAGACCAGTGCCCCG GAAAGACTTTGTAGA GGAGTTTGAGTGTGA ACTGGAGCCCTTGGG CACCCAGGCAGTGGG 1980
Ron-V2 GGACAGCTCAAAACT CAGACCAGTGCCCCG GAAAGACTTTGTAGA GGAGTTTGAGTGTGA ACTGGAGCCCTTGGG CACCCAGGCAGTGGG 1980
Ron-V1 GGACAGCTCAAAACT CAGACCAGTGCCCCG GAAAGACTTTGTAGA GGAGTTTGAGTGTGA ACTGGAGCCCTTGGG CACCCAGGCAGTGGG 1980
Ron    GGACAGCTCAAAACT CAGACCAGTGCCCCG GAAAGACTTTGTAGA GGAGTTTGAGTGTGA ACTGGAGCCCTTGGG CACCCAGGCAGTGGG 1980

Ron-V3 GCCTACCAACGTCAG CCTCACCGTGACTAA CATGCCACCGGGCAA GCACTTCCGGGTAGA CGGCACCTCCGTGCT GAGAGGCTTCTCTTT 2070
Ron-V2 GCCTACCAACGTCAG CCTCACCGTGACTAA CATGCCACCGGGCAA GCACTTCCGGGTAGA CGGCACCTCCGTGCT GAGAGGCTTCTCTTT 2070
Ron-V1 GCCTACCAACGTCAG CCTCACCGTGACTAA CATGCCACCGGGCAA GCACTTCCGGGTAGA CGGCACCTCCGTGCT GAGAGGCTTCTCTTT 2070
Ron    GCCTACCAACGTCAG CCTCACCGTGACTAA CATGCCACCGGGCAA GCACTTCCGGGTAGA CGGCACCTCCGTGCT GAGAGGCTTCTCTTT 2070

Ron-V3 CATGGAGCCAGTGCT GATAGCAGTGCAACC CCTCTTTGGCCCACG GGCAGGAGGCACCTG TCTCACTCTTGAAGG CCAGAGTCTGTCTGT 2160
Ron-V2 CATGGAGCCAGTGCT GATAGCAGTGCAACC CCTCTTTGGCCCACG GGCAGGAGGCACCTG TCTCACTCTTGAAGG CCAGAGTCTGTCTGT 2160
Ron-V1 CATGGAGCCAGTGCT GATAGCAGTGCAACC CCTCTTTGGCCCACG GGCAGGAGGCACCTG TCTCACTCTTGAAGG CCAGAGTCTGTCTGT 2160
Ron    CATGGAGCCAGTGCT GATAGCAGTGCAACC CCTCTTTGGCCCACG GGCAGGAGGCACCTG TCTCACTCTTGAAGG CCAGAGTCTGTCTGT 2160

Ron-V3 AGGCACCAGCCGGGC TGTGCTGGTCAATGG GACTGAGTGTCTGCT AGCACGGGTCAGTGA GGGGCAGCTTTTATG TGCCACACCCCCTGG 2250
Ron-V2 AGGCACCAGCCGGGC TGTGCTGGTCAATGG GACTGAGTGTCTGCT AGCACGGGTCAGTGA GGGGCAGCTTTTATG TGCCACACCCCCTGG 2250
Ron-V1 AGGCACCAGCCGGGC TGTGCTGGTCAATGG GACTGAGTGTCTGCT AGCACGGGTCAGTGA GGGGCAGCTTTTATG TGCCACACCCCCTGG 2250
Ron    AGGCACCAGCCGGGC TGTGCTGGTCAATGG GACTGAGTGTCTGCT AGCACGGGTCAGTGA GGGGCAGCTTTTATG TGCCACACCCCCTGG 2250
```

FIG. 5-6 SEQ ID NOs: 2, 4, 6, 8 cont.

```
Ron-V3 GGCCACGGTGGCCAG TGTCCCCCTTAGCCT GCAGGTGGGGGGTGC CCAGGTACCTGGTTC CTGGACCTTCCAGTA CAGAGAAGACCCTGT 2340
Ron-V2 GGCCACGGTGGCCAG TGTCCCCCTTAGCCT GCAGGTGGGGGGTGC CCAGGTACCTGGTTC CTGGACCTTCCAGTA CAGAGAAGACCCTGT 2340
Ron-V1 GGCCACGGTGGCCAG TGTCCCCCTTAGCCT GCAGGTGGGGGGTGC CCAGGTACCTGGTTC CTGGACCTTCCAGTA CAGAGAAGACCCTGT 2340
Ron    GGCCACGGTGGCCAG TGTCCCCCTTAGCCT GCAGGTGGGGGGTGC CCAGGTACCTGGTTC CTGGACCTTCCAGTA CAGAGAAGACCCTGT 2340

Ron-V3 CGTGCTAAGCATCAG CCCCAACTGTGGCTA CATCAACTCCCACAT CACCATCTGTGGCCA GCATCTAACTTCAGC ATGGCACTTAGTGCT 2430
Ron-V2 CGTGCTAAGCATCAG CCCCAACTGTGGCTA CATCAACTCCCACAT CACCATCTGTGGCCA GCATCTAACTTCAGC ATGGCACTTAGTGCT 2430
Ron-V1 CGTGCTAAGCATCAG CCCCAACTGTGGCTA CATCAACTCCCACAT CACCATCTGTGGCCA GCATCTAACTTCAGC ATGGCACTTAGTGCT 2430
Ron    CGTGCTAAGCATCAG CCCCAACTGTGGCTA CATCAACTCCCACAT CACCATCTGTGGCCA GCATCTAACTTCAGC ATGGCACTTAGTGCT 2430

Ron-V3 GTCATTCCATGACGG GCTTAGGGCAGTGGA AAGCAGGTGTGAGAG GCAGCTTCCAGAGCA GCAGCTGTGCCGCCT TCCTGAATATGTGGT 2520
Ron-V2 GTCATTCCATGACGG GCTTAGGGCAGTGGA AAGCAGGTGTGAGAG GCAGCTTCCAGAGCA GCAGCTGTGCCGCCT TCCTGAATATGTGGT 2520
Ron-V1 GTCATTCCATGACGG GCTTAGGGCAGTGGA AAGCAGGTGTGAGAG GCAGCTTCCAGAGCA GCAGCTGTGCCGCCT TCCTGAATATGTGGT 2520
Ron    GTCATTCCATGACGG GCTTAGGGCAGTGGA AAGCAGGTGTGAGAG GCAGCTTCCAGAGCA GCAGCTGTGCCGCCT TCCTGAATATGTGGT 2520

Ron-V3 CCGAGACCCCCAGGG ATGGGTGGCAGGGAA TCTGAGTGCCCGAGG GGATGGAGCTGCTGG CTTTACACTGCCTGG CTTTCGCTTCCTACC 2610
Ron-V2 CCGAGACCCCCAGGG ATGGGTGGCAGGGAA TCTGAGTGCCCGAGG GGATGGAGCTGCTGG CTTTACACTGCCTGG CTTTCGCTTCCTACC 2610
Ron-V1 CCGAGACCCCCAGGG ATGGGTGGCAGGGAA TCTGAGTGCCCGAGG GGATGGAGCTGCTGG CTTTACACTGCCTGG CTTTCGCTTCCTACC 2610
Ron    CCGAGACCCCCAGGG ATGGGTGGCAGGGAA TCTGAGTGCCCGAGG GGATGGAGCTGCTGG CTTTACACTGCCTGG CTTTCGCTTCCTACC 2610

Ron-V3 CCCACCCCATCCACC CAGTGCCAACCTAGT TCCACTGAAGCCTGA GGAGCATGCCATTAA GTTTGAG-------- --------------- 2690
Ron-V2 CCCACCCCATCCACC CAGTGCCAACCTAGT TCCACTGAAGCCTGA GGAGCATGCCATTAA GTTTGAG-------- --------------- 2677
Ron-V1 CCCACCCCATCCACC CAGTGCCAACCTAGT TCCACTGAAGCCTGA GGAGCATGCCATTAA GTTTGAGTATATTGG GCTGGGCGCTGTGGC 2700
Ron    CCCACCCCATCCACC CAGTGCCAACCTAGT TCCACTGAAGCCTGA GGAGCATGCCATTAA GTTTGAGTATATTGG GCTGGGCGCTGTGGC 2700
```

FIG. 5-7 SEQ ID NOs: 2, 4, 6, 8 cont.

```
Ron-V3 --------------- --------------- --------------- --------------- --------------- ---------------  2690
Ron-V2 --------------- --------------- --------------- --------------- --------------- ---------------  2677
Ron-V1 TGACTGTGTGGGTAT CAACGTGACCGTGGG TGGTGAGAGCTGCCA GCACGAGTTCCGGGG GGACATGGTTGTCTG CCCCCTGCCCCCATC  2790
Ron    TGACTGTGTGGGTAT CAACGTGACCGTGGG TGGTGAGAGCTGCCA GCACGAGTTCCGGGG GGACATGGTTGTCTG CCCCCTGCCCCCATC  2790

Ron-V3 --------------- --------------- ----GTCTGCGTAGA TG------------- --------------- ---------------  2690
Ron-V2 -------CTTGGCCA GGATGGTGCCCCATT GCAGGTCTGCGTAGA TG------------- --------------- ---------------  2717
Ron-V1 CCTGCAGCTTGGCCA GGATGGTGCCCCATT GCAGGTCTGCGTAGA TG------------- --------------- ---------------  2837
Ron    CCTGCAGCTTGGCCA GGATGGTGCCCCATT GCAGGTCTGCGTAGA TGGTGAATGTCATAT CCTGGGTAGAGTGGT GCGGCCAGGGCCAGA  2880

Ron-V3 --------------- --------------- --------------- --------------- --------------- ---------------  2690
Ron-V2 --------------- --------------- --------------- --------------- --------------- ---------------  2717
Ron-V1 --------------- --------------- --------------- --------------- --------------- ---------------  2837
Ron    TGGGGTCCCACAGAG CACGCTCCTTGGTAT CCTGCTGCCTTTGCT GCTGCTTGTGGCTGC ACTGGCGACTGCACT GGTCTTCAGCTACTG  2970

Ron-V3 --------------- --------------- --------------- --------------- --------------- ---------------  2690
Ron-V2 --------------- --------------- --------------- --------------- --------------- ---------------  2717
Ron-V1 --------------- --------------- --------------- --------------- --------------- ---------------  2837
Ron    GTGGCGGAGGAAGCA GCTAGTTCTTCCTCC CAACCTGAATGACCT GGCATCCCTGGACCA GACTGCTGGAGCCAC ACCCCTGCCTATTCT  3060

Ron-V3 --------------- --------------- --CACTCCCTGCCAT TGATGGTCTGGATTC CACCACTTGTGTCCA TGGAGCATCCTTCTC  2748
Ron-V2 --------------- --------------- --CACTCCCTGCCAT TGATGGTCTGGATTC CACCACTTGTGTCCA TGGAGCATCCTTCTC  2775
Ron-V1 --------------- --------------- --CACTCCCTGCCAT TGATGGTCTGGATTC CACCACTTGTGTCCA TGGAGCATCCTTCTC  2895
Ron    GTACTCGGGCTCTGA CTACAGAAGTGGCCT TGCACTCCCTGCCAT TGATGGTCTGGATTC CACCACTTGTGTCCA TGGAGCATCCTTCTC  3150
```

FIG. 5-8 SEQ ID NOs: 2, 4, 6, 8 cont.

```
Ron-V3 CGATAGTGAAGATGA ATCCTGTGTGCCACT GCTGCGGAAAGAGTC CATCCAGCTAAGGGA CCTGGACTCTGCGCT CTTGGCTGAGGTCAA  2838
Ron-V2 CGATAGTGAAGATGA ATCCTGTGTGCCACT GCTGCGGAAAGAGTC CATCCAGCTAAGGGA CCTGGACTCTGCGCT CTTGGCTGAGGTCAA  2865
Ron-V1 CGATAGTGAAGATGA ATCCTGTGTGCCACT GCTGCGGAAAGAGTC CATCCAGCTAAGGGA CCTGGACTCTGCGCT CTTGGCTGAGGTCAA  2985
Ron    CGATAGTGAAGATGA ATCCTGTGTGCCACT GCTGCGGAAAGAGTC CATCCAGCTAAGGGA CCTGGACTCTGCGCT CTTGGCTGAGGTCAA  3240

Ron-V3 GGATGTGCTGATTCC CCATGAGCGGGTGGT CACCCACAGTGACCG AGTCATTGGCAAAGG CCACTTTGGAGTTGT CTACCACGGAGAATA  2928
Ron-V2 GGATGTGCTGATTCC CCATGAGCGGGTGGT CACCCACAGTGACCG AGTCATTGGCAAAGG CCACTTTGGAGTTGT CTACCACGGAGAATA  2955
Ron-V1 GGATGTGCTGATTCC CCATGAGCGGGTGGT CACCCACAGTGACCG AGTCATTGGCAAAGG CCACTTTGGAGTTGT CTACCACGGAGAATA  3075
Ron    GGATGTGCTGATTCC CCATGAGCGGGTGGT CACCCACAGTGACCG AGTCATTGGCAAAGG CCACTTTGGAGTTGT CTACCACGGAGAATA  3330

Ron-V3 CATAGACCAGGCCCA GAATCGAATCCAATG TGCCATCAAGTCACT AAGTCGCATCACAGA GATGCAGCAGGTGGA GGCCTTCCTGCGAGA  3018
Ron-V2 CATAGACCAGGCCCA GAATCGAATCCAATG TGCCATCAAGTCACT AAGTCGCATCACAGA GATGCAGCAGGTGGA GGCCTTCCTGCGAGA  3045
Ron-V1 CATAGACCAGGCCCA GAATCGAATCCAATG TGCCATCAAGTCACT AAGTCGCATCACAGA GATGCAGCAGGTGGA GGCCTTCCTGCGAGA  3165
Ron    CATAGACCAGGCCCA GAATCGAATCCAATG TGCCATCAAGTCACT AAGTCGCATCACAGA GATGCAGCAGGTGGA GGCCTTCCTGCGAGA  3420

Ron-V3 GGGGCTGCTCATGCG TGGCCTGAACCACCC GAATGTGCTGGCTCT CATTGGTATCATGTT GCCACCTGAGGGCCT GCCCCATGTGCTGCT  3108
Ron-V2 GGGGCTGCTCATGCG TGGCCTGAACCACCC GAATGTGCTGGCTCT CATTGGTATCATGTT GCCACCTGAGGGCCT GCCCCATGTGCTGCT  3135
Ron-V1 GGGGCTGCTCATGCG TGGCCTGAACCACCC GAATGTGCTGGCTCT CATTGGTATCATGTT GCCACCTGAGGGCCT GCCCCATGTGCTGCT  3255
Ron    GGGGCTGCTCATGCG TGGCCTGAACCACCC GAATGTGCTGGCTCT CATTGGTATCATGTT GCCACCTGAGGGCCT GCCCCATGTGCTGCT  3510

Ron-V3 GCCCTATATGTGCCA CGGTGACCTGCTCCA GTTCATCCGCTCACC TCAGCGGAACCCCAC CGTGAAGGACCTCAT CAGCTTTGGCCTGCA  3198
Ron-V2 GCCCTATATGTGCCA CGGTGACCTGCTCCA GTTCATCCGCTCACC TCAGCGGAACCCCAC CGTGAAGGACCTCAT CAGCTTTGGCCTGCA  3225
Ron-V1 GCCCTATATGTGCCA CGGTGACCTGCTCCA GTTCATCCGCTCACC TCAGCGGAACCCCAC CGTGAAGGACCTCAT CAGCTTTGGCCTGCA  3345
Ron    GCCCTATATGTGCCA CGGTGACCTGCTCCA GTTCATCCGCTCACC TCAGCGGAACCCCAC CGTGAAGGACCTCAT CAGCTTTGGCCTGCA  3600
```

FIG. 5-9 SEQ ID NOs: 2, 4, 6, 8 cont.

```
Ron-V3 GGTAGCCCGCGGCAT GGAGTACCTGGCAGA GCAGAAGTTTGTGCA CAGGGACCTGGCTGC GCGGAACTGCATGCT GGACGAGTCATTCAC 3288
Ron-V2 GGTAGCCCGCGGCAT GGAGTACCTGGCAGA GCAGAAGTTTGTGCA CAGGGACCTGGCTGC GCGGAACTGCATGCT GGACGAGTCATTCAC 3315
Ron-V1 GGTAGCCCGCGGCAT GGAGTACCTGGCAGA GCAGAAGTTTGTGCA CAGGGACCTGGCTGC GCGGAACTGCATGCT GGACGAGTCATTCAC 3435
Ron    GGTAGCCCGCGGCAT GGAGTACCTGGCAGA GCAGAAGTTTGTGCA CAGGGACCTGGCTGC GCGGAACTGCATGCT GGACGAGTCATTCAC 3690

Ron-V3 AGTCAAGGTGGCTGA CTTTGGTTTGGCCCG CGACATCCTGGACAG GGAGTACTATAGTGT TCAACAGCATCGCCA CGCTCGCCTACCTGT 3378
Ron-V2 AGTCAAGGTGGCTGA CTTTGGTTTGGCCCG CGACATCCTGGACAG GGAGTACTATAGTGT TCAACAGCATCGCCA CGCTCGCCTACCTGT 3405
Ron-V1 AGTCAAGGTGGCTGA CTTTGGTTTGGCCCG CGACATCCTGGACAG GGAGTACTATAGTGT TCAACAGCATCGCCA CGCTCGCCTACCTGT 3525
Ron    AGTCAAGGTGGCTGA CTTTGGTTTGGCCCG CGACATCCTGGACAG GGAGTACTATAGTGT TCAACAGCATCGCCA CGCTCGCCTACCTGT 3780

Ron-V3 GAAGTGGATGGCGCT GGAGAGCCTGCAGAC CTATAGATTTACCAC CAAGTCTGATGTG-- --------------- --------------- 3436
Ron-V2 GAAGTGGATGGCGCT GGAGAGCCTGCAGAC CTATAGATTTACCAC CAAGTCTGATGTG-- --------------- --------------- 3463
Ron-V1 GAAGTGGATGGCGCT GGAGAGCCTGCAGAC CTATAGATTTACCAC CAAGTCTGATGTG-- --------------- --------------- 3583
Ron    GAAGTGGATGGCGCT GGAGAGCCTGCAGAC CTATAGATTTACCAC CAAGTCTGATGTGTG GTCATTTGGTGTGCT GCTGTGGGAACTGCT 3870

Ron-V3 --------------- --------------- --------------- --------------- --------------- --------------- 3436
Ron-V2 --------------- --------------- --------------- --------------- --------------- --------------- 3463
Ron-V1 --------------- --------------- --------------- --------------- --------------- --------------- 3583
Ron    GACACGGGGTGCCCC ACCATACCGCCACAT TGACCCTTTTGACCT TACCCACTTCCTGGC CCAGGGTCGGCGCCT GCCCCAGCCTGAGTA 3960

Ron-V3 --------------- GTACCAAGTGATGCA GCAATGCTGGGAGGC AGACCCAGCAGTGCG ACCCACCTTCAGAGT ACTAGTGGGGGAGGT 3511
Ron-V2 --------------- GTACCAAGTGATGCA GCAATGCTGGGAGGC AGACCCAGCAGTGCG ACCCACCTTCAGAGT ACTAGTGGGGGAGGT 3538
Ron-V1 --------------- GTACCAAGTGATGCA GCAATGCTGGGAGGC AGACCCAGCAGTGCG ACCCACCTTCAGAGT ACTAGTGGGGGAGGT 3658
Ron    TTGCCCTGATTCTCT GTACCAAGTGATGCA GCAATGCTGGGAGGC AGACCCAGCAGTGCG ACCCACCTTCAGAGT ACTAGTGGGGGAGGT 4050
```

FIG. 5-10 SEQ ID NOs: 2, 4, 6, 8 cont.

```
Ron-V3 GGAGCAGATAGTGTC TGCACTGCTTGGGGA CCATTATGTGCAGCT GCCAGCAACCTACAT GAACTTG-------- ---------------  3578
Ron-V2 GGAGCAGATAGTGTC TGCACTGCTTGGGGA CCATTATGTGCAGCT GCCAGCAACCTACAT GAACTTG-------- ---------------  3605
Ron-V1 GGAGCAGATAGTGTC TGCACTGCTTGGGGA CCATTATGTGCAGCT GCCAGCAACCTACAT GAACTTG-------- ---------------  3725
Ron    GGAGCAGATAGTGTC TGCACTGCTTGGGGA CCATTATGTGCAGCT GCCAGCAACCTACAT GAACTTGGGCCCCAG CACCTCGCATGAGAT  4140

Ron-V3 --------------- --------------- --------------- --------------- --------------- ---------------  3578
Ron-V2 --------------- --------------- --------------- --------------- --------------- ---------------  3605
Ron-V1 --------------- --------------- --------------- --------------- --------------- ---------------  3725
Ron    GAATGTGCGTCCAGA ACAGCCGCAGTTCTC ACCCATGCCAGGGAA TGTACGCCGGCCCCG GCCACTCTCAGAGCC TCCTCGGCCCACTTG  4230

Ron-V3 --------------- --------------- ------AGCTAACCC CAAGGCTGCCTCTGG GCCATGCCAGGCCAG AGCAGTGGCCCTCCA  3632
Ron-V2 --------------- --------------- ------AGCTAACCC CAAGGCTGCCTCTGG GCCATGCCAGGCCAG AGCAGTGGCCCTCCA  3659
Ron-V1 --------------- --------------- ------AGCTAACCC CAAGGCTGCCTCTGG GCCATGCCAGGCCAG AGCAGTGGCCCTCCA  3779
Ron    ACTTAGTTCTTGGGC TGGACCTGCTTAGCT GCCTTGAGCTAACCC CAAGGCTGCCTCTGG GCCATGCCAGGCCAG AGCAGTGGCCCTCCA  4320

Ron-V3 CCTTGTTCCTGCCCT TTAACTTTCAGAGGC AATAGGTAAATGGGC CCATTAGGTCCCTCA CTCCACAGAGTGAGC CAGTGAGGGCAGTCC  3722
Ron-V2 CCTTGTTCCTGCCCT TTAACTTTCAGAGGC AATAGGTAAATGGGC CCATTAGGTCCCTCA CTCCACAGAGTGAGC CAGTGAGGGCAGTCC  3749
Ron-V1 CCTTGTTCCTGCCCT TTAACTTTCAGAGGC AATAGGTAAATGGGC CCATTAGGTCCCTCA CTCCACAGAGTGAGC CAGTGAGGGCAGTCC  3869
Ron    CCTTGTTCCTGCCCT TTAACTTTCAGAGGC AATAGGTAAATGGGC CCATTAGGTCCCTCA CTCCACAGAGTGAGC CAGTGAGGGCAGTCC  4410

Ron-V3 TGCAACATGTATTTA TGGAGTGCCTGCTGT GGACCCTGTCTTCTG GGCACAGTGGACTCA GCAGTGACCACACCA ACACTGACCCTTGAA  3812
Ron-V2 TGCAACATGTATTTA TGGAGTGCCTGCTGT GGACCCTGTCTTCTG GGCACAGTGGACTCA GCAGTGACCACACCA ACACTGACCCTTGAA  3839
Ron-V1 TGCAACATGTATTTA TGGAGTGCCTGCTGT GGACCCTGTCTTCTG GGCACAGTGGACTCA GCAGTGACCACACCA ACACTGACCCTTGAA  3959
Ron    TGCAACATGTATTTA TGGAGTGCCTGCTGT GGACCCTGTCTTCTG GGCACAGTGGACTCA GCAGTGACCACACCA ACACTGACCCTTGAA  4500
```

FIG. 5-11 SEQ ID NOs: 2, 4, 6, 8 cont.

```
Ron-V3 CCAATAAAGGAACAA ATGACTATTAAAGCA CAAAAAAAAAA   3853
Ron-V2 CCAATAAAGGAACAA ATGACTATTAAAGCA CAAAAAAAAAA   3880
Ron-V1 CCAATAAAGGAACAA ATGACTATTAAAGCA CAAAAAAAAAA   4000
Ron    CCAATAAAGGAACAA ATGACTATTAAAGCA CAAAAAAAAAA   4541
```

FIG. 6-1

```
Ron-V3  MELLPPLPQSFLLLL LLPAKPAAGEDWQCP RTPYAASRDFDVKYV VPSFSAGGLVQAMVT YEGDRNESAVFVAIR NRLHVLGPDLKSVQS   90
Ron-V2  MELLPPLPQSFLLLL LLPAKPAAGEDWQCP RTPYAASRDFDVKYV VPSFSAGGLVQAMVT YEGDRNESAVFVAIR NRLHVLGPDLKSVQS   90
Ron-V1  MELLPPLPQSFLLLL LLPAKPAAGEDWQCP RTPYAASRDFDVKYV VPSFSAGGLVQAMVT YEGDRNESAVFVAIR NRLHVLGPDLKSVQS   90
Ron     MELLPPLPQSFLLLL LLPAKPAAGEDWQCP RTPYAASRDFDVKYV VPSFSAGGLVQAMVT YEGDRNESAVFVAIR NRLHVLGPDLKSVQS   90

Ron-V3  LATGPAGDPGCQTCA ACGPGPHGPPGDTDT KVLVLDPALPALVSC GSSLQGRCFLHDLEP QGTAVHLAAPACLFS AHHNRPDDCPDCVAS  180
Ron-V2  LATGPAGDPGCQTCA ACGPGPHGPPGDTDT KVLVLDPALPALVSC GSSLQGRCFLHDLEP QGTAVHLAAPACLFS AHHNRPDDCPDCVAS  180
Ron-V1  LATGPAGDPGCQTCA ACGPGPHGPPGDTDT KVLVLDPALPALVSC GSSLQGRCFLHDLEP QGTAVHLAAPACLFS AHHNRPDDCPDCVAS  180
Ron     LATGPAGDPGCQTCA ACGPGPHGPPGDTDT KVLVLDPALPALVSC GSSLQGRCFLHDLEP QGTAVHLAAPACLFS AHHNRPDDCPDCVAS  180

Ron-V3  PLGTRVTVVEQGQAS YFYVASSLDAAVAGS FSPRSVSIRRLKADA SGFAPGFVALSVLPK HLVSYSIEYVHSFHT GAFVYFLTVQPASVT  270
Ron-V2  PLGTRVTVVEQGQAS YFYVASSLDAAVAGS FSPRSVSIRRLKADA SGFAPGFVALSVLPK HLVSYSIEYVHSFHT GAFVYFLTVQPASVT  270
Ron-V1  PLGTRVTVVEQGQAS YFYVASSLDAAVAGS FSPRSVSIRRLKADA SGFAPGFVALSVLPK HLVSYSIEYVHSFHT GAFVYFLTVQPASVT  270
Ron     PLGTRVTVVEQGQAS YFYVASSLDAAVAGS FSPRSVSIRRLKADA SGFAPGFVALSVLPK HLVSYSIEYVHSFHT GAFVYFLTVQPASVT  270

Ron-V3  DDPSALHTRLARLSA TEPELGDYRELVLDC RFAPKRRRRGAPEGG QPYPVLQVAHSAPVG AQLATELSIAEGQEV LFGVFVTGKDGGPGV  360
Ron-V2  DDPSALHTRLARLSA TEPELGDYRELVLDC RFAPKRRRRGAPEGG QPYPVLQVAHSAPVG AQLATELSIAEGQEV LFGVFVTGKDGGPGV  360
Ron-V1  DDPSALHTRLARLSA TEPELGDYRELVLDC RFAPKRRRRGAPEGG QPYPVLQVAHSAPVG AQLATELSIAEGQEV LFGVFVTGKDGGPGV  360
Ron     DDPSALHTRLARLSA TEPELGDYRELVLDC RFAPKRRRRGAPEGG QPYPVLQVAHSAPVG AQLATELSIAEGQEV LFGVFVTGKDGGPGV  360

Ron-V3  GPNSVVCAFPIDLLD TLIDEGVERCCESPV HPGLRRGLDFFQSPS FCPNPPGLEALSPNT SCRHFPLLVSSSFSR VDLFNGLLGPVQVTA  450
Ron-V2  GPNSVVCAFPIDLLD TLIDEGVERCCESPV HPGLRRGLDFFQSPS FCPNPPGLEALSPNT SCRHFPLLVSSSFSR VDLFNGLLGPVQVTA  450
Ron-V1  GPNSVVCAFPIDLLD TLIDEGVERCCESPV HPGLRRGLDFFQSPS FCPNPPGLEALSPNT SCRHFPLLVSSSFSR VDLFNGLLGPVQVTA  450
Ron     GPNSVVCAFPIDLLD TLIDEGVERCCESPV HPGLRRGLDFFQSPS FCPNPPGLEALSPNT SCRHFPLLVSSSFSR VDLFNGLLGPVQVTA  450
```

FIG. 6-2

```
Ron-V3  LYVTRLDNVTVAHMG TMDGRILQVELVRSL NYLLYVSNFSLGDSG QPVQRDVSRLGDHLL FASGDQVFQVPIRGP GCRHFLTCGRCLRAW  540
Ron-V2  LYVTRLDNVTVAHMG TMDGRILQVELVRSL NYLLYVSNFSLGDSG QPVQRDVSRLGDHLL FASGDQVFQVPIRGP GCRHFLTCGRCLRAW  540
Ron-V1  LYVTRLDNVTVAHMG TMDGRILQVELVRSL NYLLYVSNFSLGDSG QPVQRDVSRLGDHLL FASGDQVFQVPIRGP GCRHFLTCGRCLRAW  540
Ron     LYVTRLDNVTVAHMG TMDGRILQVELVRSL NYLLYVSNFSLGDSG QPVQRDVSRLGDHLL FASGDQVFQVPIRGP GCRHFLTCGRCLRAW  540

Ron-V3  HFMGCGWCGNMCGQQ KECPGSWQQDHCPPK LTEFHPHSGPLRGST RLTLCGSNFYLHPSG LVPEGTHQVTVGQSP CRPLPKDSSKLRPVP  630
Ron-V2  HFMGCGWCGNMCGQQ KECPGSWQQDHCPPK LTEFHPHSGPLRGST RLTLCGSNFYLHPSG LVPEGTHQVTVGQSP CRPLPKDSSKLRPVP  630
Ron-V1  HFMGCGWCGNMCGQQ KECPGSWQQDHCPPK LTEFHPHSGPLRGST RLTLCGSNFYLHPSG LVPEGTHQVTVGQSP CRPLPKDSSKLRPVP  630
Ron     HFMGCGWCGNMCGQQ KECPGSWQQDHCPPK LTEFHPHSGPLRGST RLTLCGSNFYLHPSG LVPEGTHQVTVGQSP CRPLPKDSSKLRPVP  630

Ron-V3  RKDFVEEFECELEPL GTQAVGPTNVSLTVT NMPPGKHFRVDGTSV LRGFSFMEPVLIAVQ PLFGPRAGGTCLTLE GQSLSVGTSRAVLVN  720
Ron-V2  RKDFVEEFECELEPL GTQAVGPTNVSLTVT NMPPGKHFRVDGTSV LRGFSFMEPVLIAVQ PLFGPRAGGTCLTLE GQSLSVGTSRAVLVN  720
Ron-V1  RKDFVEEFECELEPL GTQAVGPTNVSLTVT NMPPGKHFRVDGTSV LRGFSFMEPVLIAVQ PLFGPRAGGTCLTLE GQSLSVGTSRAVLVN  720
Ron     RKDFVEEFECELEPL GTQAVGPTNVSLTVT NMPPGKHFRVDGTSV LRGFSFMEPVLIAVQ PLFGPRAGGTCLTLE GQSLSVGTSRAVLVN  720

Ron-V3  GTECLLARVSEGQLL CATPPGATVASVPLS LQVGGAQVPGSWTFQ YREDPVVLSISPNCG YINSHITICGQHLTS AWHLVLSFHDGLRAV  810
Ron-V2  GTECLLARVSEGQLL CATPPGATVASVPLS LQVGGAQVPGSWTFQ YREDPVVLSISPNCG YINSHITICGQHLTS AWHLVLSFHDGLRAV  810
Ron-V1  GTECLLARVSEGQLL CATPPGATVASVPLS LQVGGAQVPGSWTFQ YREDPVVLSISPNCG YINSHITICGQHLTS AWHLVLSFHDGLRAV  810
Ron     GTECLLARVSEGQLL CATPPGATVASVPLS LQVGGAQVPGSWTFQ YREDPVVLSISPNCG YINSHITICGQHLTS AWHLVLSFHDGLRAV  810

Ron-V3  ESRCERQLPEQQLCR LPEYVVRDPQGWVAG NLSARGDGAAGFTLP GFRFLPPPHPPSANL VPLKPEEHAIKFE-- ---------------  883
Ron-V2  ESRCERQLPEQQLCR LPEYVVRDPQGWVAG NLSARGDGAAGFTLP GFRFLPPPHPPSANL VPLKPEEHAIKFE-- ---------------  883
Ron-V1  ESRCERQLPEQQLCR LPEYVVRDPQGWVAG NLSARGDGAAGFTLP GFRFLPPPHPPSANL VPLKPEEHAIKFEYI GLGAVADCVGINVTV  900
Ron     ESRCERQLPEQQLCR LPEYVVRDPQGWVAG NLSARGDGAAGFTLP GFRFLPPPHPPSANL VPLKPEEHAIKFEYI GLGAVADCVGINVTV  900
```

FIG. 6-3

```
Ron-V3  --------------- --------------- --VCVD--------- --------------- --------------- ---------------   887
Ron-V2  --------------- --------LGQDGAP LQVCVD--------- --------------- --------------- ---------------   896
Ron-V1  GGESCQHEFRGDMVV CPLPPSLQLGQDGAP LQVCVD--------- --------------- --------------- ---------------   936
Ron     GGESCQHEFRGDMVV CPLPPSLQLGQDGAP LQVCVDGECHILGRV VRPGPDGVPQSTLLG ILLPLLLLVAALATA LVFSYWWRRKQLVLP   990

Ron-V3  --------------- --------------- -ALPAIDGLDSTTCV HGASFSDSEDESCVP LLRKESIQLRDLDSA LLAEVKDVLIPHERV   946
Ron-V2  --------------- --------------- -ALPAIDGLDSTTCV HGASFSDSEDESCVP LLRKESIQLRDLDSA LLAEVKDVLIPHERV   955
Ron-V1  --------------- --------------- -ALPAIDGLDSTTCV HGASFSDSEDESCVP LLRKESIQLRDLDSA LLAEVKDVLIPHERV   995
Ron     PNLNDLASLDQTAGA TPLPILYSGSDYRSG LALPAIDGLDSTTCV HGASFSDSEDESCVP LLRKESIQLRDLDSA LLAEVKDVLIPHERV  1080

Ron-V3  VTHSDRVIGKGHFGV VYHGEYIDQAQNRIQ CAIKSLSRITEMQQV EAFLREGLLMRGLNH PNVLALIGIMLPPEG LPHVLLPYMCHGDLL  1036
Ron-V2  VTHSDRVIGKGHFGV VYHGEYIDQAQNRIQ CAIKSLSRITEMQQV EAFLREGLLMRGLNH PNVLALIGIMLPPEG LPHVLLPYMCHGDLL  1045
Ron-V1  VTHSDRVIGKGHFGV VYHGEYIDQAQNRIQ CAIKSLSRITEMQQV EAFLREGLLMRGLNH PNVLALIGIMLPPEG LPHVLLPYMCHGDLL  1085
Ron     VTHSDRVIGKGHFGV VYHGEYIDQAQNRIQ CAIKSLSRITEMQQV EAFLREGLLMRGLNH PNVLALIGIMLPPEG LPHVLLPYMCHGDLL  1170

Ron-V3  QFIRSPQRNPTVKDL ISFGLQVARGMEYLA EQKFVHRDLAARNCM LDESFTVKVADFGLA RDILDREYYSVQQHR HARLPVKWMALESLQ  1126
Ron-V2  QFIRSPQRNPTVKDL ISFGLQVARGMEYLA EQKFVHRDLAARNCM LDESFTVKVADFGLA RDILDREYYSVQQHR HARLPVKWMALESLQ  1135
Ron-V1  QFIRSPQRNPTVKDL ISFGLQVARGMEYLA EQKFVHRDLAARNCM LDESFTVKVADFGLA RDILDREYYSVQQHR HARLPVKWMALESLQ  1175
Ron     QFIRSPQRNPTVKDL ISFGLQVARGMEYLA EQKFVHRDLAARNCM LDESFTVKVADFGLA RDILDREYYSVQQHR HARLPVKWMALESLQ  1260

Ron-V3  TYRFTTKSDVVPSD- --------------- --------------- --------------- --------------- ----------AAMLG  1145
Ron-V2  TYRFTTKSDVVPSD- --------------- --------------- --------------- --------------- ----------AAMLG  1154
Ron-V1  TYRFTTKSDVVPSD- --------------- --------------- --------------- --------------- ----------AAMLG  1194
Ron     TYRFTTKSDVWSFGV LLWELLTRGAPPYRH IDPFDLTHFLAQGRR LPQPEYCPDSLYQVM QQCWEADPAVRPTFR VLVGEVEQIVSALLG  1350
```

FIG. 6-4

```
Ron-V3  GR----PSSATHLQS TSGGGGADSVCTAWG PLCAAASNLHELELT PRLPLGHARPEQWPS TLFLPFNFQRQ---- ------  1212
Ron-V2  GR----PSSATHLQS TSGGGGADSVCTAWG PLCAAASNLHELELT PRLPLGHARPEQWPS TLFLPFNFQRQ---- ------  1221
Ron-V1  GR----PSSATHLQS TSGGGGADSVCTAWG PLCAAASNLHELELT PRLPLGHARPEQWPS TLFLPFNFQRQ---- ------  1261
Ron     DHYVQLPATYMNL-- --------------G P-----STSHEM--- ------NVRPEQ-PQ FSPMPGNVRRPRPLS EPPRPT  1400
```

HUMAN RON-RELATED GENE VARIANT ASSOCIATED WITH CANCERS

CROSS REFERENCE TO RELATED APPLICATIONS

This application claims priority to U.S. application Ser. No. 11/465,308 filed Aug. 17, 2006, now U.S. Pat. No. 7,452,985 entitled "Human Ron-Related Gene Variant Associated with Cancers, which is incorporated herein in its entirety.

FIELD OF THE INVENTION

The invention relates to the nucleic acid and polypeptide sequences of a novel human Ron-related gene variant, preparation process thereof, and uses of the same in diagnosing cancers, in particular, breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

BACKGROUND OF THE INVENTION

Cancer is one of the major causes of death in the world. According to the report from the WHO Fact Sheet-Cancer (2003), cancer accounts for 7.1 million (12.6% of the global total) deaths annually and new cancer cases are expected to be increased from 10 million people in 2000 to 15 million people by 2020. In recent years, much progress has been made toward understanding the molecular and cellular biology of cancers. Many important contributions have been made by the identification of several key genetic factors associated with cancers. However, the treatments of cancers still mainly depend on surgery, chemotherapy and radiotherapy because the molecular mechanisms underlying the pathogenesis of cancers remain largely unclear.

It is interesting to note that receptor tyrosine kinases are a family of proteins reported to be involved in many fundamental cellular processes such as cell cycle, signalling transduction, proliferation, differentiation, adhesion, migration, and apoptosis. An important role of the receptor tyrosine kinases in the development of cancers has been reported previously. Therefore, future strategies for the prevention and treatment of cancers may be focused on the elucidation of the receptor tyrosine kinases which are involved in the pathogenesis of cancers. Ron, a member of the receptor tyrosine kinase family located on human chromosome 3p21 (a region frequently deleted in small cell lung carcinoma), was isolated and identified through the screening of cDNA libraries. Previous studies have indicated that Ron is involved in many genetic mechanisms of the tumor cells (Wang et al., (2003) Carcinogenesis 24:1291-300; Angeloni et al., (2004) J Biol. Chem. 279:3726-32; Peace et al., (2005) Cancer Res. 65:1285-93; Camp et al., (2005) Ann Surg Oncol. 12:273-81), and that Ron is a potential target for understanding the pathogenesis of cancers. In addition, the association between gene variants and diseases has been reported previously. Therefore, the discovery of gene variants of Ron may be important for the diagnostic markers of cancers.

SUMMARY OF THE INVENTION

The present invention provides one Ron-related gene variant present in human breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma. The nucleotide sequence of the gene variant and polypeptide sequence encoded thereby can be used for the diagnosis of any diseases associated with this gene variant or cancers, in particular, breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

The invention further provides an expression vector and host cell for expressing the variant.

The invention further provides a method for producing the variant.

The invention further provides an antibody that specifically binds to the variant. For example, by selecting a sequence unique to one of the variants, e.g., a peptide fragment that spans one the deletion junctions, an antibody may be generated that binds to one of the variants and not to RON. Preferably, such peptide antigens are at least 17 amino acid long, but in some cases smaller peptides such as 10 mers, 12 mers, or 15 mers may suffice. Longer peptides, such as 20 mers, 50 mers, hundred-mers (and those therebetween) and even up to full length proteins may be used.

The invention also provides methods for detecting the presence of the variant in a mammal.

BRIEF DESCRIPTION OF THE DRAWINGS

FIG. 1 shows the nucleic acid sequence (SEQ ID NO:1), amino acid sequence (SEQ ID NO:2) and nucleic acid with corresponding amino acid sequence (SEQ ID NO: 1 & 2) of Ron.

FIG. 2 shows the nucleic acid sequence (SEQ ID NO:3), amino acid sequence (SEQ ID NO:4) and nucleic acid with corresponding amino acid sequence (SEQ ID NO: 3 & 4) of Ron-V1.

FIG. 3 shows the nucleic acid sequence (SEQ ID NO:5), amino acid sequence (SEQ ID NO:6) and nucleic acid with corresponding amino acid sequence (SEQ ID NO: 5 & 6) of Ron-V2.

FIG. 4 shows the nucleic acid sequence (SEQ ID NO:7), amino acid sequence (SEQ ID NO:8) and nucleic acid with corresponding amino acid sequence (SEQ ID NO: 7 & 8) of Ron-V3.

FIG. 5 shows the nucleotide sequence alignment between the human Ron gene (SEQ ID NO: 1) and its related gene variants (Ron-V1, Ron-V2, and Ron-V3, SEQ ID NO: ID 3, 5, 7).

FIG. 6 shows the amino acid sequence alignment between the human Ron protein (SEQ ID NO: 2) and its related gene variants (Ron-V1, Ron-V2, and Ron-V3) (SEQ ID NO: 4, 6, 8).

DETAILED DESCRIPTION OF THE INVENTION

Figure 7:
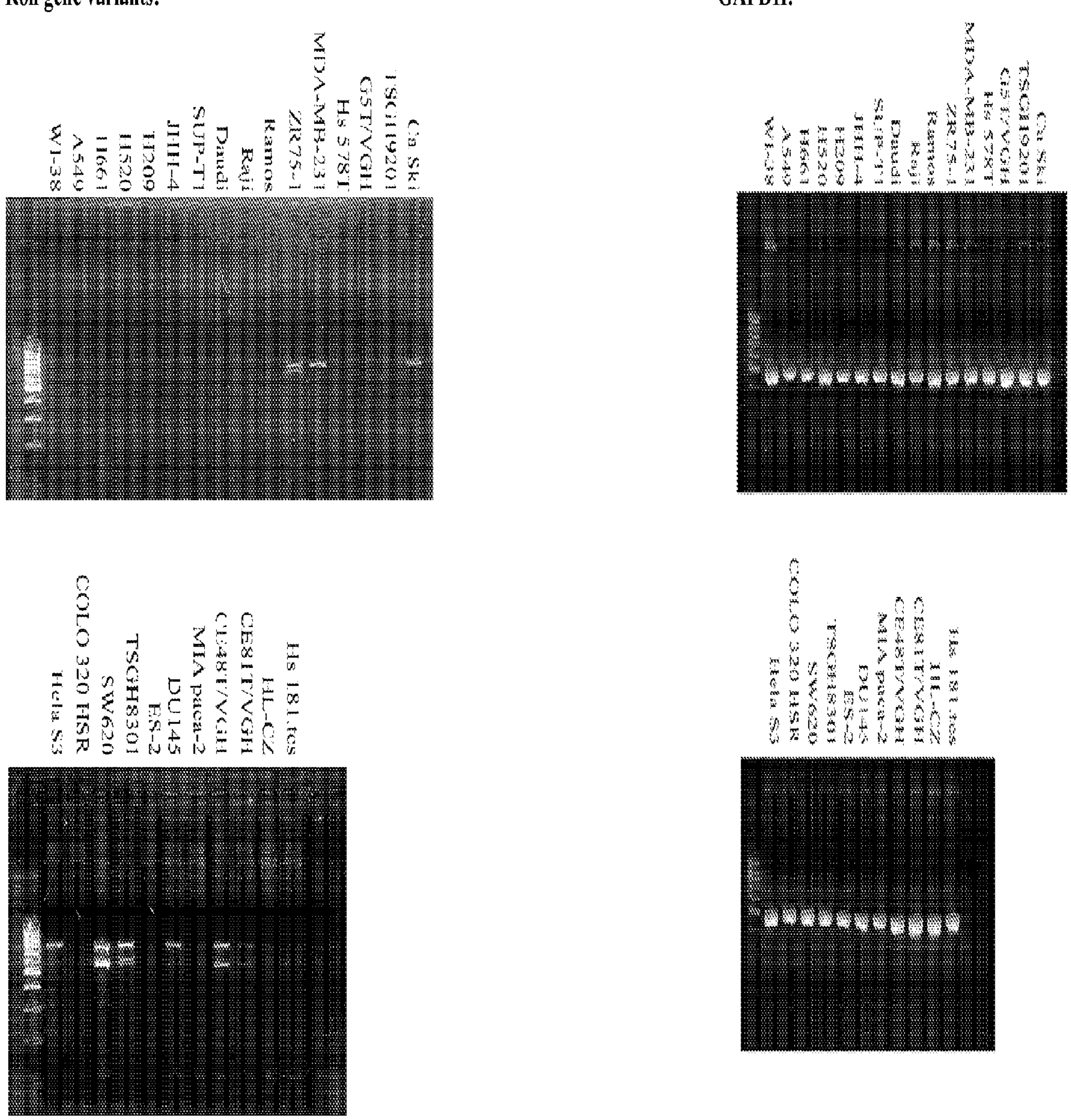
FIG. 7 shows the expression pattern of Ron gene variants in human cell lines.

All technical and scientific terms used herein, unless otherwise defined, have the same meanings as commonly understood by persons skilled in the art.

The term "antibody" used herein denotes intact molecules (a polypeptide or group of polypeptides) as well as fragments thereof, such as Fab, R(ab')2, and Fv fragments, which are capable of binding epitopes. Antibodies are produced by specialized B cells after stimulation by an antigen. Structurally, antibody consists of four subunits including two heavy chains and two light chains. The internal surface shape and charge distribution of the antibody binding domain is complementary to the features of an antigen. Thus, antibody can specifically act against the antigen in an immune response.

The term "base pair (bp)" used herein denotes nucleotides composed of a purine on one strand of DNA which can be hydrogen bonded to a pyrimidine on the other strand. Thymine (or uracil) and adenine residues are linked by two hydrogen bonds. Cytosine and guanine residues are linked by three hydrogen bonds.

The term "Basic Local Alignment Search Tool ("BLAST") (BLAST; Altschul et al., (1997) Nucleic Acids Res. 25: 3389-3402) used herein denotes programs for evaluation of homologies between a query sequence (amino or nucleic acid) and a test sequence. Specific BLAST programs are described as follows:

(1) BLASTN compares a nucleotide query sequence against a nucleotide sequence database;

(2) BLASTP compares an amino acid query sequence against a protein sequence database;

(3) BLASTX compares the six-frame conceptual translation products of a query nucleotide sequence against a protein sequence database;

(4) TBLASTN compares a query protein sequence against a nucleotide sequence database translated in all six reading frames; and (5) TBLASTX compares the six-frame translations of a nucleotide query sequence against the six-frame translations of a nucleotide sequence database.

The term "cDNA" used herein denotes nucleic acids synthesized from a mRNA template using reverse transcriptase.

The term "cDNA library" used herein denotes a library composed of complementary DNAs which are reverse-transcribed from mRNAs.

The term "complement" used herein denotes a polynucleotide sequence capable of forming base pairing with another polynucleotide sequence. For example, the sequence 5'-ATGGACTTACT-3' binds to the complementary sequence 5'-AGTAAGTCCAT-3'.

The term "deletion" used herein denotes a removal of a portion of one or more amino acid residues/nucleotides from a gene.

The term "expressed sequence tags (ESTs)" used herein denotes short (200 to 500 base pairs) nucleotide sequence that derives from either 5' or 3' end of a cDNA.

The term "expression vector" used herein denotes nucleic acid constructs which contain a cloning site for introducing the DNA into vector, one or more selectable markers for selecting vectors containing the DNA, an origin of replication for replicating the vector whenever the host cell divides, a terminator sequence, a polyadenylation signal, and a suitable control sequence which can effectively express the DNA in a suitable host. The suitable control sequence may include promoter, enhancer and other regulatory sequences necessary for directing polymerases to transcribe the DNA.

The term "host cell" used herein denotes a cell which is used to receive, maintain, and allow the reproduction of an expression vector comprising DNA. Host cells are transformed or transfected with suitable vectors constructed using recombinant DNA methods. The recombinant DNA introduced with the vector is replicated whenever the cell divides.

The term "insertion" or "addition" used herein denotes the addition of a portion of one or more amino acid residues/nucleotides to a gene.

The term "in silico" used herein denotes a process of using computational methods (e.g., BLAST) to analyze DNA sequences.

The term "polymerase chain reaction (PCR)" used herein denotes a method which increases the copy number of a nucleic acid sequence using a DNA polymerase and a set of primers (about 20 bp oligonucleotides complementary to each strand of DNA) under suitable conditions (successive rounds of primer annealing, strand elongation, and dissociation).

The term "polynucleotide" or "nucleic acid sequence" used herein denotes a sequence of nucleotide (guanine, cytosine, thymine or adenine) in a specific order that can be a natural or synthesized fragment of DNA or RNA. It may be single-stranded or double-stranded.

The term "protein" or "polypeptide" used herein denotes a sequence of amino acids in a specific order that can be encoded by a gene or by a recombinant DNA. It can also be chemically synthesized.

The term "RNA interference (RNAi)" used herein denotes an introduction of homologous double stranded RNA (dsRNA) into a cell to specifically inhibit the expression of a gene.

The term "reverse transcriptase-polymerase chain reaction (RT-PCR)" used herein denotes a process which transcribes mRNA to complementary DNA strand using reverse transcriptase followed by polymerase chain reaction to amplify the specific fragment of DNA sequences.

The term "transformation" used herein denotes a process describing the uptake, incorporation, and expression of exogenous DNA by prokaryotic host cells.

The term "transfection" used herein denotes a process describing the uptake, incorporation, and expression of exogenous DNA by eukaryotic host cells.

The term "variant" used herein denotes a fragment of sequence (nucleotide or amino acid) inserted or deleted by one or more nucleotides/amino acids.

According to the present invention, the polypeptides of one novel human Ron-related gene variant and the nucleic acid sequences encoding the same are provided.

According to the present invention, human Ron cDNA sequence was used to query the human EST databases using BLAST program to search for Ron-related gene variants. Three human cDNA partial sequences (i.e., EST) showing similar to Ron was identified from ESTs deposited in a cDNA database constructed using a SW620 (colon adenocarcinoma) cell line. The cDNA clones, named Ron-V1 (Ron variant 1), Ron-V2 (Ron variant 2), and Ron-V3 (Ron variant 3), were then isolated from the SW620 cDNA library and sequenced. FIGS. 2-4 show the nucleic acid sequences (SEQ ID NOs: 3, 5, & 7) of Ron-V1, Ron-V2, and Ron-V3 and its corresponding amino acid sequences (SEQ ID NOs: 4, 6, & 8) encoded thereby.

The full-length of the Ron-V1 cDNA is a 4000 bp clone containing a 3783 bp open reading frame (ORF) extending from 29 bp to 3811 bp, which corresponds to an encoded protein of 1261 amino acid residues with a predicted molecular mass of 136.1 kDa. The initiation ATG sequence of Ron-V1 is located at nucleotide 29-31 bp. The full-length of the Ron-V2 cDNA is a 3880 bp clone containing a 3663 bp open reading frame (ORF) extending from 29 bp to 3691 bp, which corresponds to an encoded protein of 1221 amino acid residues with a predicted molecular mass of 132 kDa. The initiation ATG sequence of Ron-V2 is located at nucleotide 29-31 bp. The full-length of the Ron-V3 cDNA is a 3853 bp clone containing a 3636 bp open reading frame (ORF) extending from 29 bp to 3664 bp, which corresponds to an encoded protein of 1212 amino acid residues with a predicted molecular mass of 131.1 kDa. The initiation ATG sequence of Ron-V3 is located at nucleotide 29-31 bp. To determine the variations in sequence of Ron-V1, Ron-V2 and Ron-V3 cDNA clones, an alignment of Ron nucleotide/amino acid sequence with Ron-V1, Ron-V2 and Ron-V3 was performed (FIGS. 5 and 6). The results indicate that (1) Ron-V1: three major genetic deletions were found in the aligned nucleotide sequences showing that Ron-V1 has a 255 bp, a 137 bp and a 149 bp deletions in the sequence of Ron from nucleotides 2838-3092, nucleotides 3839-3975 and nucleotides 4118-4266, respectively; (2) Ron-V2: four major genetic deletions were found in the aligned nucleotide sequences showing that Ron-V2 has a 120 bp, a 255 bp, a 137 bp and a 149 bp deletions in the sequence of Ron from nucleotides 2678-2797, nucleotides 2838-3092, nucleotides 3839-3975 and nucleotides 4118-4266, respectively; (3) Ron-V3: four major genetic deletions were found in the aligned nucleotide sequences showing that Ron-V3 has a 147 bp, a 255 bp, a 137 bp and a 149 bp deletions in the sequence of Ron from nucleotides 2678-2824, nucleotides 2838-3092, nucleotides 3839-3975 and nucleotides 4118-4266, respectively. Scanning Ron, Ron-V1, Ron-V2 and Ron-V3 amino acid sequences against protein profile databases including PROSITE (Motif Scan) indicated that Ron protein contains one Sema domain (31-522aa), one Protein_Kinase_ATP (1088-1114aa), one Protein_Kinase_TYR (1204-1216aa), and one Protein_Kinase_DOM (1082-1345aa). Ron-V1 protein contains one Sema domain (31-522aa), one Protein_Kinase_ATP (1003-1029aa), one Protein_Kinase_TYR (1119-1131aa), and one Protein_Kinase_DOM (997-1261aa). Ron-V2 protein contains one Sema domain (31-522aa), one Protein_Kinase_ATP (963-989aa), one Protein_Kinase_TYR (1079-1091aa), and one Protein_Kinase_DOM (957-1221aa). Ron-V3 protein contains one Sema domain (31-522aa), one Protein_Kinase_ATP (954-980aa), one Protein_Kinase_TYR (1070-1082aa), and one Protein_Kinase_DOM (948-1212aa).

In the present invention, a search of ESTs deposited in dbEST at NCBI was performed to determine the presence of Ron gene variants in silico. The result of in silico analysis showed that one EST (GenBank accession number BG823879) was found to confirm the absence of 255 bp region on Ron-V1, Ron-V2, and Ron-V3 nucleotide sequences; one EST (GenBank accession number AW009348) was found to confirm the absence of 137 bp region on Ron-V1, Ron-V2, and Ron-V3 nucleotide sequences. Therefore, any Ron nucleotide fragments containing the immediately upstream and downstream sequences of the deleted 255 bp region (2837-2838 bp of Ron-V1; 2717-2718 bp of Ron-V2; 2691-2692 bp of Ron-V3) and/or 137 bp region (3583-3584 bp of Ron-V1; 3463-3464 bp of Ron-V2; 3436-3437 bp of Ron-V3) and/or 149 bp region (3725-3726 bp of Ron-V1; 3605-3606 bp of Ron-V2; 3578-3579 bp of Ron-V3) are the "gene targets" which may be used as probes to determine the presence of Ron-V1, Ron-V2, and Ron-V3 under high stringency conditions. An alternative approach is that any set of primers for amplifying the fragment containing the immediately upstream and downstream sequences of the deleted 255 bp region (2837-2838 bp of Ron-V1; 2717-2718 bp of Ron-V2; 2691-2692 bp of Ron-V3) and/or 137 bp region (3583-3584 bp of Ron-V1; 3463-3464 bp of Ron-V2; 3436-3437 bp of Ron-V3) and/or 149 bp region (3725-3726 bp of Ron-V1; 3605-3606 bp of Ron-V2; 3578-3579 bp of Ron-V3) may be used for determining the presence of the variants (Ron-V1, Ron-V2, and Ron-V3). On the other hand, any Ron nucleotide fragments containing the immediately upstream and downstream sequences of the deleted 120 bp region (2678-2679 bp of Ron-V2) and 147 bp region (2678-2679 bp of Ron-V3) are the "gene targets" which may be used as probes for determining the presence of Ron-V2 and Ron-V3, respectively, under high stringency conditions. An alternative approach is that any set of primers for amplifying the fragment containing the immediately upstream and downstream sequences of the deleted 120 bp region (2678-2679 bp of Ron-V2) and 147 bp region (2678-2679 bp of Ron-V3) may be used for determining the presence of Ron-V2 and Ron-V3, respectively.

According to the present invention, the polypeptides of the human Ron-V1, Ron-V2, and Ron-V3 and its fragments thereof may be produced through genetic engineering techniques. In this case, they are produced by appropriate host cells which have been transformed by DNAs that encode for the polypeptides or fragments thereof. The nucleotide sequence encoding the polypeptide of the human Ron-V1, Ron-V2, and Ron-V3 or their fragments thereof are inserted into an appropriate expression vector, i.e., a vector which contains the necessary elements for the transcription and translation of the inserted coding sequence in a suitable host. The nucleic acid sequence is inserted into the vector in a manner that will be expressed under appropriate conditions (e.g., in proper orientation and correct reading frame and with appropriate expression sequences, including an RNA polymerase binding sequence and a ribosomal binding sequence).

Any method that is known to those skilled in the art may be used to construct expression vectors containing sequences encoding the polypeptides of the human Ron-V1, Ron-V2, and Ron-V3 and appropriate transcriptional/translational control elements. These methods may include in vitro recombinant DNA and synthetic techniques, and in vivo genetic recombinants.

A variety of expression vector/host systems may be utilized to express the polypeptide-coding sequence. These include, but are not limited to, microorganisms such as bacteria transformed with recombinant bacteriophage, plasmid, or cosmid DNA expression vector; yeast transformed with yeast expression vector; insect cell systems infected with virus (e.g., baculovirus); plant cell system transformed with viral expression vector (e.g., cauliflower mosaic virus, CaMV, or tobacco mosaic virus, TMV); or animal cell system infected with virus (e.g., vaccina virus, adenovirus, etc.). Preferably, the host cell is a bacterium, and most preferably, the bacterium is *E. coli.*

Alternatively, the Polypeptides of the human Ron-V1, Ron-V2, and Ron-V3 or fragments thereof may be synthesized using chemical methods. For example, peptide synthesis can be performed using various solid-phase techniques. Automated synthesis may be achieved using the ABI 431A peptide synthesizer (Perkin-Elmer).

According to the present invention, the fragments of the polypeptides and nucleic acid sequences of the human Ron-V1, Ron-V2, and Ron-V3 are used as immunogens, primers or probes. Preferable, the purified fragments of the human Ron-V1, Ron-V2, and Ron-V3 are used. The fragments may be produced by enzyme digestion, chemical cleavage of isolated or purified polypeptide or nucleic acid sequences, or chemical synthesis. Thereafter, the fragments may be isolated or purified. Such isolated or purified fragments of the polypeptides and nucleic acid sequences can be used as immunogens, primers or probes.

The present invention further provides the antibodies which specifically bind one or more out-surface epitopes of the polypeptides of the human Ron-V1, Ron-V2, and Ron-V3.

According to the present invention, immunization of mammals with immunogens described herein, preferably humans, rabbits, rats, mice, sheep, goats, cows, or horses, is performed following procedures well known to those skilled in the art, for the purpose of obtaining antisera containing polyclonal antibodies or hybridoma lines secreting monoclonal antibodies.

Monoclonal antibodies can be prepared by standard techniques. Such techniques are disclosed, for example, in U.S. Pat. No. 4,271,145 and U.S. Pat. No. 4,196,265. An animal is immunized with the immunogen. Hybridomas are prepared by fusing spleen cells from the immunized animal with myeloma cells. The fusion products are screened for those producing antibodies that specifically bind to the immunogen. The positive hybridoma clones are isolated, and the monoclonal antibodies are recovered from those clones.

Immunization regimens for production of both polyclonal and monoclonal antibodies are well-known in the art. The immunogen may be injected by any of a number of routes, including subcutaneous, intravenous, intraperitoneal, intradermal, intramuscular, mucosal, or a combination thereof. The immunogen may be injected in soluble form, aggregate form, attached to a physical carrier, or mixed with an adjuvant, using methods and materials well-known in the art. The antisera and antibodies may be purified using well-known column chromatography methods.

According to the present invention, antibody fragments which contain specific binding sites for the polypeptides or fragments thereof may also be generated. For example, such fragments include, but are not limited to, F(ab')2 fragments produced by pepsin digestion of the antibody molecule and Fab fragments generated by reducing the disulfide bridges of the F(ab')2 fragments.

The subject invention also provides methods for diagnosing the diseases associated with Ron-V1, Ron-V2, or Ron-V3, particularly breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma, by utilizing the nucleic acid sequences, the polypeptide of the human Ron-V1, Ron-V2, or Ron-V3, or fragments thereof, and the antibodies against the polypeptides.

Since Ron-V1, Ron-V2, or Ron-V3 clones were isolated from a SW620 cDNA library, it is advisable that Ron-V1, Ron-V2, or Ron-V3 serve as a marker for the diagnosis of human colon adenocarcinoma. Thus, the expression levels/patterns of Ron-V1, Ron-V2, or Ron-V3 may be a useful indicator for screening patients suspected of having cancers or more specifically, breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma. This suggests that relative expression levels/patterns (mRNA or protein) may confer an increased susceptibility to cancers, and more preferably, to breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma. Fragments of Ron-V1, Ron-V2, or Ron-V3 transcripts (mRNAs) may be detected by RT-PCR approach. Polypeptides of Ron-V1, Ron-V2, or Ron-V3 may be determined by the binding of antibodies to these polypeptides. These approaches may be performed in accordance with conventional methods well known to persons skilled in the art. On the other hand, a method (RNAi; RNA interference) that is known to those skilled in the art may be used to interfere and degrade the targeted RNA using chemically synthesized double stranded short nucleic acid (about 23 nucleotides dsRNA) molecules (Montgomery et al. (1998) Proc Natl Acad Sci USA. 95:15502-7). According to the present invention, the double stranded short nucleic acid molecules containing the sequences of the "gene targets": nucleotides 2837-2838, nucleotides 3583-3584, or nucleotides 3725-3726 of Ron-V1; nucleotides 2717-2718, nucleotides 3463-3464, or nucleotides 3605-3606 of Ron-V2; nucleotides 2691-2692, nucleotides 3436-3437, or nucleotides 3578-3579 of Ron-V3, which may be used to specifically interfere and degrade Ron-V1, Ron-V2, and Ron-V3 mRNAs. On the other hand, the double stranded short nucleic acid molecules containing the sequence of the "gene targets": nucleotides 2678-2679 of Ron-V2 or Ron-V3, may be used to specifically interfere and degrade Ron-V2 and Ron-V3 mRNA, respectively. After RNAi approach was conducted, the decreased transcripts or polypeptides may be used to interpret the presence of Ron-V1, Ron-V2, and Ron-V3 mRNAs.

According to the present invention, the expression of these gene variant mRNAs in sample may be determined by, but not limited to, RT-PCR. Using TRIZOL™ reagents (LIFE TECHNOLOGY®), total RNA may be isolated from patient samples. Tissue samples (e.g., biopsy samples) are powdered under liquid nitrogen before homogenization. RNA purity and integrity are assessed by absorbance at 260/280 nm and by agarose gel electrophoresis. A set of primers can be designed to amplify the expected size of specific PCR fragments (gene targets) of Ron-V1, Ron-V2, and Ron-V3. For example, one of the primers is a fragment of the sequence (A fragment; forward primer) containing the gene targets: nucleotides 2837-2838, nucleotides 3583-3584, or nucleotides 3725-3726 of Ron-V1; nucleotides 2717-2718, nucleotides 3463-3464, or nucleotides 3605-3606 of Ron-V2; nucleotides 2691-2692, nucleotides 3436-3437, or nucleotides 3578-3579 of Ron-V3, and the other is a fragment (B fragment; reverse primer) designed from a reverse complementary strand of Ron-V1, Ron-V2, and Ron-V3 sequences at any location downstream of "A fragment". If "B fragment" is designed from a reverse complementary strand of the sequence containing the gene targets: nucleotides 2837-2838, nucleotides 3583-3584, or nucleotides 3725-3726 of Ron-V1; nucleotides 2717-2718, nucleotides 3463-3464, or nucleotides 3605-3606 of Ron-V2; nucleotides 2691-2692, nucleotides 3436-3437, or nucleotides 3578-3579 of Ron-V3, the "A fragment" is a fragment of the sequence at any location upstream of "B fragment". Alternatively, one primer (A fragment; forward primer) is at any location upstream of the sequence containing "gene targets" and the other is designed from a reverse complementary strand at any location downstream of the sequence containing "gene targets". PCR fragments are analyzed on a 1% agarose gel using five microliters (10%) of the amplified products. The intensity of the signals may be determined by using the Molecular Analyst program (version 1.4.1; Bio-Rad). Thus, the relative expression level for each amplified PCR product may be calculated based on the intensity of signals.

The RT-PCR experiment may be performed according to the manufacturer instructions (BOEHRNGER MANNHEIM®). A 50 μl reaction mixture containing 2 μl total RNA (0.1 μg/μl), 1 μl each primer (20 μM), 1 μl each dNTP (10 mM), 2.5 μl DTT solution (100 mM), 10 μl 5×RT-PCR buffer, 1 μl enzyme mixture, and 28.5 μl sterile distilled water may be subjected to the conditions such as reverse transcription at 60° C. for 30 minutes followed by 35 cycles of denaturation at 94° C. for 2 minutes, annealing at 60° C. for 2 minutes, and extension at 68° C. for 2 minutes. The RT-PCR analysis may be repeated twice to ensure reproducibility, for a total of three independent experiments.

The expression of gene variants can also be analyzed using Northern Blot hybridization approach. Specific fragments containing the sequences of the "gene targets" of the Ron-V1, Ron-V2, and Ron-V3 may be amplified by polymerase chain reaction (PCR) using primer set designed for RT-PCR. The amplified PCR fragment may be labeled and served as a probe to hybridize the membranes containing total RNAs extracted from the samples under the conditions of 55° C. in a suitable hybridization solution for 3 hours. Blots may be washed twice in 2×SSC, 0.1% SDS at room temperature for 15 minutes each, followed by two washes in 0.1×SSC and 0.1% SDS at 65° C. for 20 minutes each. After these washes, blot may be rinsed briefly in suitable washing buffer and incubated in blocking solution for 30 minutes, and then incubated in suitable antibody solution for 30 minutes. Blots may be washed in washing buffer for 30 minutes and equilibrated in suitable detection buffer before detecting the signals. Alternatively, the presence of the "gene targets" of the gene variants (cDNAs or PCR) can be detected using microarray approach. The cDNAs or PCR products corresponding to the nucleotide sequences of the present invention may be immobilized on a suitable substrate such as a glass slide. Hybridization can be preformed using the labeled mRNAs extracted from samples. After hybridization, nonhybridized mRNAs are removed. The relative abundance of each labeled transcript, hybridizing to a cDNA/PCR product immobilized on the microarray, can be determined by analyzing the scanned images.

According to the present invention, the presence of the polypeptide of Ron-V1, Ron-V2, and Ron-V3 in samples may be determined by, but not limited to, the immunoassay which uses the antibody that specifically binds to the polypeptide. The polypeptides of the gene variants may be expressed in prokaryotic cells by using suitable prokaryotic expression vectors. The cDNA fragments of Ron-V1, Ron-V2, and Ron-V3 genes encoding the amino acid sequences may be PCR amplified using primer set designed with restriction enzyme digestion sites incorporated in the 5' and 3' ends. The PCR products can then be enzyme digested, purified, and inserted into the corresponding sites of prokaryotic expression vector in-frame to generate recombinant plasmids. Sequence fidelity of this recombinant DNA can be verified by sequencing. The prokaryotic recombinant plasmids may be transformed into host cells (e.g., *E. coli* BL21 (DE3)). Recombinant protein synthesis may be stimulated by the addition of 0.4 mM isopropylthiogalactoside (IPTG) for 3 h. The bacterially-expressed proteins may be purified.

The polypeptide of the gene variant may be expressed in animal cells by using eukaryotic expression vectors. Cells may be maintained in Dulbecco's modified Eagle's medium (DMEM) supplemented with 10% fetal bovine serum (FBS; GIBCOS® BRL) at 37° C. in a humidified 5% $CO_2$ atmosphere. Before transfection, the nucleotide sequence of each of the gene variant may be amplified with PCR primers containing restriction enzyme digestion sites and ligated into the corresponding sites of eukaryotic expression vector in-frame. Sequence fidelity of this recombinant DNA can be verified by sequencing. The cells may be plated in 12-well plates one day before transfection at a density of 5×104 cells per well. Transfections may be carried out using Lipofectaminutese Plus transfection reagent according to the manufacturer's instructions (GIBCO® BRL). Three hours following transfection, medium containing the complexes may be replaced with fresh medium. Forty-eight hours after incubation, the cells may be scraped into lysis buffer (0.1 M Tris HCl, pH 8.0, 0.1% Triton X-100) for purification of expressed proteins. After these proteins are purified, monoclonal antibodies against these purified proteins (Ron-V1, Ron-V2, and Ron-V3) may be generated using hybridoma technique according to the conventional methods (de StGroth and Scheidegger, (1980) J Immunol Methods 35:1-21; Cote et al. (1983) Proc Natl Acad Sci USA 80: 2026-30; and Kozbor et al. (1985) J Immunol Methods 81:31-42).

According to the present invention, the presence of the polypeptides of Ron-V1, Ron-V2, and Ron-V3 in samples of the breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma may be determined by a Western blot analysis. Proteins extracted from samples may be separated by SDS-PAGE and transferred to suitable membranes such as polyvinylidene difluoride (PVDF) in transfer buffer (25 mM Tris-HCl, pH 8.3, 192 mM glycine, 20% methanol) with a Trans-Blot apparatus for 1 h at 100 V (e.g., Bio-Rad). The proteins can be immunoblotted with specific antibodies. For example, membrane blotted with extracted proteins may be blocked with suitable buffers such as 3% solution of BSA or 3% solution of nonfat milk powder in TBST buffer (10 mM Tris-HCl, pH 8.0, 150 mM NaCl, 0.1% Tween 20) and incubated with monoclonal antibody directed against the polypeptides of gene variants. Unbound antibody is removed by washing with TBST for 5×1 minutes. Bound antibody may be detected using commercial ECL Western blotting detecting reagents.

The following examples are provided for illustration, but not for limiting the invention.

EXAMPLES

Analysis of Human Colon Adenocarcinoma EST Database

Expressed sequence tags (ESTs) generated from the large-scale PCR-based sequencing of the 5'-end of human colon adenocarcinoma cDNA clones were compiled and served as EST databases. Sequence comparisons against the nonredundant nucleotide and protein databases were performed using BLASTN and BLASTX programs, at the National Center for Biotechnology Information (NCBI™) with a significance cutoff of p<10-10. ESTs representing putative Ron-V1, Ron-V2, and Ron-V3 genes were identified during the course of EST generation.

Isolation of cDNA Clones

Three cDNA clones exhibiting EST sequences similar to the Ron gene were isolated from the human colon adenocarcinoma cDNA library and named Ron-V1, Ron-V2, and Ron-V3. The inserts of these clones were subsequently excised in vivo from the λZAP Express vector using the EXASSIST™/XLOLR helper phage system (STRATAGENE™). Phagemid particles were excised by coinfecting XL1-BLUE MRF' cells with EXASSIST™ helper phage. The excised pBluescript phagemids were used to infect *E. coli* XLOLR cells, which lack the amber suppressor necessary for EXASSIST™ phage replication. Infected XLOLR cells were selected using kanamycin resistance. Resultant colonies contained the double stranded phagemid vector with the cloned cDNA insert. A single colony was grown overnight in LB-kanamycin, and DNA was purified using a QIAGEN® plasmid purification kit.

Full Length Nucleotide Sequencing and Database Comparisons

Phagemid DNA was sequenced using the Taq dye-deoxy terminator cycle sequencing kit for the APPLIED BIOSYSTEMS 377™ sequencing system (PERKINELMER® Life Sciences). Using the primer-walking approach, full-length sequence was determined. Nucleotide and protein searches were performed using BLAST against the non-redundant database of NCBI™.

In Silico Sequence Similarity Analysis

The coding sequence for each cDNA clones was searched against the dbEST sequence database using the BLAST algorithm at the NCBI™ website. ESTs derived from dbEST sequence database were used as a source of information for transcript sequence similarity analysis. The accession numbers of the ESTs matching to the deleted sequence of Ron-V1, Ron-V2, and Ron-V3 were identified.

RT-PCR Expression Pattern Analysis

The expression patterns of Ron-V1, Ron-V2, and Ron-V3 were conducted in human cell lines using RT-PCR. The human cell lines were WI38 (Lung, fetus); A549 (Lung adenocarcinoma); H661 (Large cell carcinoma, lung); H520 (Squamous cell carcinoma, lung); H209 (Small cell carcinoma, lung); JHH-4 (Hepatoma); SUP-T1 (T-cell lymophoblastic lymphoma); Daudi (Burkitt's lymophoma); Ramos (Burkitt's lymophoma); RAJI (Burkitt's lymophoma); ZR75-1 (Breast carcinoma); MDA-MB-231 (Breast adenocarcinoma); Hs 578T (Breast carcinoma); G5TNGH (Glioblastoma multiforme); TSGH9201 (Gastric carcinoma); Ca Ski (Cervix epidermoid carcinoma); Hela S3 (Cervical epitheloid carcinoma); COLO 320 HSR (Colon adenocarcinoma); SW620 (Colon adenocarcinoma); TSGH8301 (Urinary bladder carcinoma); ES-2 (Ovarian carcinoma); DU145 (Brain prostate carcinoma); MIA paca-2 (Pancreatic carcinoma); CE48TNGH (Esophagus epidermoid carcinoma); CE81TNGH (Esophagus carcinoma well differentiated aquamous); HL-CZ (Promonocytic leukemia); Hs 181.tes (Normal testis). The purity and integrity of total RNA extracted from each of the cell lines were assessed by absorbance at 260/280 nm and by agarose gel electrophoresis. The forward and reverse primers for Ron gene variants were: (SEQ ID NO: 9) 5'-GACTGAGTGTCTGCTAGCACGG-3' and (SEQ ID NO: 10) 5'-ATGGCAGGGAGTGCATCTACGC-3'. The expected size of Ron-V1, Ron-V2, and Ron-V3 PCR fragments were 660 bp, 540 bp and 513 bp.

Glyceraldehyde-3-phosphate dehydrogenase (GAPDH; accession No. M33197) was used for internal control. The forward and reverse primers for GAPDH were: (SEQ ID NO: 11) 5'-TGGGTGTGAACCATGAGAAG-3' and (SEQ ID NO: 12) 5'-GTGTCGCTGTTGAAGTCAGA-3'. The expected size of GAPDH PCR fragment was 472 bp. Briefly, a 50 μl reaction mixture containing 2 μl total RNA (0.1 μg/μl), 1 μl each primer (20 pM), 1 μl each dNTP (10 mM), 2.5 μl DTT solution (100 mM), 10 μl 5×RT-PCR buffer, 1 μl enzyme mixture and 28.5 μl sterile redistilled water were subjected to reverse transcription at 60° C. for 30 min followed by 35 cycles of denaturation at 94° C. for 2 mM, annealing at 60° C. for 2 min, and extension at 68° C. for 2 min. Five microliters (10%) of the amplified products mixed with 1 μl of loading buffer were separated on a 1% horizontal agarose gel stained with ethidium bromide in 0.5×TAE buffer. The gel was electrophoresed at 100 V for 45 min.

FIG. 7 showed that Ron-V1 (660 bp), Ron-V2 (540 bp), and Ron-V3 (513 bp) mRNAs were RT-PCR amplified using the primers described above. Shown on the left are 100 bp DNA ladder markers. The PCR fragments of Ron-V1 (660 bp), Ron-V2 (540 bp), and Ron-V3 (513 bp) were confirmed by sequencing. Ron-V1 mRNA was expressed in the cell lines of cervix epitheloid carcinoma, colon adenocarcinoma, urinary bladder carcinoma, prostate carcinoma, esophagus carcinoma, and esophagus epidermoid carcinoma; Ron-V2 mRNA was expressed in the cell lines of breast carcinoma, breast adenocarcinoma, cervix epidermoid carcinoma, colon adenocarcinoma, and urinary bladder carcinoma; Ron-V3 mRNA was expressed in the cell lines of breast carcinoma, colon adenocarcinoma, urinary bladder carcinoma, esophagus carcinoma, and esophagus epidermoid carcinoma. The differential expression pattern among Ron-V1, Ron-V2, and Ron-V3 implied that they may be functionally different and may be a suitable marker for diagnosing human breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

REFERENCES

All references are listed herein for the convenience of the reader. Each is incorporated by reference in its entirety.

1. Angeloni et al., The soluble sema domain of the RON receptor inhibits macrophage-stimulating protein-induced receptor activation. J. Biol. Chem. 279:3726-32, (2004).
2. Camp et al., RON, a tyrosine kinase receptor involved in tumor progression and metastasis. Ann Surg Oncol. 12:273-81, (2005).
3. Peace et al., Ron receptor signaling augments mammary tumor formation and metastasis in a murine model of breast cancer. Cancer Res. 65:1285-93, (2005).
4. Wang et al., Oncogenic and invasive potentials of human macrophage-stimulating protein receptor, the RON receptor tyrosine kinase. Carcinogenesis 24:1291-300, (2003).
5. Willett et al., Differential screening of a human chromosome 3 library identifies hepatocyte growth factor-like/macrophage-stimulating protein and its receptor in injured lung. Possible implications for neuroendocrine cell survival. J Clin Invest. 99:2979-91, (1997).

The invention claimed is:

1. An isolated nucleic acid encoding the amino acid sequence of SEQ ID NO: 6.

2. The isolated nucleic acid of claim 1, comprising the nucleotide sequence of SEQ ID NO: 5.

3. An expression vector comprising the nucleic acid of claim 1 or 2.

4. A host cell comprising said expression vector of claim 3.

5. A method for producing a RON variant polypeptide, comprising the steps of:

a) culturing said host cell of claim 4 under a condition suitable for the expression of a RON variant polypeptide; and b) recovering said RON variant polypeptide from the host cell culture.

* * * * *

SEQUENCE LISTING

```
<160> NUMBER OF SEQ ID NOS: 12

<210> SEQ ID NO 1
<211> LENGTH: 4541
<212> TYPE: DNA
<213> ORGANISM: Homo sapiens

<400> SEQUENCE: 1

ggatcctcta gggtcccagc tcgcctcgat ggagctcctc ccgccgctgc ctcagtcctt     60
```

```
cctgttgctg ctgctgttgc ctgccaagcc cgcggcgggc gaggactggc agtgcccgcg    120
cacccctac gcggcctctc gcgactttga cgtgaagtac gtggtgccca gcttctccgc    180
cggaggcctg gtacaggcca tggtgaccta cgagggcgac agaaatgaga gtgctgtgtt    240
tgtagccata cgcaatcgcc tgcatgtgct tgggcctgac ctgaagtctg tccagagcct    300
ggccacgggc cctgctggag accctggctg ccagacgtgt gcagcctgtg gcccaggacc    360
ccacggccct cccggtgaca cagacacaaa ggtgctggtg ctggatcccg cgctgcctgc    420
gctggtcagt tgtggctcca gcctgcaggg ccgctgcttc ctgcatgacc tagagcccca    480
agggacagcc gtgcatctgg cagcgccagc ctgcctcttc tcagcccacc ataaccggcc    540
cgatgactgc cccgactgtg tggccagccc attgggcacc cgtgtaactg tggttgagca    600
aggccaggcc tcctatttct acgtggcatc ctcactggac gcagccgtgg ctggcagctt    660
cagcccacgc tcagtgtcta tcaggcgtct caaggctgac gcctcgggat tcgcaccggg    720
ctttgtggcg ttgtcagtgc tgcccaagca tcttgtctcc tacagtattg aatacgtgca    780
cagcttccac acgggagcct tcgtatactt cctgactgta cagccggcca gcgtgacaga    840
tgatcctagt gccctgcaca cacgcctggc acggcttagc gccactgagc cagagttggg    900
tgactatcgg gagctggtcc tcgactgcag atttgctcca aaacgcaggc gccgggggc    960
cccagaaggc ggacagccct accctgtgct gcaggtggcc cactccgctc cagtgggtgc   1020
ccaacttgcc actgagctga gcatcgccga gggccaggaa gtactatttg ggtctttgt    1080
gactggcaag gatggtggtc ctggcgtggg ccccaactct gtcgtctgtg ccttccccat   1140
tgacctgctg gacacactaa ttgatgaggg tgtggagcgc tgttgtgaat ccccagtcca   1200
tccaggcctc cggcgaggcc tcgacttctt ccagtcgccc agtttttgcc ccaacccgcc   1260
tggcctggaa gccctcagcc ccaacaccag ctgccgccac ttccctctgc tggtcagtag   1320
cagcttctca cgtgtggacc tattcaatgg gctgttggga ccagtacagg tcactgcatt   1380
gtatgtgaca cgccttgaca acgtcacagt ggcacacatg ggcacaatgg atgggcgtat   1440
cctgcaggtg gagctggtca ggtcactaaa ctacttgctg tatgtgtcca acttctcact   1500
gggtgacagt gggcagcccg tgcagcggga tgtcagtcgt cttggggacc acctactctt   1560
tgcctctggg gaccaggttt tccaggtacc tatccgaggc cctggctgcc gccacttcct   1620
gacctgtggg cgttgcctaa gggcatggca tttcatgggc tgtggctggt gtgggaacat   1680
gtgcggccag cagaaggagt gtcctggctc ctggcaacag gaccactgcc cacctaagct   1740
tactgagttc cacccccaca gtggacctct aaggggcagt acaaggctga ccctgtgtgg   1800
ctccaacttc taccttcacc cttctggtct ggtgcctgag ggaacccatc aggtcactgt   1860
gggccaaagt ccctgccggc cactgcccaa ggacagctca aaactcagac cagtgccccg   1920
gaaagacttt gtagaggagt ttgagtgtga actggagccc ttgggcaccc aggcagtggg   1980
gcctaccaac gtcagcctca ccgtgactaa catgccaccg ggcaagcact tccgggtaga   2040
cggcacctcc gtgctgagag gcttctcttt catggagcca gtgctgatag cagtgcaacc   2100
cctctttggc ccacgggcag gaggcacctg tctcactctt gaaggccaga gtctgtctgt   2160
aggcaccagc cgggctgtgc tggtcaatgg gactgagtgt ctgctagcac gggtcagtga   2220
ggggcagctt ttatgtgcca cacccctgg ggccacggtg gccagtgtcc cccttagcct    2280
gcaggtgggg ggtgcccagg tacctggttc ctggaccttc cagtacagag aagaccctgt   2340
cgtgctaagc atcagcccca actgtggcta catcaactcc cacatcacca tctgtggcca   2400
gcatctaact tcagcatggc acttagtgct gtcattccat gacgggctta gggcagtgga   2460
```

```
aagcaggtgt gagaggcagc ttccagagca gcagctgtgc cgccttcctg aatatgtggt   2520

ccgagacccc cagggatggg tggcagggaa tctgagtgcc cgaggggatg gagctgctgg   2580

ctttacactg cctggctttc gcttcctacc cccaccccat ccacccagtg ccaacctagt   2640

tccactgaag cctgaggagc atgccattaa gtttgagtat attgggctgg gcgctgtggc   2700

tgactgtgtg ggtatcaacg tgaccgtggg tggtgagagc tgccagcacg agttccgggg   2760

ggacatggtt gtctgccccc tgcccccatc cctgcagctt ggccaggatg gtgccccatt   2820

gcaggtctgc gtagatggtg aatgtcatat cctgggtaga gtggtgcggc cagggccaga   2880

tggggtccca cagagcacgc tccttggtat cctgctgcct ttgctgctgc ttgtggctgc   2940

actggcgact gcactggtct tcagctactg gtggcggagg aagcagctag ttcttcctcc   3000

caacctgaat gacctggcat ccctggacca gactgctgga gccacacccc tgcctattct   3060

gtactcgggc tctgactaca gaagtggcct tgcactccct gccattgatg gtctggattc   3120

caccacttgt gtccatggag catccttctc cgatagtgaa gatgaatcct gtgtgccact   3180

gctgcggaaa gagtccatcc agctaaggga cctggactct gcgctcttgg ctgaggtcaa   3240

ggatgtgctg attccccatg agcgggtggt cacccacagt gaccgagtca ttggcaaagg   3300

ccactttgga gttgtctacc acggagaata catagaccag gcccagaatc gaatccaatg   3360

tgccatcaag tcactaagtc gcatcacaga gatgcagcag gtggaggcct tcctgcgaga   3420

ggggctgctc atgcgtggcc tgaaccaccc gaatgtgctg gctctcattg gtatcatgtt   3480

gccacctgag ggcctgcccc atgtgctgct gccctatatg tgccacggtg acctgctcca   3540

gttcatccgc tcacctcagc ggaaccccac cgtgaaggac ctcatcagct ttggcctgca   3600

ggtagcccgc ggcatggagt acctggcaga gcagaagttt gtgcacaggg acctggctgc   3660

gcggaactgc atgctggacg agtcattcac agtcaaggtg gctgactttg gtttggcccg   3720

cgacatcctg gacagggagt actatagtgt tcaacagcat cgccacgctc gcctacctgt   3780

gaagtggatg gcgctggaga gcctgcagac ctatagattt accaccaagt ctgatgtgtg   3840

gtcatttggt gtgctgctgt gggaactgct gacacggggt gccccaccat accgccacat   3900

tgaccctttt gaccttaccc acttcctggc ccagggtcgg cgcctgcccc agcctgagta   3960

ttgccctgat tctctgtacc aagtgatgca gcaatgctgg gaggcagacc cagcagtgcg   4020

acccaccttc agagtactag tgggggaggt ggagcagata gtgtctgcac tgcttgggga   4080

ccattatgtg cagctgccag caacctacat gaacttgggc cccagcacct cgcatgagat   4140

gaatgtgcgt ccagaacagc cgcagttctc acccatgcca gggaatgtac gccggccccg   4200

gccactctca gagcctcctc ggcccacttg acttagttct tggctggac  ctgcttagct   4260

gccttgagct aaccccaagg ctgcctctgg gccatgccag gccagagcag tggccctcca   4320

ccttgttcct gccctttaac tttcagaggc aataggtaaa tgggcccatt aggtccctca   4380

ctccacagag tgagccagtg agggcagtcc tgcaacatgt atttatggag tgcctgctgt   4440

ggaccctgtc ttctgggcac agtggactca gcagtgacca caccaacact gacccttgaa   4500

ccaataaagg aacaaatgac tattaaagca caaaaaaaaa a                        4541
```

<210> SEQ ID NO 2
<211> LENGTH: 1400
<212> TYPE: PRT
<213> ORGANISM: Homo sapiens

<400> SEQUENCE: 2

Met Glu Leu Leu Pro Pro Leu Pro Gln Ser Phe Leu Leu Leu Leu Leu

-continued

```
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
            420                 425                 430
```

```
Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830

Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro Pro His
    850                 855                 860
```

```
Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
                885                 890                 895

Asn Val Thr Val Gly Gly Glu Ser Cys Gln His Glu Phe Arg Gly Asp
            900                 905                 910

Met Val Val Cys Pro Leu Pro Pro Ser Leu Gln Leu Gly Gln Asp Gly
        915                 920                 925

Ala Pro Leu Gln Val Cys Val Asp Gly Glu Cys His Ile Leu Gly Arg
    930                 935                 940

Val Val Arg Pro Gly Pro Asp Gly Val Pro Gln Ser Thr Leu Leu Gly
945                 950                 955                 960

Ile Leu Leu Pro Leu Leu Leu Leu Val Ala Ala Leu Ala Thr Ala Leu
                965                 970                 975

Val Phe Ser Tyr Trp Trp Arg Arg Lys Gln Leu Val Leu Pro Pro Asn
            980                 985                 990

Leu Asn Asp Leu Ala Ser Leu Asp  Gln Thr Ala Gly Ala  Thr Pro Leu
        995                 1000                1005

Pro Ile  Leu Tyr Ser Gly Ser  Asp Tyr Arg Ser Gly  Leu Ala Leu
    1010                1015                1020

Pro Ala  Ile Asp Gly Leu Asp  Ser Thr Thr Cys Val  His Gly Ala
    1025                1030                1035

Ser Phe  Ser Asp Ser Glu Asp  Glu Ser Cys Val Pro  Leu Leu Arg
    1040                1045                1050

Lys Glu  Ser Ile Gln Leu Arg  Asp Leu Asp Ser Ala  Leu Leu Ala
    1055                1060                1065

Glu Val  Lys Asp Val Leu Ile  Pro His Glu Arg Val  Val Thr His
    1070                1075                1080

Ser Asp  Arg Val Ile Gly Lys  Gly His Phe Gly Val  Val Tyr His
    1085                1090                1095

Gly Glu  Tyr Ile Asp Gln Ala  Gln Asn Arg Ile Gln  Cys Ala Ile
    1100                1105                1110

Lys Ser  Leu Ser Arg Ile Thr  Glu Met Gln Gln Val  Glu Ala Phe
    1115                1120                1125

Leu Arg  Glu Gly Leu Leu Met  Arg Gly Leu Asn His  Pro Asn Val
    1130                1135                1140

Leu Ala  Leu Ile Gly Ile Met  Leu Pro Pro Glu Gly  Leu Pro His
    1145                1150                1155

Val Leu  Leu Pro Tyr Met Cys  His Gly Asp Leu Leu  Gln Phe Ile
    1160                1165                1170

Arg Ser  Pro Gln Arg Asn Pro  Thr Val Lys Asp Leu  Ile Ser Phe
    1175                1180                1185

Gly Leu  Gln Val Ala Arg Gly  Met Glu Tyr Leu Ala  Glu Gln Lys
    1190                1195                1200

Phe Val  His Arg Asp Leu Ala  Ala Arg Asn Cys Met  Leu Asp Glu
    1205                1210                1215

Ser Phe  Thr Val Lys Val Ala  Asp Phe Gly Leu Ala  Arg Asp Ile
    1220                1225                1230

Leu Asp  Arg Glu Tyr Tyr Ser  Val Gln Gln His Arg  His Ala Arg
    1235                1240                1245

Leu Pro  Val Lys Trp Met Ala  Leu Glu Ser Leu Gln  Thr Tyr Arg
    1250                1255                1260

Phe Thr  Thr Lys Ser Asp Val  Trp Ser Phe Gly Val  Leu Leu Trp
```

```
    1265                1270                1275

Glu Leu  Leu Thr Arg Gly Ala  Pro Pro Tyr Arg His  Ile Asp Pro
    1280                1285                1290

Phe Asp  Leu Thr His Phe Leu  Ala Gln Gly Arg Arg  Leu Pro Gln
    1295                1300                1305

Pro Glu  Tyr Cys Pro Asp Ser  Leu Tyr Gln Val Met  Gln Gln Cys
    1310                1315                1320

Trp Glu  Ala Asp Pro Ala Val  Arg Pro Thr Phe Arg  Val Leu Val
    1325                1330                1335

Gly Glu  Val Glu Gln Ile Val  Ser Ala Leu Leu Gly  Asp His Tyr
    1340                1345                1350

Val Gln  Leu Pro Ala Thr Tyr  Met Asn Leu Gly Pro  Ser Thr Ser
    1355                1360                1365

His Glu  Met Asn Val Arg Pro  Glu Gln Pro Gln Phe  Ser Pro Met
    1370                1375                1380

Pro Gly  Asn Val Arg Arg Pro  Arg Pro Leu Ser Glu  Pro Pro Arg
    1385                1390                1395

Pro Thr
    1400


<210> SEQ ID NO 3
<211> LENGTH: 4000
<212> TYPE: DNA
<213> ORGANISM: Homo sapiens

<400> SEQUENCE: 3

ggatcctcta gggtcccagc tcgcctcgat ggagctcctc ccgccgctgc ctcagtcctt     60

cctgttgctg ctgctgttgc ctgccaagcc cgcggcgggc gaggactggc agtgcccgcg    120

caccccctac gcggcctctc gcgactttga cgtgaagtac gtggtgccca gcttctccgc    180

cggaggcctg gtacaggcca tggtgaccta cgagggcgac agaaatgaga gtgctgtgtt    240

tgtagccata cgcaatcgcc tgcatgtgct tgggcctgac ctgaagtctg tccagagcct    300

ggccacgggc cctgctggag accctggctg ccagacgtgt gcagcctgtg gcccaggacc    360

ccacggccct cccggtgaca cagacacaaa ggtgctggtg ctggatcccg cgctgcctgc    420

gctggtcagt tgtggctcca gcctgcaggg ccgctgcttc ctgcatgacc tagagcccca    480

agggacagcc gtgcatctgg cagcgccagc ctgcctcttc tcagcccacc ataaccggcc    540

cgatgactgc cccgactgtg tggccagccc attgggcacc cgtgtaactg tggttgagca    600

aggccaggcc tcctatttct acgtggcatc ctcactggac gcagccgtgg ctggcagctt    660

cagcccacgc tcagtgtcta tcaggcgtct caaggctgac gcctcgggat tcgcaccggg    720

ctttgtggcg ttgtcagtgc tgcccaagca tcttgtctcc tacagtattg aatacgtgca    780

cagcttccac acgggagcct tcgtatactt cctgactgta cagccggcca gcgtgacaga    840

tgatcctagt gccctgcaca cacgcctggc acggcttagc gccactgagc cagagttggg    900

tgactatcgg gagctggtcc tcgactgcag atttgctcca aaacgcaggc gccgggggc     960

cccagaaggc ggacagccct accctgtgct gcaggtggcc cactccgctc cagtgggtgc   1020

ccaacttgcc actgagctga gcatcgccga gggccaggaa gtactatttg gggtctttgt   1080

gactggcaag gatggtggtc ctggcgtggg ccccaactct gtcgtctgtg ccttccccat   1140

tgacctgctg gacacactaa ttgatgaggg tgtggagcgc tgttgtgaat ccccagtcca   1200

tccaggcctc cggcgaggcc tcgacttctt ccagtcgccc agtttttgcc ccaacccgcc   1260

tggcctggaa gccctcagcc ccaacaccag ctgccgccac ttccctctgc tggtcagtag   1320
```

```
cagcttctca cgtgtggacc tattcaatgg gctgttggga ccagtacagg tcactgcatt   1380
gtatgtgaca cgccttgaca acgtcacagt ggcacacatg ggcacaatgg atgggcgtat   1440
cctgcaggtg gagctggtca ggtcactaaa ctacttgctg tatgtgtcca acttctcact   1500
gggtgacagt gggcagcccg tgcagcggga tgtcagtcgt cttggggacc acctactctt   1560
tgcctctggg gaccaggttt tccaggtacc tatccgaggc cctggctgcc gccacttcct   1620
gacctgtggg cgttgcctaa gggcatggca tttcatgggc tgtggctggt gtgggaacat   1680
gtgcggccag cagaaggagt gtcctggctc ctggcaacag gaccactgcc cacctaagct   1740
tactgagttc cacccccaca gtggacctct aaggggcagt acaaggctga ccctgtgtgg   1800
ctccaacttc taccttcacc cttctggtct ggtgcctgag ggaacccatc aggtcactgt   1860
gggccaaagt ccctgccggc cactgcccaa ggacagctca aaactcagac cagtgccccg   1920
gaaagacttt gtagaggagt ttgagtgtga actggagccc ttgggcaccc aggcagtggg   1980
gcctaccaac gtcagcctca ccgtgactaa catgccaccg ggcaagcact tccgggtaga   2040
cggcacctcc gtgctgagag gcttctcttt catggagcca gtgctgatag cagtgcaacc   2100
cctctttggc ccacgggcag gaggcacctg tctcactctt gaaggccaga gtctgtctgt   2160
aggcaccagc cgggctgtgc tggtcaatgg gactgagtgt ctgctagcac gggtcagtga   2220
ggggcagctt ttatgtgcca cacccctgg ggccacggtg gccagtgtcc cccttagcct   2280
gcaggtgggg ggtgcccagg tacctggttc ctggaccttc cagtacagag aagaccctgt   2340
cgtgctaagc atcagcccca actgtggcta catcaactcc cacatcacca tctgtggcca   2400
gcatctaact tcagcatggc acttagtgct gtcattccat gacgggctta gggcagtgga   2460
aagcaggtgt gagaggcagc ttccagagca gcagctgtgc cgccttcctg aatatgtggt   2520
ccgagacccc cagggatggg tggcagggaa tctgagtgcc cgaggggatg gagctgctgg   2580
ctttacactg cctggctttc gcttcctacc cccaccccat ccacccagtg ccaacctagt   2640
tccactgaag cctgaggagc atgccattaa gtttgagtat attgggctgg gcgctgtggc   2700
tgactgtgtg ggtatcaacg tgaccgtggg tggtgagagc tgccagcacg agttccgggg   2760
ggacatggtt gtctgccccc tgcccccatc cctgcagctt ggccaggatg gtgccccatt   2820
gcaggtctgc gtagatgcac tccctgccat tgatggtctg gattccacca cttgtgtcca   2880
tggagcatcc ttctccgata gtgaagatga atcctgtgtg ccactgctgc ggaaagagtc   2940
catccagcta agggacctgg actctgcgct cttggctgag gtcaaggatg tgctgattcc   3000
ccatgagcgg gtggtcaccc acagtgaccg agtcattggc aaaggccact ttggagttgt   3060
ctaccacgga gaatacatag accaggccca gaatcgaatc caatgtgcca tcaagtcact   3120
aagtcgcatc acagagatgc agcaggtgga ggccttcctg cgagaggggc tgctcatgcg   3180
tggcctgaac cacccgaatg tgctggctct cattggtatc atgttgccac ctgagggcct   3240
gccccatgtg ctgctgccct atatgtgcca cggtgacctg ctccagttca tccgctcacc   3300
tcagcggaac cccaccgtga aggacctcat cagctttggc ctgcaggtag cccgcggcat   3360
ggagtacctg gcagagcaga agtttgtgca cagggacctg gctgcgcgga actgcatgct   3420
ggacgagtca ttcacagtca aggtggctga ctttggtttg gcccgcgaca tcctggacag   3480
ggagtactat agtgttcaac agcatcgcca cgctcgccta cctgtgaagt ggatggcgct   3540
ggagagcctg cagacctata gatttaccac caagtctgat gtggtaccaa gtgatgcagc   3600
aatgctggga ggcagaccca gcagtgcgac ccaccttcag agtactagtg ggggaggtgg   3660
agcagatagt gtctgcactg cttggggacc attatgtgca gctgccagca acctacatga   3720
```

```
actttgagcta accccaaggc tgcctctggg ccatgccagg ccagagcagt ggccctccac   3780

cttgttcctg ccctttaact ttcagaggca ataggtaaat gggcccatta ggtccctcac   3840

tccacagagt gagccagtga gggcagtcct gcaacatgta tttatggagt gcctgctgtg   3900

gaccctgtct tctgggcaca gtggactcag cagtgaccac accaacactg acccttgaac   3960

caataaagga acaaatgact attaaagcac aaaaaaaaaa                         4000


<210> SEQ ID NO 4
<211> LENGTH: 1261
<212> TYPE: PRT
<213> ORGANISM: Homo sapiens

<400> SEQUENCE: 4

Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
```

```
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
            405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750
```

```
Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830

Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro Pro His
    850                 855                 860

Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
                885                 890                 895

Asn Val Thr Val Gly Gly Glu Ser Cys Gln His Glu Phe Arg Gly Asp
            900                 905                 910

Met Val Val Cys Pro Leu Pro Pro Ser Leu Gln Leu Gly Gln Asp Gly
        915                 920                 925

Ala Pro Leu Gln Val Cys Val Asp Ala Leu Pro Ala Ile Asp Gly Leu
    930                 935                 940

Asp Ser Thr Thr Cys Val His Gly Ala Ser Phe Ser Asp Ser Glu Asp
945                 950                 955                 960

Glu Ser Cys Val Pro Leu Leu Arg Lys Glu Ser Ile Gln Leu Arg Asp
                965                 970                 975

Leu Asp Ser Ala Leu Leu Ala Glu Val Lys Asp Val Leu Ile Pro His
            980                 985                 990

Glu Arg Val Val Thr His Ser Asp  Arg Val Ile Gly Lys  Gly His Phe
        995                 1000                 1005

Gly Val  Val Tyr His Gly Glu  Tyr Ile Asp Gln Ala  Gln Asn Arg
    1010                 1015                 1020

Ile Gln  Cys Ala Ile Lys Ser  Leu Ser Arg Ile Thr  Glu Met Gln
    1025                 1030                 1035

Gln Val  Glu Ala Phe Leu Arg  Glu Gly Leu Leu Met  Arg Gly Leu
    1040                 1045                 1050

Asn His  Pro Asn Val Leu Ala  Leu Ile Gly Ile Met  Leu Pro Pro
    1055                 1060                 1065

Glu Gly  Leu Pro His Val Leu  Leu Pro Tyr Met Cys  His Gly Asp
    1070                 1075                 1080

Leu Leu  Gln Phe Ile Arg Ser  Pro Gln Arg Asn Pro  Thr Val Lys
    1085                 1090                 1095

Asp Leu  Ile Ser Phe Gly Leu  Gln Val Ala Arg Gly  Met Glu Tyr
    1100                 1105                 1110

Leu Ala  Glu Gln Lys Phe Val  His Arg Asp Leu Ala  Ala Arg Asn
    1115                 1120                 1125

Cys Met  Leu Asp Glu Ser Phe  Thr Val Lys Val Ala  Asp Phe Gly
    1130                 1135                 1140

Leu Ala  Arg Asp Ile Leu Asp  Arg Glu Tyr Tyr Ser  Val Gln Gln
    1145                 1150                 1155

His Arg  His Ala Arg Leu Pro  Val Lys Trp Met Ala  Leu Glu Ser
    1160                 1165                 1170
```

```
Leu Gln  Thr Tyr Arg Phe Thr  Thr Lys Ser Asp Val  Val Pro Ser
    1175                1180                1185

Asp Ala  Ala Met Leu Gly Gly  Arg Pro Ser Ser Ala  Thr His Leu
    1190                1195                1200

Gln Ser  Thr Ser Gly Gly Gly  Gly Ala Asp Ser Val  Cys Thr Ala
    1205                1210                1215

Trp Gly  Pro Leu Cys Ala Ala  Ala Ser Asn Leu His  Glu Leu Glu
    1220                1225                1230

Leu Thr  Pro Arg Leu Pro Leu  Gly His Ala Arg Pro  Glu Gln Trp
    1235                1240                1245

Pro Ser  Thr Leu Phe Leu Pro  Phe Asn Phe Gln Arg  Gln
    1250                1255                1260


<210> SEQ ID NO 5
<211> LENGTH: 3880
<212> TYPE: DNA
<213> ORGANISM: Homo sapiens

<400> SEQUENCE: 5

ggatcctcta gggtcccagc tcgcctcgat ggagctcctc ccgccgctgc ctcagtcctt     60

cctgttgctg ctgctgttgc ctgccaagcc cgcggcgggc gaggactggc agtgcccgcg    120

cacccccctac gcggcctctc gcgactttga cgtgaagtac gtggtgccca gcttctccgc    180

cggaggcctg gtacaggcca tggtgaccta cgagggcgac agaaatgaga gtgctgtgtt    240

tgtagccata cgcaatcgcc tgcatgtgct tgggcctgac ctgaagtctg tccagagcct    300

ggccacgggc cctgctggag accctggctg ccagacgtgt gcagcctgtg gcccaggacc    360

ccacggccct cccggtgaca cagacacaaa ggtgctggtg ctggatcccg cgctgcctgc    420

gctggtcagt tgtggctcca gcctgcaggg ccgctgcttc ctgcatgacc tagagcccca    480

agggacagcc gtgcatctgg cagcgccagc ctgcctcttc tcagcccacc ataaccggcc    540

cgatgactgc cccgactgtg tggccagccc attgggcacc cgtgtaactg tggttgagca    600

aggccaggcc tcctatttct acgtggcatc ctcactggac gcagccgtgg ctggcagctt    660

cagcccacgc tcagtgtcta tcaggcgtct caaggctgac gcctcgggat tcgcaccggg    720

ctttgtggcg ttgtcagtgc tgcccaagca tcttgtctcc tacagtattg aatacgtgca    780

cagcttccac acgggagcct tcgtatactt cctgactgta cagccggcca gcgtgacaga    840

tgatcctagt gccctgcaca cacgcctggc acggcttagc gccactgagc cagagttggg    900

tgactatcgg gagctggtcc tcgactgcag atttgctcca aaacgcaggc gccggggggc    960

cccagaaggc ggacagccct accctgtgct gcaggtggcc cactccgctc cagtgggtgc   1020

ccaacttgcc actgagctga gcatcgccga gggccaggaa gtactatttg ggtctttgt   1080

gactggcaag gatggtggtc ctggcgtggg ccccaactct gtcgtctgtg ccttccccat   1140

tgacctgctg gacacactaa ttgatgaggg tgtggagcgc tgttgtgaat ccccagtcca   1200

tccaggcctc cggcgaggcc tcgacttctt ccagtcgccc agtttttgcc ccaacccgcc   1260

tggcctggaa gccctcagcc ccaacaccag ctgccgccac ttccctctgc tggtcagtag   1320

cagcttctca cgtgtggacc tattcaatgg gctgttggga ccagtacagg tcactgcatt   1380

gtatgtgaca cgccttgaca acgtcacagt ggcacacatg ggcacaatgg atgggcgtat   1440

cctgcaggtg gagctggtca ggtcactaaa ctacttgctg tatgtgtcca acttctcact   1500

gggtgacagt gggcagcccg tgcagcggga tgtcagtcgt cttggggacc acctactctt   1560

tgcctctggg gaccaggttt tccaggtacc tatccgaggc cctggctgcc gccacttcct   1620
```

```
gacctgtggg cgttgcctaa gggcatggca tttcatgggc tgtggctggt gtgggaacat   1680
gtgcggccag cagaaggagt gtcctggctc ctggcaacag gaccactgcc cacctaagct   1740
tactgagttc cacccccaca gtggacctct aaggggcagt acaaggctga ccctgtgtgg   1800
ctccaacttc taccttcacc cttctggtct ggtgcctgag ggaacccatc aggtcactgt   1860
gggccaaagt ccctgccggc cactgcccaa ggacagctca aaactcagac cagtgccccg   1920
gaaagacttt gtagaggagt ttgagtgtga actggagccc ttgggcaccc aggcagtggg   1980
gcctaccaac gtcagcctca ccgtgactaa catgccaccg ggcaagcact tccgggtaga   2040
cggcacctcc gtgctgagag gcttctcttt catggagcca gtgctgatag cagtgcaacc   2100
cctctttggc ccacgggcag gaggcacctg tctcactctt gaaggccaga gtctgtctgt   2160
aggcaccagc cgggctgtgc tggtcaatgg gactgagtgt ctgctagcac gggtcagtga   2220
ggggcagctt ttatgtgcca cacccccctgg ggccacggtg gccagtgtcc cccttagcct   2280
gcaggtgggg ggtgcccagg tacctggttc ctggaccttc cagtacagag aagaccctgt   2340
cgtgctaagc atcagcccca actgtggcta catcaactcc cacatcacca tctgtggcca   2400
gcatctaact tcagcatggc acttagtgct gtcattccat gacgggctta gggcagtgga   2460
aagcaggtgt gagaggcagc ttccagagca gcagctgtgc cgccttcctg aatatgtggt   2520
ccgagacccc cagggatggg tggcagggaa tctgagtgcc cgaggggatg gagctgctgg   2580
ctttacactg cctggctttc gcttcctacc cccaccccat ccacccagtg ccaacctagt   2640
tccactgaag cctgaggagc atgccattaa gtttgagctt ggccaggatg gtgccccatt   2700
gcaggtctgc gtagatgcac tccctgccat tgatggtctg gattccacca cttgtgtcca   2760
tggagcatcc ttctccgata gtgaagatga atcctgtgtg ccactgctgc ggaaagagtc   2820
catccagcta agggacctgg actctgcgct cttggctgag gtcaaggatg tgctgattcc   2880
ccatgagcgg gtggtcaccc acagtgaccg agtcattggc aaaggccact ttggagttgt   2940
ctaccacgga gaatacatag accaggccca gaatcgaatc caatgtgcca tcaagtcact   3000
aagtcgcatc acagagatgc agcaggtgga ggccttcctg cgagaggggc tgctcatgcg   3060
tggcctgaac cacccgaatg tgctggctct cattggtatc atgttgccac ctgagggcct   3120
gccccatgtg ctgctgccct atatgtgcca cggtgacctg ctccagttca tccgctcacc   3180
tcagcggaac ccccaccgtga aggacctcat cagctttggc ctgcaggtag cccgcggcat   3240
ggagtacctg gcagagcaga agtttgtgca cagggacctg gctgcgcgga actgcatgct   3300
ggacgagtca ttcacagtca aggtggctga ctttggtttg gcccgcgaca tcctggacag   3360
ggagtactat agtgttcaac agcatcgcca cgctcgccta cctgtgaagt ggatggcgct   3420
ggagagcctg cagacctata gatttaccac caagtctgat gtggtaccaa gtgatgcagc   3480
aatgctggga ggcagaccca gcagtgcgac ccaccttcag agtactagtg ggggaggtgg   3540
agcagatagt gtctgcactg cttggggacc attatgtgca gctgccagca acctacatga   3600
acttgagcta accccaaggc tgcctctggg ccatgccagg ccagagcagt ggccctccac   3660
cttgttcctg ccctttaact ttcagaggca ataggtaaat gggcccatta ggtccctcac   3720
tccacagagt gagccagtga gggcagtcct gcaacatgta tttatggagt gcctgctgtg   3780
gaccctgtct tctgggcaca gtggactcag cagtgaccac accaacactg acccttgaac   3840
caataaagga acaaatgact attaaagcac aaaaaaaaaa                         3880
```

<210> SEQ ID NO 6
<211> LENGTH: 1221

<212> TYPE: PRT
<213> ORGANISM: Homo sapiens

<400> SEQUENCE: 6

```
Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400
```

```
Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830
```

-continued

```
Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro Pro His
    850                 855                 860

Pro Pro Ser Ala Asn Leu Val Pro Leu Lys Pro Glu Glu His Ala Ile
865                 870                 875                 880

Lys Phe Glu Leu Gly Gln Asp Gly Ala Pro Leu Gln Val Cys Val Asp
                885                 890                 895

Ala Leu Pro Ala Ile Asp Gly Leu Asp Ser Thr Thr Cys Val His Gly
            900                 905                 910

Ala Ser Phe Ser Asp Ser Glu Asp Glu Ser Cys Val Pro Leu Leu Arg
        915                 920                 925

Lys Glu Ser Ile Gln Leu Arg Asp Leu Asp Ser Ala Leu Leu Ala Glu
    930                 935                 940

Val Lys Asp Val Leu Ile Pro His Glu Arg Val Val Thr His Ser Asp
945                 950                 955                 960

Arg Val Ile Gly Lys Gly His Phe Gly Val Val Tyr His Gly Glu Tyr
                965                 970                 975

Ile Asp Gln Ala Gln Asn Arg Ile Gln Cys Ala Ile Lys Ser Leu Ser
            980                 985                 990

Arg Ile Thr Glu Met Gln Gln Val  Glu Ala Phe Leu Arg  Glu Gly Leu
        995                 1000                1005

Leu Met  Arg Gly Leu Asn His  Pro Asn Val Leu Ala  Leu Ile Gly
    1010                1015                1020

Ile Met  Leu Pro Pro Glu Gly  Leu Pro His Val Leu  Leu Pro Tyr
    1025                1030                1035

Met Cys  His Gly Asp Leu Leu  Gln Phe Ile Arg Ser  Pro Gln Arg
    1040                1045                1050

Asn Pro  Thr Val Lys Asp Leu  Ile Ser Phe Gly Leu  Gln Val Ala
    1055                1060                1065

Arg Gly  Met Glu Tyr Leu Ala  Glu Gln Lys Phe Val  His Arg Asp
    1070                1075                1080

Leu Ala  Ala Arg Asn Cys Met  Leu Asp Glu Ser Phe  Thr Val Lys
    1085                1090                1095

Val Ala  Asp Phe Gly Leu Ala  Arg Asp Ile Leu Asp  Arg Glu Tyr
    1100                1105                1110

Tyr Ser  Val Gln Gln His Arg  His Ala Arg Leu Pro  Val Lys Trp
    1115                1120                1125

Met Ala  Leu Glu Ser Leu Gln  Thr Tyr Arg Phe Thr  Thr Lys Ser
    1130                1135                1140

Asp Val  Val Pro Ser Asp Ala  Ala Met Leu Gly Gly  Arg Pro Ser
    1145                1150                1155

Ser Ala  Thr His Leu Gln Ser  Thr Ser Gly Gly Gly  Gly Ala Asp
    1160                1165                1170

Ser Val  Cys Thr Ala Trp Gly  Pro Leu Cys Ala Ala  Ala Ser Asn
    1175                1180                1185

Leu His  Glu Leu Glu Leu Thr  Pro Arg Leu Pro Leu  Gly His Ala
    1190                1195                1200

Arg Pro  Glu Gln Trp Pro Ser  Thr Leu Phe Leu Pro  Phe Asn Phe
    1205                1210                1215

Gln Arg  Gln
    1220
```

<210> SEQ ID NO 7
<211> LENGTH: 3853
<212> TYPE: DNA
<213> ORGANISM: Homo sapiens

<400> SEQUENCE: 7

```
ggatcctcta gggtcccagc tcgcctcgat ggagctcctc ccgccgctgc ctcagtcctt     60
cctgttgctg ctgctgttgc ctgccaagcc cgcggcgggc gaggactggc agtgcccgcg    120
cacccccctac gcggcctctc gcgactttga cgtgaagtac gtggtgccca gcttctccgc    180
cggaggcctg gtacaggcca tggtgaccta cgagggcgac agaaatgaga gtgctgtgtt    240
tgtagccata cgcaatcgcc tgcatgtgct tgggcctgac ctgaagtctg tccagagcct    300
ggccacgggc cctgctggag accctggctg ccagacgtgt gcagcctgtg gcccaggacc    360
ccacggccct cccggtgaca cagacacaaa ggtgctggtg ctggatcccg cgctgcctgc    420
gctggtcagt tgtggctcca gcctgcaggg ccgctgcttc ctgcatgacc tagagcccca    480
agggacagcc gtgcatctgg cagcgccagc ctgcctcttc tcagcccacc ataaccggcc    540
cgatgactgc cccgactgtg tggccagccc attgggcacc cgtgtaactg tggttgagca    600
aggccaggcc tcctatttct acgtggcatc ctcactggac gcagccgtgg ctggcagctt    660
cagcccacgc tcagtgtcta tcaggcgtct caaggctgac gcctcgggat tcgcaccggg    720
ctttgtggcg ttgtcagtgc tgcccaagca tcttgtctcc tacagtattg aatacgtgca    780
cagcttccac acgggagcct tcgtatactt cctgactgta cagccggcca gcgtgacaga    840
tgatcctagt gccctgcaca cacgcctggc acggcttagc gccactgagc cagagttggg    900
tgactatcgg gagctggtcc tcgactgcag atttgctcca aaacgcaggc gccgggggc    960
cccagaaggc ggacagccct accctgtgct gcaggtggcc cactccgctc cagtgggtgc   1020
ccaacttgcc actgagctga gcatcgccga gggccaggaa gtactatttg ggtctttgt   1080
gactggcaag gatggtggtc ctggcgtggg ccccaactct gtcgtctgtg ccttccccat   1140
tgacctgctg gacacactaa ttgatgaggg tgtggagcgc tgttgtgaat ccccagtcca   1200
tccaggcctc cggcgaggcc tcgacttctt ccagtcgccc agtttttgcc ccaacccgcc   1260
tggcctggaa gccctcagcc ccaacaccag ctgccgccac ttccctctgc tggtcagtag   1320
cagcttctca cgtgtggacc tattcaatgg gctgttggga ccagtacagg tcactgcatt   1380
gtatgtgaca cgccttgaca acgtcacagt ggcacacatg ggcacaatgg atgggcgtat   1440
cctgcaggtg gagctggtca ggtcactaaa ctacttgctg tatgtgtcca acttctcact   1500
gggtgacagt gggcagcccg tgcagcggga tgtcagtcgt cttggggacc acctactctt   1560
tgcctctggg gaccaggttt tccaggtacc tatccgaggc cctggctgcc gccacttcct   1620
gacctgtggg cgttgcctaa gggcatggca tttcatgggc tgtggctggt gtgggaacat   1680
gtgcggccag cagaaggagt gtcctggctc ctggcaacag gaccactgcc cacctaagct   1740
tactgagttc cacccccaca gtggacctct aaggggcagt acaaggctga ccctgtgtgg   1800
ctccaacttc taccttcacc cttctggtct ggtgcctgag ggaacccatc aggtcactgt   1860
gggccaaagt ccctgccggc cactgcccaa ggacagctca aaactcagac cagtgccccg   1920
gaaagacttt gtagaggagt ttgagtgtga actggagccc ttgggcaccc aggcagtggg   1980
gcctaccaac gtcagcctca ccgtgactaa catgccaccg ggcaagcact tccgggtaga   2040
cggcacctcc gtgctgagag gcttctcttt catggagcca gtgctgatag cagtgcaacc   2100
cctctttggc ccacgggcag gaggcacctg tctcactctt gaaggccaga gtctgtctgt   2160
aggcaccagc cgggctgtgc tggtcaatgg gactgagtgt ctgctagcac gggtcagtga   2220
```

```
ggggcagctt ttatgtgcca cacccccctgg ggccacggtg gccagtgtcc cccttagcct   2280

gcaggtgggg ggtgcccagg tacctggttc ctggaccttc cagtacagag aagaccctgt   2340

cgtgctaagc atcagcccca actgtggcta catcaactcc cacatcacca tctgtggcca   2400

gcatctaact tcagcatggc acttagtgct gtcattccat gacgggctta gggcagtgga   2460

aagcaggtgt gagaggcagc ttccagagca gcagctgtgc cgccttcctg aatatgtggt   2520

ccgagacccc cagggatggg tggcagggaa tctgagtgcc cgaggggatg gagctgctgg   2580

ctttacactg cctggctttc gcttcctacc cccaccccat ccacccagtg ccaacctagt   2640

tccactgaag cctgaggagc atgccattaa gtttgaggtc tgcgtagatg cactccctgc   2700

cattgatggt ctggattcca ccacttgtgt ccatggagca tccttctccg atagtgaaga   2760

tgaatcctgt gtgccactgc tgcggaaaga gtccatccag ctaagggacc tggactctgc   2820

gctcttggct gaggtcaagg atgtgctgat tccccatgag cgggtggtca cccacagtga   2880

ccgagtcatt ggcaaaggcc actttggagt tgtctaccac ggagaataca tagaccaggc   2940

ccagaatcga atccaatgtg ccatcaagtc actaagtcgc atcacagaga tgcagcaggt   3000

ggaggccttc ctgcgagagg ggctgctcat gcgtggcctg aaccacccga atgtgctggc   3060

tctcattggt atcatgttgc cacctgaggg cctgccccat gtgctgctgc cctatatgtg   3120

ccacggtgac ctgctccagt tcatccgctc acctcagcgg aaccccaccg tgaaggacct   3180

catcagcttt ggcctgcagg tagcccgcgg catggagtac ctggcagagc agaagtttgt   3240

gcacagggac ctggctgcgc ggaactgcat gctggacgag tcattcacag tcaaggtggc   3300

tgactttggt ttggcccgcg acatcctgga cagggagtac tatagtgttc aacagcatcg   3360

ccacgctcgc ctacctgtga agtggatggc gctggagagc ctgcagacct atagatttac   3420

caccaagtct gatgtggtac caagtgatgc agcaatgctg ggaggcagac ccagcagtgc   3480

gacccacctt cagagtacta gtgggggagg tggagcagat agtgtctgca ctgcttgggg   3540

accattatgt gcagctgcca gcaacctaca tgaacttgag ctaaccccaa ggctgcctct   3600

gggccatgcc aggccagagc agtggccctc caccttgttc ctgcccttta actttcagag   3660

gcaataggta aatgggccca ttaggtccct cactccacag agtgagccag tgagggcagt   3720

cctgcaacat gtatttatgg agtgcctgct gtggaccctg tcttctgggc acagtggact   3780

cagcagtgac cacaccaaca ctgacccttg aaccaataaa ggaacaaatg actattaaag   3840

cacaaaaaaa aaa                                                        3853
```

<210> SEQ ID NO 8
<211> LENGTH: 1212
<212> TYPE: PRT
<213> ORGANISM: Homo sapiens

<400> SEQUENCE: 8

```
Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80
```

```
Leu Gly Pro Asp Leu Lys Ser Val Gln Ser Leu Ala Thr Gly Pro Ala
                 85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510
```

```
Ser Gly Asp Gln Val Phe Gln Val Pro Ile Arg Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830

Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro Pro His
    850                 855                 860

Pro Pro Ser Ala Asn Leu Val Pro Leu Lys Pro Glu Glu His Ala Ile
865                 870                 875                 880

Lys Phe Glu Val Cys Val Asp Ala Leu Pro Ala Ile Asp Gly Leu Asp
                885                 890                 895

Ser Thr Thr Cys Val His Gly Ala Ser Phe Ser Asp Ser Glu Asp Glu
            900                 905                 910

Ser Cys Val Pro Leu Leu Arg Lys Glu Ser Ile Gln Leu Arg Asp Leu
        915                 920                 925

Asp Ser Ala Leu Leu Ala Glu Val Lys Asp Val Leu Ile Pro His Glu
```

```
    930                 935                 940

Arg Val Val Thr His Ser Asp Arg Val Ile Gly Lys Gly His Phe Gly
945                 950                 955                 960

Val Val Tyr His Gly Glu Tyr Ile Asp Gln Ala Gln Asn Arg Ile Gln
                965                 970                 975

Cys Ala Ile Lys Ser Leu Ser Arg Ile Thr Glu Met Gln Gln Val Glu
            980                 985                 990

Ala Phe Leu Arg Glu Gly Leu Leu  Met Arg Gly Leu Asn  His Pro Asn
        995                 1000                1005

Val Leu  Ala Leu Ile Gly Ile  Met Leu Pro Pro Glu  Gly Leu Pro
    1010                1015                1020

His Val  Leu Leu Pro Tyr Met  Cys His Gly Asp Leu  Leu Gln Phe
    1025                1030                1035

Ile Arg  Ser Pro Gln Arg Asn  Pro Thr Val Lys Asp  Leu Ile Ser
    1040                1045                1050

Phe Gly  Leu Gln Val Ala Arg  Gly Met Glu Tyr Leu  Ala Glu Gln
    1055                1060                1065

Lys Phe  Val His Arg Asp Leu  Ala Ala Arg Asn Cys  Met Leu Asp
    1070                1075                1080

Glu Ser  Phe Thr Val Lys Val  Ala Asp Phe Gly Leu  Ala Arg Asp
    1085                1090                1095

Ile Leu  Asp Arg Glu Tyr Tyr  Ser Val Gln Gln His  Arg His Ala
    1100                1105                1110

Arg Leu  Pro Val Lys Trp Met  Ala Leu Glu Ser Leu  Gln Thr Tyr
    1115                1120                1125

Arg Phe  Thr Thr Lys Ser Asp  Val Val Pro Ser Asp  Ala Ala Met
    1130                1135                1140

Leu Gly  Gly Arg Pro Ser Ser  Ala Thr His Leu Gln  Ser Thr Ser
    1145                1150                1155

Gly Gly  Gly Gly Ala Asp Ser  Val Cys Thr Ala Trp  Gly Pro Leu
    1160                1165                1170

Cys Ala  Ala Ala Ser Asn Leu  His Glu Leu Glu Leu  Thr Pro Arg
    1175                1180                1185

Leu Pro  Leu Gly His Ala Arg  Pro Glu Gln Trp Pro  Ser Thr Leu
    1190                1195                1200

Phe Leu  Pro Phe Asn Phe Gln  Arg Gln
    1205                1210


<210> SEQ ID NO 9
<211> LENGTH: 22
<212> TYPE: DNA
<213> ORGANISM: Artificial
<220> FEATURE:
<223> OTHER INFORMATION: forward primer for Ron gene variants

<400> SEQUENCE: 9

gactgagtgt ctgctagcac gg                                              22


<210> SEQ ID NO 10
<211> LENGTH: 22
<212> TYPE: DNA
<213> ORGANISM: Artificial
<220> FEATURE:
<223> OTHER INFORMATION: reverse primer for Ron gene variants

<400> SEQUENCE: 10

atggcaggga gtgcatctac gc                                              22
```

-continued

```
<210> SEQ ID NO 11
<211> LENGTH: 20
<212> TYPE: DNA
<213> ORGANISM: Artificial
<220> FEATURE:
<223> OTHER INFORMATION: forward primer for GAPDH

<400> SEQUENCE: 11

tgggtgtgaa ccatgagaag                                        20


<210> SEQ ID NO 12
<211> LENGTH: 20
<212> TYPE: DNA
<213> ORGANISM: Artificial
<220> FEATURE:
<223> OTHER INFORMATION: reverse primer for GAPDH

<400> SEQUENCE: 12

gtgtcgctgt tgaagtcaga                                        20
```